(12) United States Patent
Guo et al.

(10) Patent No.: US 10,830,716 B2
(45) Date of Patent: Nov. 10, 2020

(54) NANOPARTICLE ASSISTED SCANNING FOCUSING X-RAY FLUORESCENCE IMAGING AND ENHANCED TREATMENT

(71) Applicant: THE REGENTS OF THE UNIVERSITY OF CALIFORNIA, Oakland, CA (US)

(72) Inventors: Ting Guo, Davis, CA (US); R. Andrew Davidson, Davis, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 371 days.

(21) Appl. No.: 15/053,664

(22) Filed: Feb. 25, 2016

(65) Prior Publication Data

US 2016/0252471 A1     Sep. 1, 2016

Related U.S. Application Data

(63) Continuation of application No. PCT/US2014/053259, filed on Aug. 28, 2014.

(60) Provisional application No. 61/871,257, filed on Aug. 28, 2013.

(51) Int. Cl.
| | |
|---|---|
| *G01N 23/223* | (2006.01) |
| *G01N 23/046* | (2018.01) |
| *A61B 6/00* | (2006.01) |
| *A61B 6/03* | (2006.01) |
| *A61N 5/10* | (2006.01) |

(52) U.S. Cl.
CPC .......... *G01N 23/223* (2013.01); *A61B 6/032* (2013.01); *A61B 6/485* (2013.01); *A61N 5/1049* (2013.01); *G01N 23/046* (2013.01); *A61B 6/481* (2013.01); *A61N 2005/1054* (2013.01); *A61N 2005/1098* (2013.01); *G01N 2223/076* (2013.01); *G01N 2223/3303* (2013.01); *G01N 2223/6126* (2013.01)

(58) Field of Classification Search
CPC ..... G01N 2223/076; G01N 2223/3303; G01N 2223/6126; G01N 23/046; G01N 23/223; A61N 2005/1054; A61N 2005/1098; A61N 5/1049
See application file for complete search history.

(56) References Cited

U.S. PATENT DOCUMENTS

| | | | |
|---|---|---|---|
| 5,958,345 A * | 9/1999 | Turner | B01L 3/5085 422/561 |
| 6,404,847 B1 * | 6/2002 | Ueki | G01N 23/223 378/44 |
| 2005/0130240 A1 | 6/2005 | Lin et al. | |
| 2006/0182217 A1 | 8/2006 | Harding et al. | |
| 2006/0188062 A1 | 8/2006 | Agnihotri et al. | |
| 2011/0188629 A1 | 8/2011 | Meng | |

(Continued)

FOREIGN PATENT DOCUMENTS

WO    2015/031675 A1    3/2015

*Primary Examiner* — Chih-Cheng Kao
(74) *Attorney, Agent, or Firm* — Kilpatrick Townsend & Stockton LLP

(57) ABSTRACT

The present disclosure provides systems and methods for providing irradiation energy, imaging, and detecting X-ray fluorescence from a volume in a sample. The present disclosure further relates to methods of increasing the delivery of irradiation energy to a target in a sample.

21 Claims, 27 Drawing Sheets

(56) References Cited

U.S. PATENT DOCUMENTS

2012/0307962 A1* 12/2012 Cho .................. A61K 49/0065
378/6
2013/0251100 A1* 9/2013 Sasaki .................. G01N 23/046
378/20

* cited by examiner

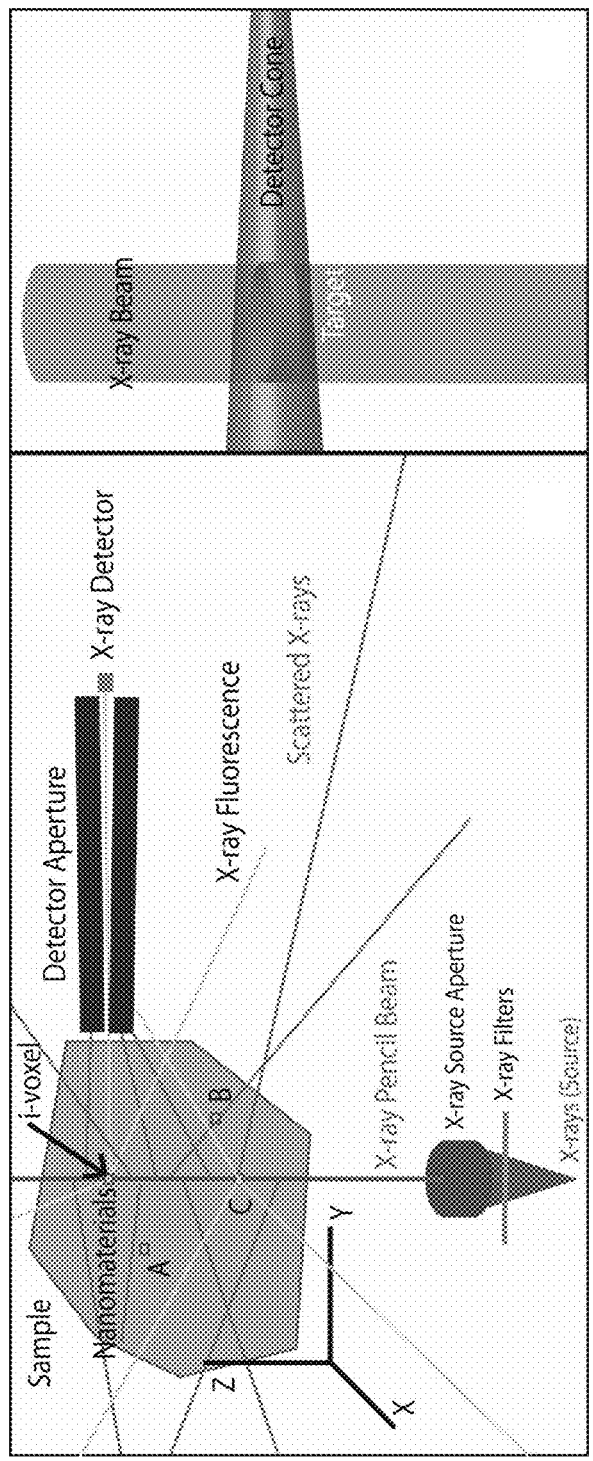

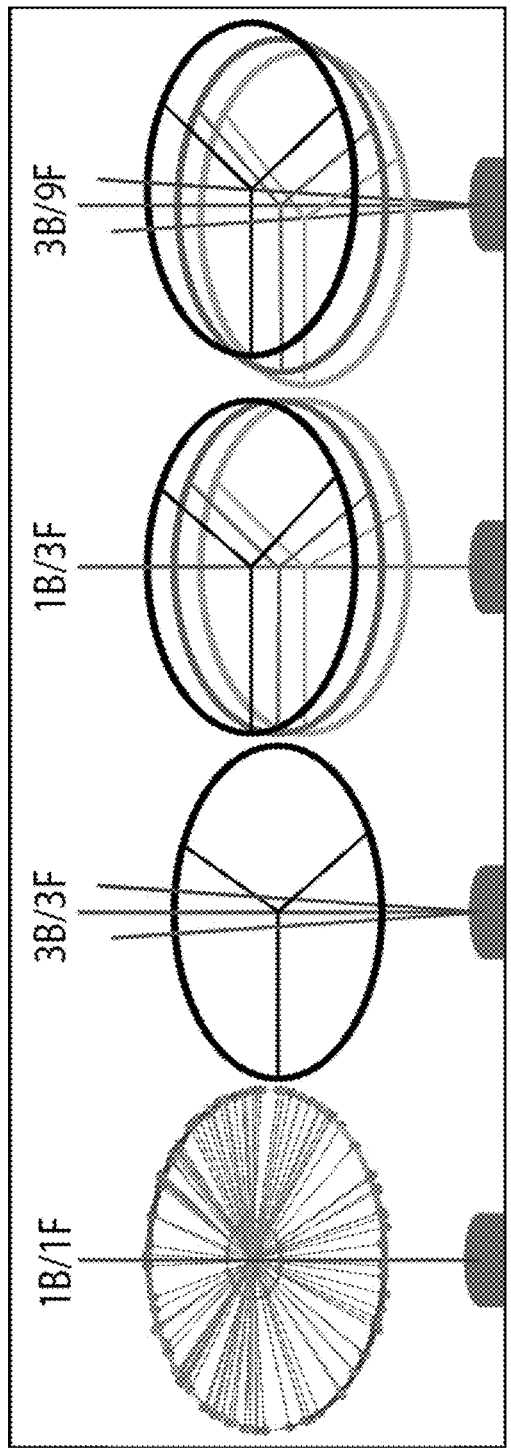

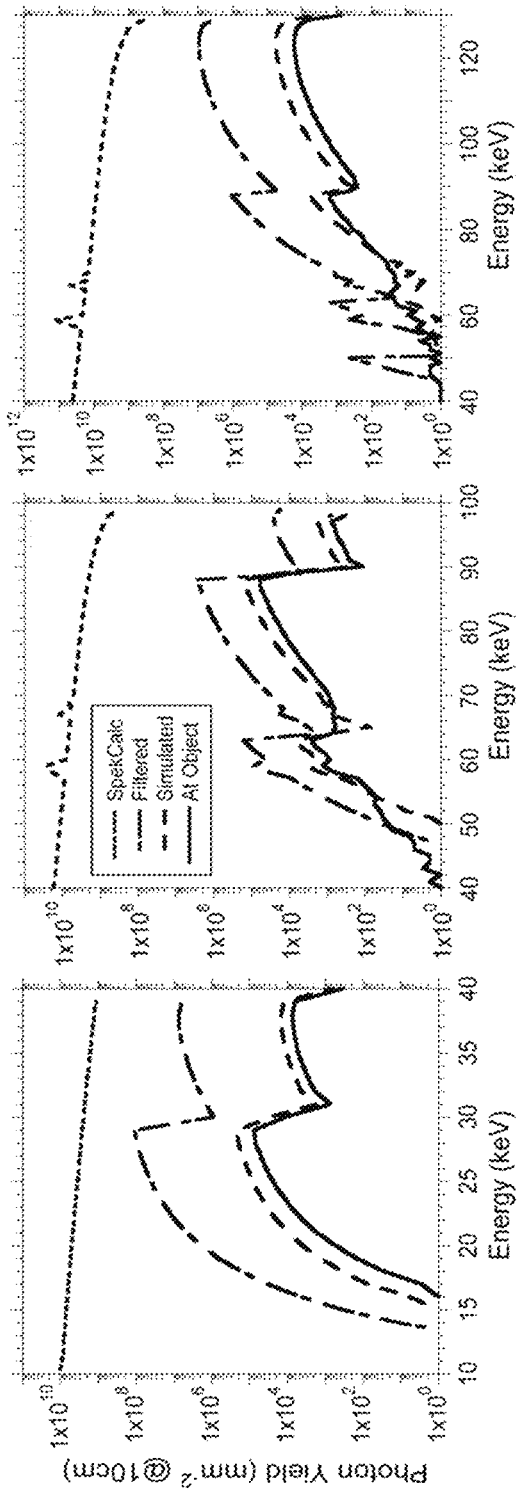

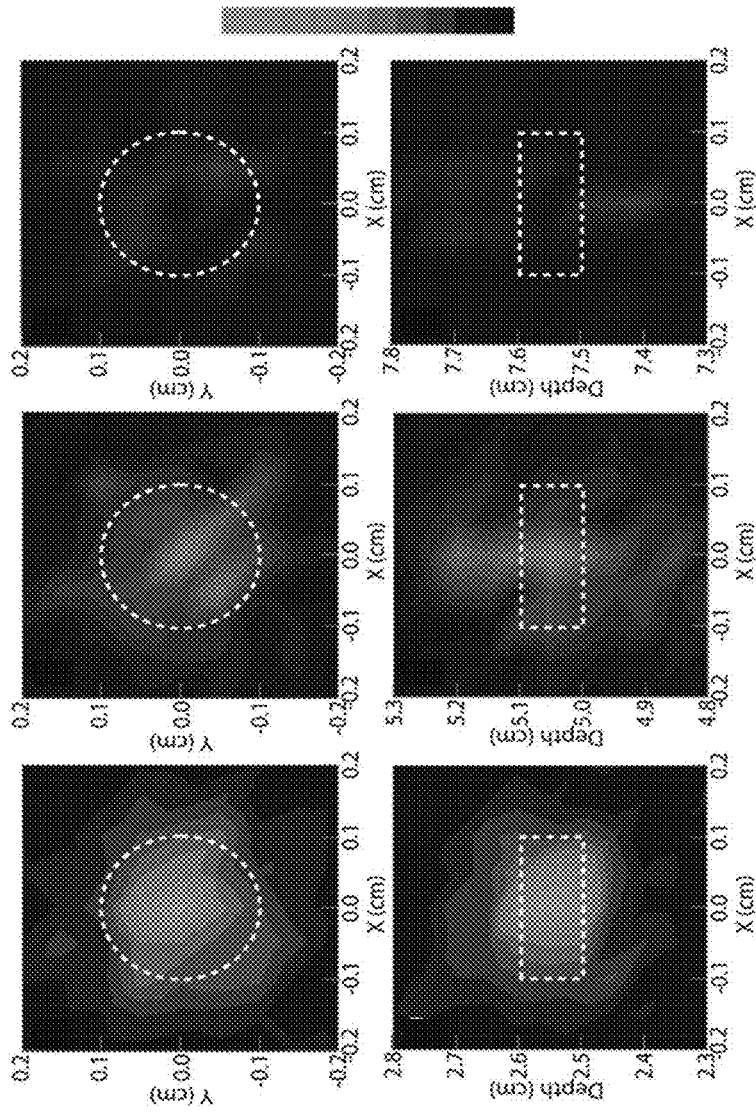

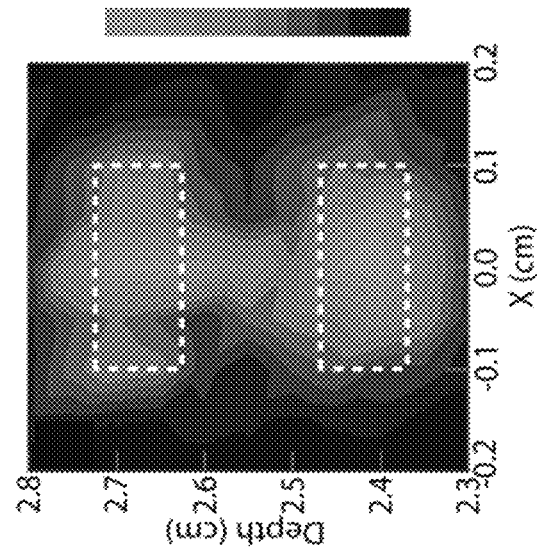
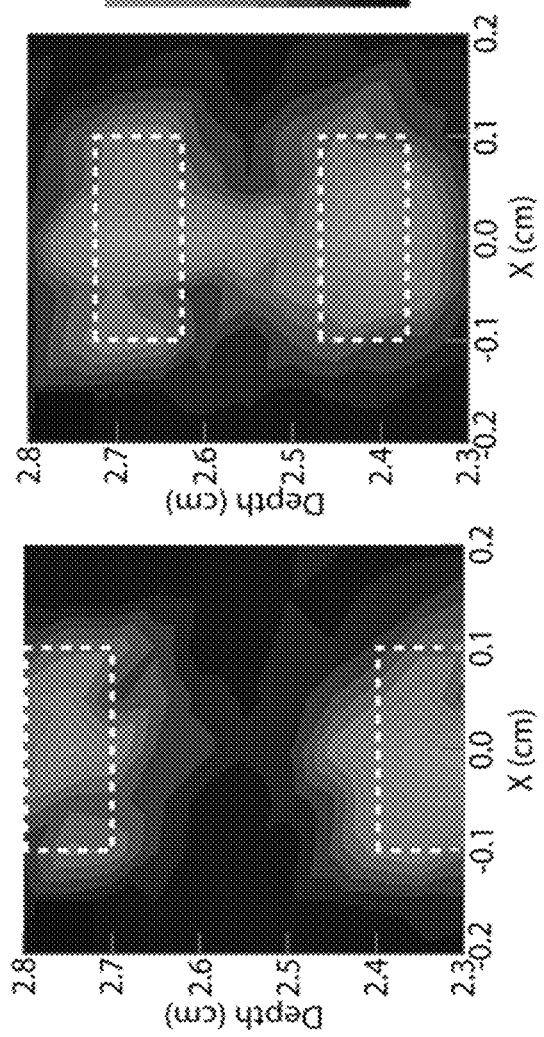
FIG. 6B
FIG. 6A

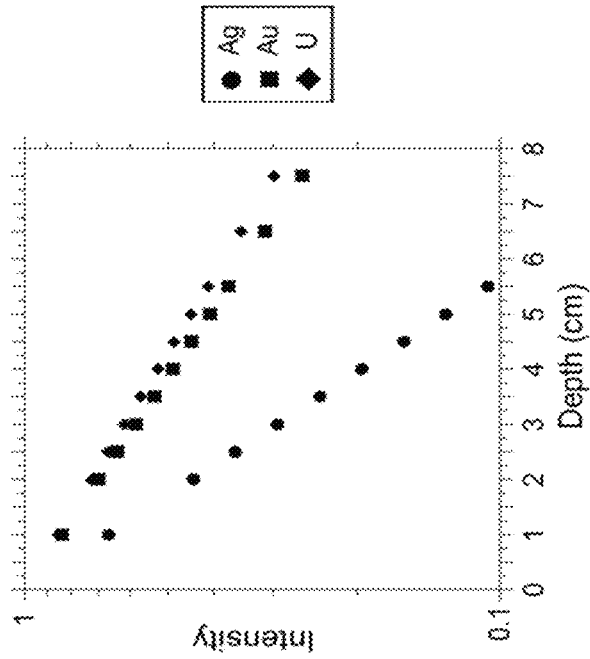
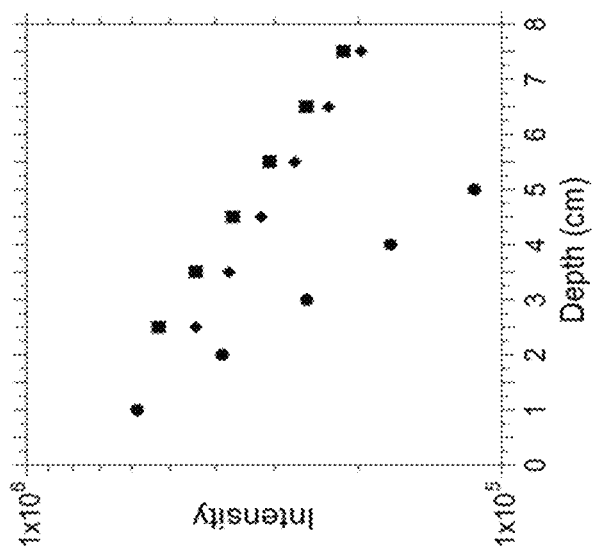
FIG. 8A
FIG. 8B

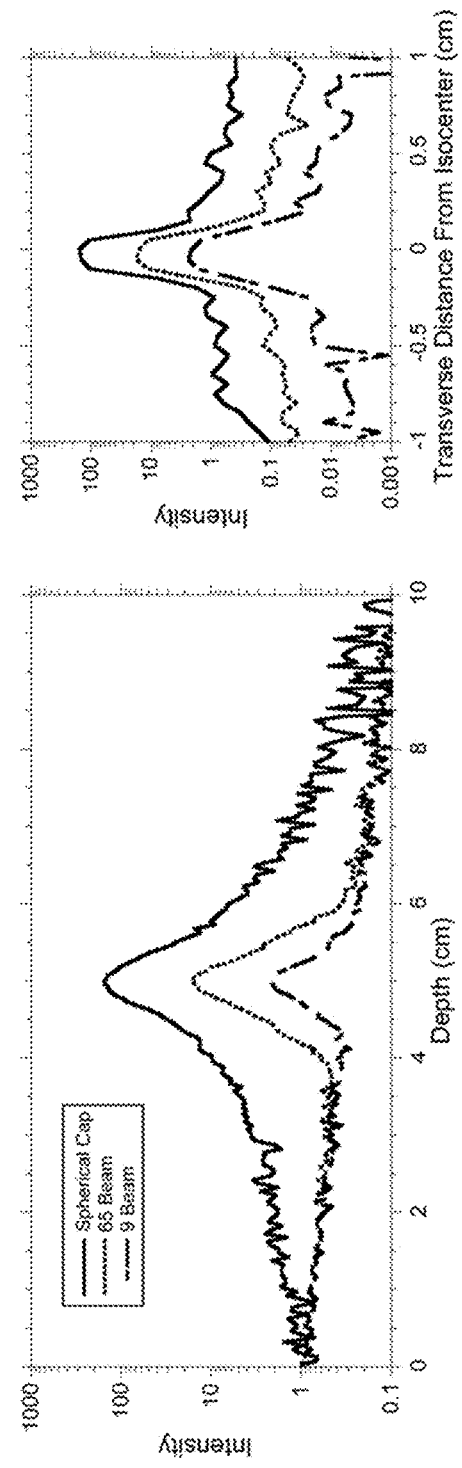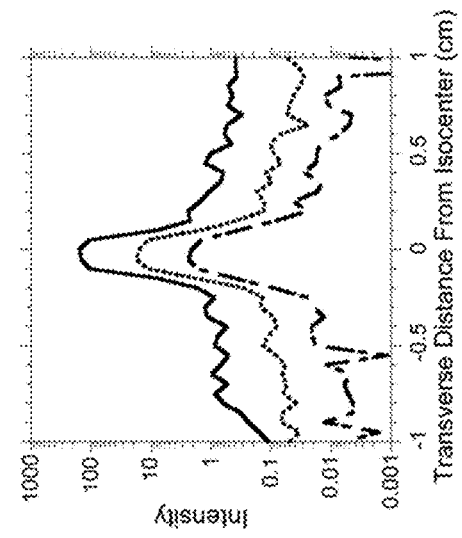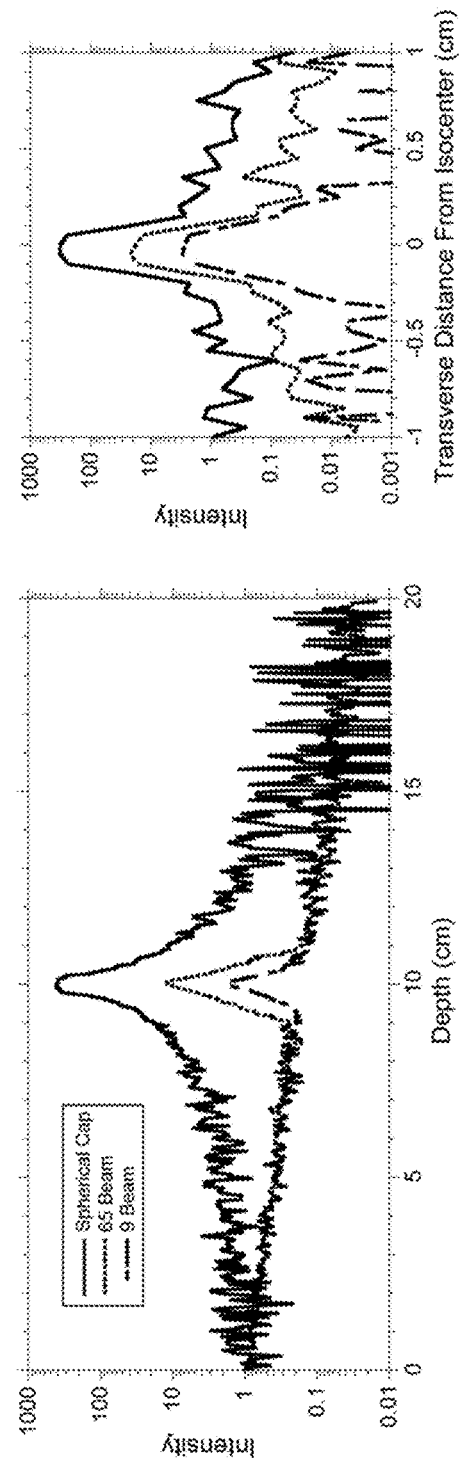
FIG. 12A
FIG. 12B
FIG. 12C
FIG. 12D

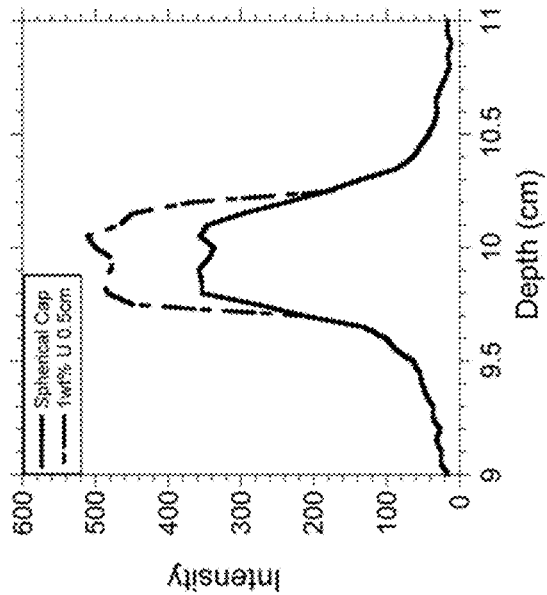
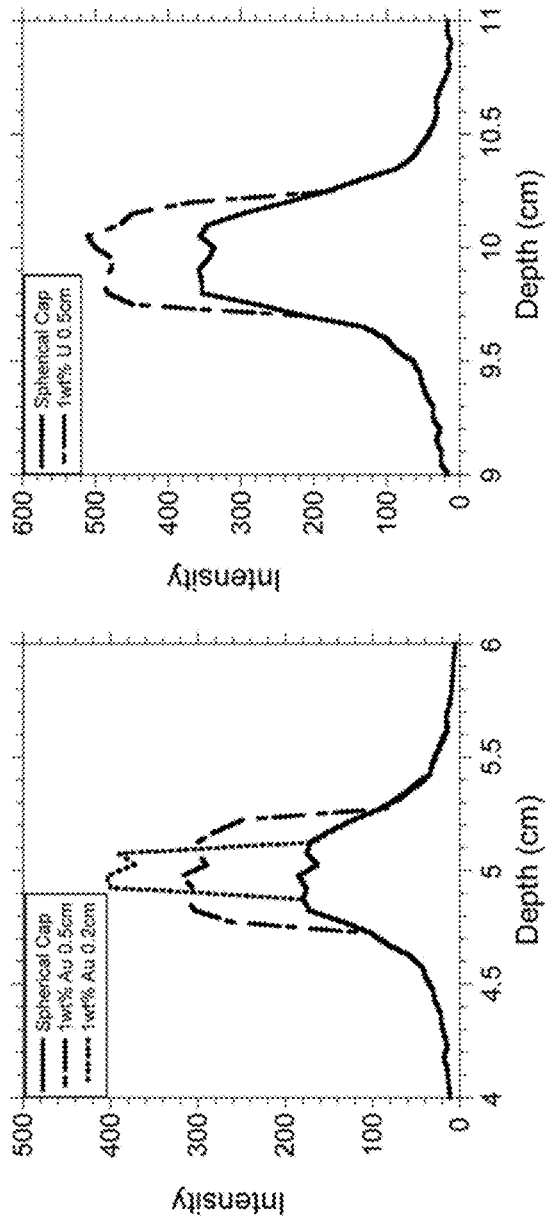
FIG. 13B
FIG. 13A

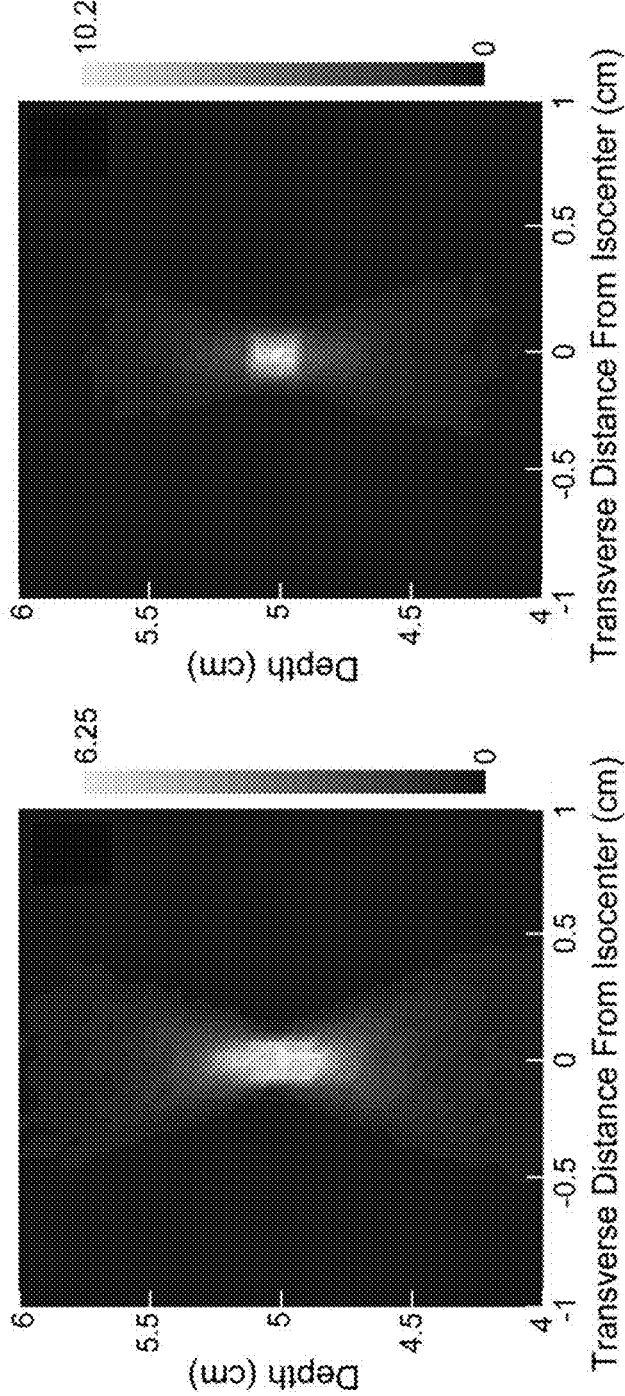

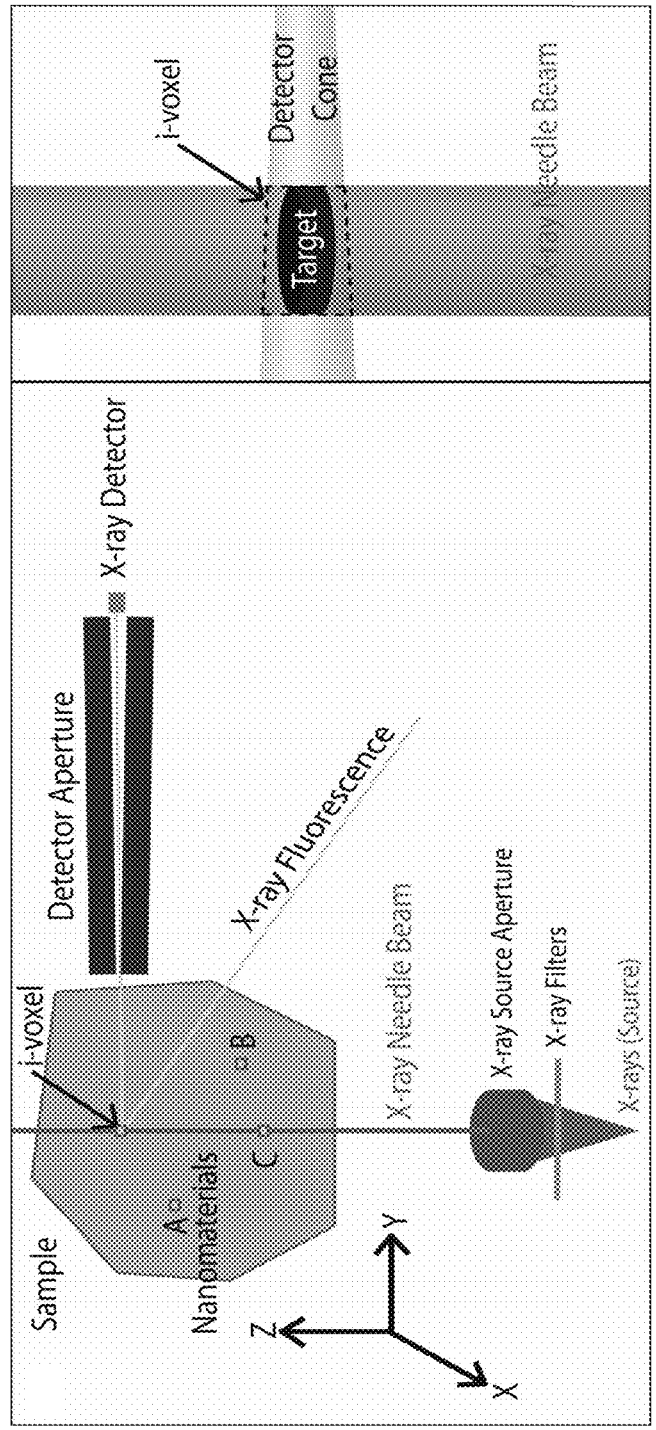

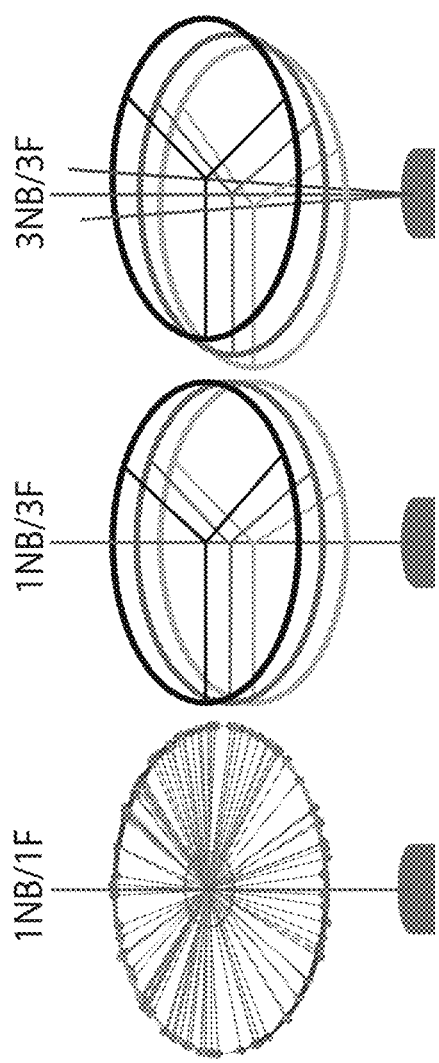

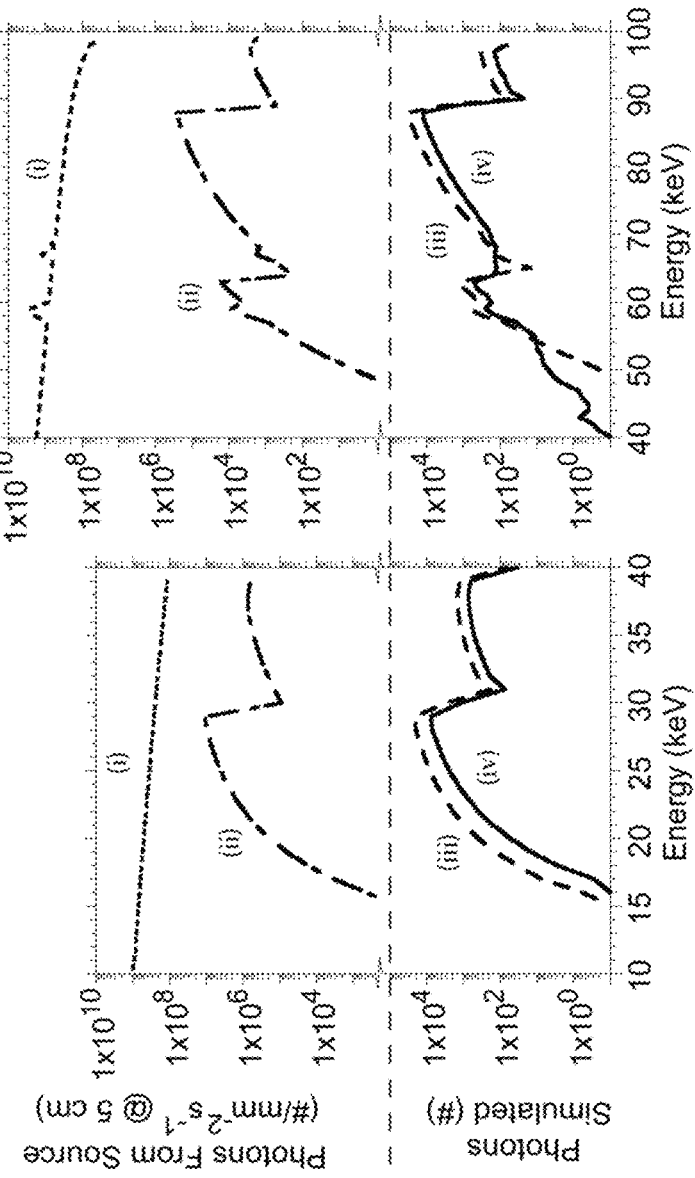

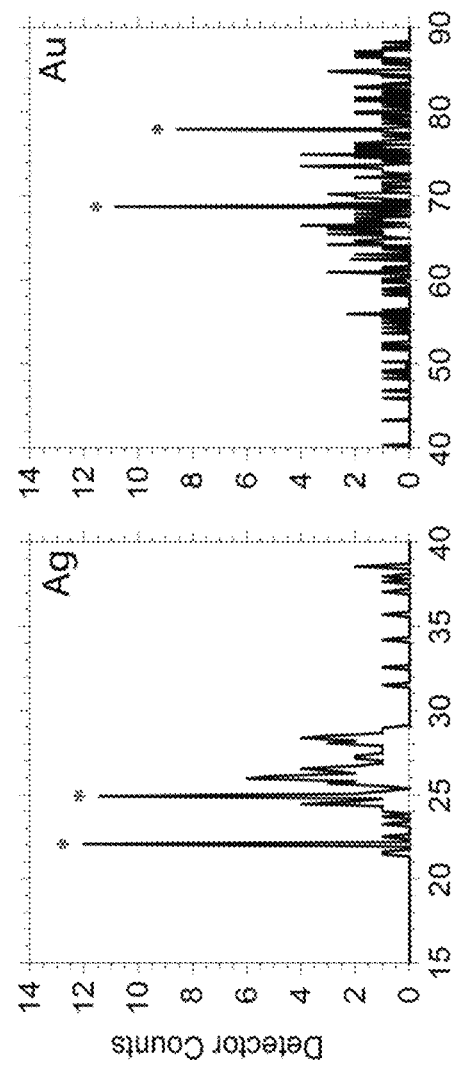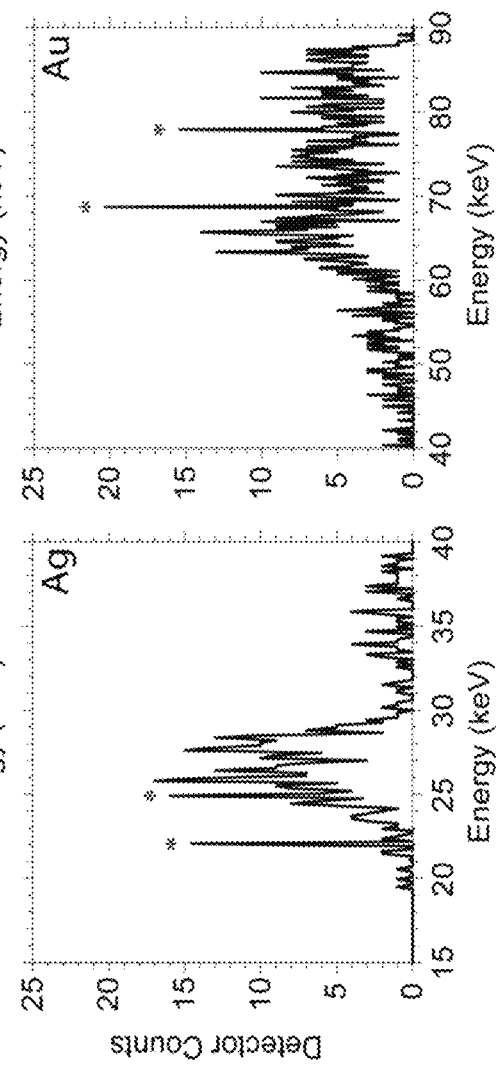
FIG. 19A  FIG. 19B  FIG. 19C  FIG. 19D

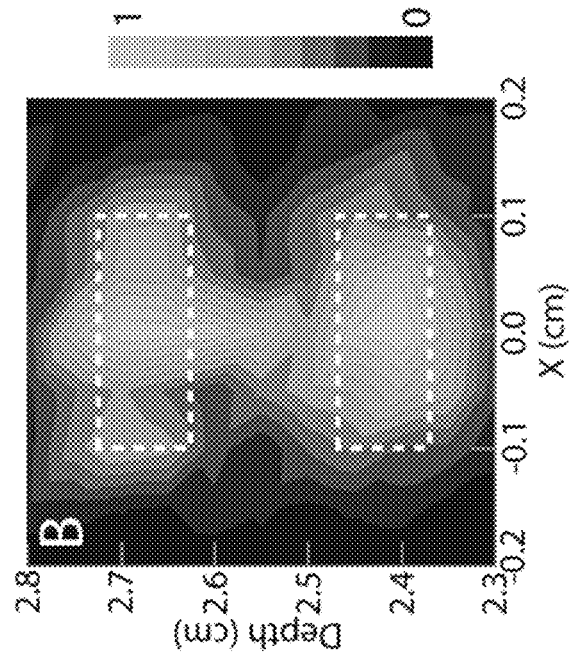
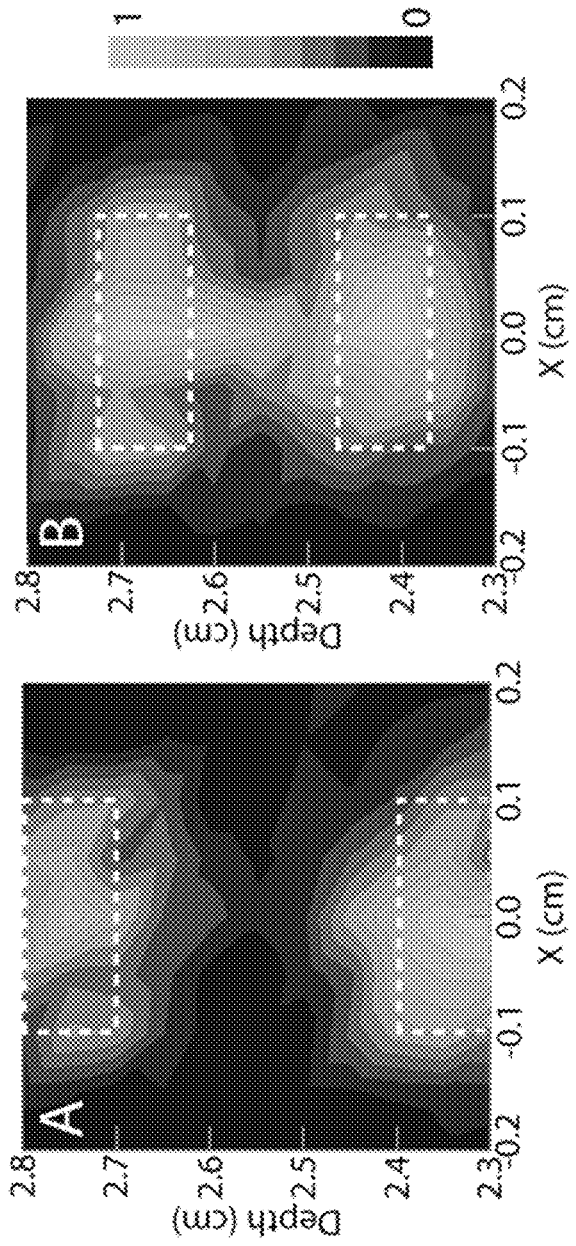
FIG. 21A
FIG. 21B

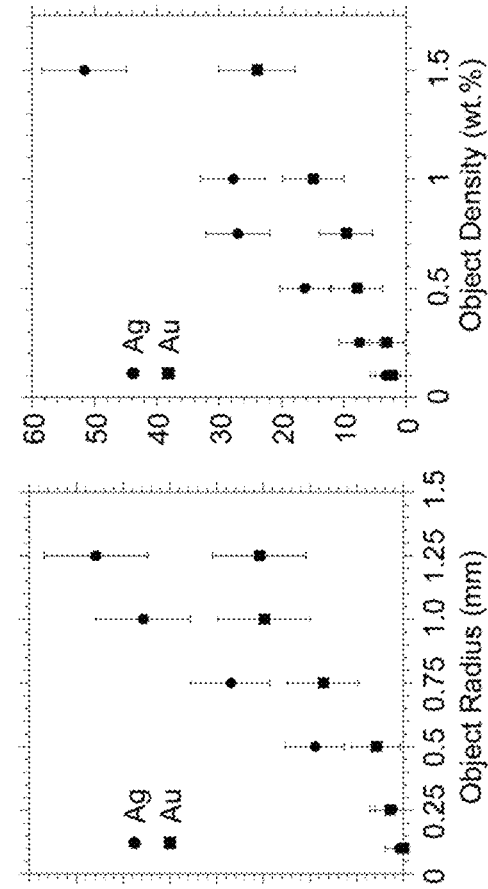

NANOPARTICLE ASSISTED SCANNING FOCUSING X-RAY FLUORESCENCE IMAGING AND ENHANCED TREATMENT

CROSS-REFERENCE(S) TO RELATED APPLICATION(S)

This is a continuation application of PCT/US2014/053259, filed Aug. 28, 2014, which application claims the benefit of U.S. Provisional Application No. 61/871,257 filed Aug. 28, 2013, which are incorporated herein by reference in their entireties.

FIELD

The present disclosure provides systems and methods for providing irradiation energy, imaging, and detecting X-ray fluorescence from a volume in a sample. The present disclosure further relates to methods of increasing the delivery of irradiation energy to a target in a sample.

BACKGROUND

X-ray imaging has played a crucial role in revealing the interiors of dense opaque material objects and anatomy. The imaging principle relies on different parts of the object or body having different attenuation coefficients of X-rays, also known as radiodensities. Computed tomography (CT) takes advantage of various reconstruction techniques to efficiently map out three-dimensional (3D) internal structures of the body or other objects. Similar to conventional 2D X-ray direct imaging, CT depends also on attenuation of X-rays by different body parts, constructing 3D images from multiple high spatial resolution 2D projections that bear the information of the targets with detectable radiodensity differences.

For tumor imaging in the body, the size of the tumor and its radiodensity together determine whether it is possible to detect it by CT. The 2D projections have to show the tumor so that the 3D images can reveal its size and location. This means that the size of tumor and its radiodensity difference from the surrounding healthy tissues have to be great enough for the tumor to show up on the 2D projections. As a result, it is difficult for CT to detect a tumor at early stages due to the low contrast caused by small changes (i.e., less than 10%) in radiodensity within a small volume of tissue (mm in dimension) in comparison to the absorption by the whole length of the body (usually >10 cm) in the X-ray path. In order to detect small radiodensity changes with CT, impractically large doses of X-rays are needed. Hence more sensitive (detecting small tumors less than 1 mm in size), deeper penetrating (>10 cm), higher spatial resolution (mm or less) and low dose (<10 mSv) 3D imaging is needed. Due to the lack of spatial resolution of magnetic resonance imaging (MRI), conventional positron emission tomography (PET) and single photon emission computed tomography (SPECT) and ultrasound imaging, and lack of penetration of optical methods, these methods would not be suitable to detect such subtle changes.

Attempts to improve the sensitivity of CT had been made. One of the recent progresses made in this area is the use of nanoparticles. If there are enough nanoparticles in the tumor region, then regular CT in the absorption mode may be able to detect the tumor taking up large amounts of gold nanoparticles, as demonstrated previously (Luo, T et al., Optics Express, 2011, 19(18): p. 17030-17039). In these cases, even regular CT could detect tumor without gold nanoparticles due to large tumor sizes. For small tumors at early stages in human that take up less gold or silver nanoparticles, the detection with conventional CT has not been attempted. Fluorescent X-ray CT (XFCT) has been developed recently, which is thought to be more sensitive because of decreased background noise. There are several reported variations of this method. Meng et al. used synchrotron X-ray beams and multiple micro apertures to demonstrate a unique way of imaging small samples (Meng, L et al., Proc. of SPIE, 2010, 7804: p. B1-B9). However, the X-ray energies were below 10 keV, which could not be used in tumor detection in humans. Cho et al. developed a technique where a combination of wide X-ray beam and multiple detectors with apertures aiming at quickly detecting large targets loaded with 0.5 wt. % or more gold in small phantoms (Jones, B. L et al., Physics in Medicine and Biology, 2012, 57(23): p. N457-N467). The apertured detectors were only used with the whole sample irradiated to increase the scanning speed. Bazalova et al. showed that it is possible to use more collimated X-ray beams and X-ray fluorescence detectors to image nanoparticle-loaded targets in small phantoms (Bazalova, M et al., Ieee Transactions on Medical Imaging, 2012. 31(8): p. 1620-1627; Bazalova, M et al., International Journal of Radiation Oncology Biology Physics, 2012, 84(3): p. S689-S689; Bazalova, M et al., Physics in Medicine and Biology, 2012, 57(22): p. 7381-7394). The detection principle is still based on the CT concept, and the sensitivity is similar to CT. In all those endeavors, the phantoms were usually small (a few centimeters in diameter) with large targets (millimeters in diameter) loaded with 0.1 to 1.0 wt % gold.

Further, compared with more energetic photons or particles such as MeV X-rays or gamma rays, 50-120 keV X-rays are not commonly used for therapy because of strong absorption of these X-rays by tissues, making it difficult to deliver an adequate dose to a target buried deeply in the body without damaging healthy tissues in the X-ray beam path, especially those near the skin. Nonetheless, recently there are many developments employing nanoparticles to increase the absorption of X-rays at the target. Because these nanoparticles absorb X-rays more intensely than water only at below 120 keV, X-rays in this energy range are preferred. Furthermore, these X-rays sources are inexpensive, more compact and much more convenient to use than other bulkier sources of protons, gamma rays, electrons and neutrons. As a result, if it is possible to use these relatively low energy X-rays to treat cancer, it is then possible to improve the efficacy of radiotherapy while reducing the cost.

To overcome the problem of severe attenuation of 50-120 keV X-rays in the body, new methodologies have to be developed so that the dose at the skin is much less than that at a target deep in a sample such as the human body. One option is to use nanoparticles to increase the absorption of these X-rays at the target. However, the simple, commonly known enhancement factor or type 1 physical enhancement (T1PE) averaged over a macroscopic volume generated is at most four folds by deliverable amounts of nanoparticles (Lee, C et al., J. Phys. Chem. C, 2012, 116(20): p. 11292-11297). Local or type 2 physical enhancement can be much greater, reaching a few hundred folds over a nanoscopic volume, but innovative nanoparticles and mechanisms have to developed and used (Lee, C et al., J. Phys. Chem. C, 2012, 116(20): p. 11292-11297). Hence using the nanoparticles currently available is not a viable approach to deliver large doses in a macroscopic volume deep in the body.

Another way to increase the dose of X-rays at a target deep in the body is to direct multiple X-ray beams at a point in the body, equivalent to focusing the X-rays to this point. A continuously scanning beam or X-ray focusing optics can be used to achieve the same effect. For instance, Norman et al. in 1991 patented a concept of using a rotating beam of X-rays on a plane aiming at an isocenter to enhance the dose at a target in the head (Norman, A. and K. S. Iwamoto, *Therapy X-ray Scanner, in United States Patent,* 1991, The Regents of the University of California: USA). Up to 10-fold enhancement was measured. Uesaka et al. employed a similar idea except that they aimed multiple beams on a plane at the target and observed enhancement with high energy X-rays (Uesaka, M et al., PAC, 2007. Albuquerque, N. Mex.: IEEE). Development in 3D conformal radiation therapy and recent progress in intensity-modulated radiation therapy (IMRT) also use scans on a plane in a circular fashion with varying sizes and cross-sections of a high energy (MeV) X-ray beam from a linear accelerator to deliver more dose at the target. As a result, scanning beams on a plane is promising but has not yet made 50-120 keV X-rays suitable for cancer treatment.

Thus, there exists a need for more sensitive, deeper penetrating, higher spatial resolution, and low dose methods for the detection of a target and the delivery of irradiation energy to a target in a sample.

BRIEF SUMMARY

Accordingly, in one aspect the present disclosure relates to an X-ray fluorescence imaging system, the system including: an X-ray source configured to irradiate a sample with one or more X-ray beams, where the one or more X-rays beams have a defined cross-section; a detector configured to detect X-ray fluorescence; and an aperture configured to define a path of detection from the irradiated sample to the detector, where the path of detection has a defined cross-section and where the detector is configured to detect reflected X-ray fluorescence in an i-voxel formed by the area of intersection of the defined cross-section of the one or more X-ray beams and the defined cross-section of the path of detection. In some embodiments, the detector is configured to scan a volume in the sample. In some embodiments, the volume includes the i-voxel. In some embodiments that may be combined with any of the preceding embodiments, the system further includes a stage configured to hold a sample. In some embodiments that may be combined with any of the preceding embodiments, the one or more X-ray beams are filtered prior to contacting a sample.

In another aspect, the present disclosure relates to a method of detecting a target using X-ray fluorescence imaging, the method including: a) providing a sample including nanoparticles, where the nanoparticles are configured to be associated with a target, b) irradiating the sample with one or more X-ray beams, where the one or more X-ray beams have a defined cross-section and where nanoparticles in the sample contacted by the one or more X-ray beams reflect X-ray fluorescence, c) scanning a first i-voxel with a detector, where a path of detection is formed from the irradiated sample to the detector, where the path of detection has a defined cross-section, and where the detector is configured to detect reflected X-ray fluorescence in an i-voxel formed by the area of intersection of the defined cross-section of the one or more X-ray beams and the defined cross-section of the path of detection, d) scanning a second i-voxel adjacent to the first i-voxel with the detector, e) comparing the detection of reflected X-ray fluorescence in the first i-voxel to the detection of reflected X-ray fluorescence in the second i-voxel, and, f) determining if the sample includes the target.

In some embodiments, one or more of the nanoparticles include a metal selected from silver, gold, and uranium. In some embodiments that may be combined with any of the preceding embodiments, the sample includes about 10 µg or fewer nanoparticles. In some embodiments that may be combined with any of the preceding embodiments, the first or second i-voxel includes about 0.33 wt. % or fewer nanoparticles. In some embodiments that may be combined with any of the preceding embodiments, the sample is about 15 cm or more in dimension. In some embodiments that may be combined with any of the preceding embodiments, detection of reflected X-ray fluorescence occurs about 10 cm or deeper within the sample. In some embodiments that may be combined with any of the preceding embodiments, the detection time is about 10 minutes or less. In some embodiments that may be combined with any of the preceding embodiments, the detection time is about 60 minutes or less. In some embodiments that may be combined with any of the preceding embodiments, the method further includes, after step f): g) identifying a sample that includes the target, where the sample includes a t-voxel including an isocenter located in the interior of the sample, and a volume having equivalent volume to the t-voxel located adjacent to a surface of the sample, and where the volume having equivalent volume to the t-voxel does not include the isocenter, h) irradiating the isocenter with one or more X-ray beams from at least three angles, where the isocenter is irradiated from at least one angle that is out of plane with at least one plane formed by two other angles and where deposition of the irradiation energy from the one or more X-ray beams is greater at the t-voxel as compared to the volume having equivalent volume to the t-voxel, where irradiation of the isocenter occurs for a period of time sufficient for this result to occur. In some embodiments that may be combined with any of the preceding embodiments, the diameter of the one or more X-ray beams is less than 2 mm at the target.

In another aspect, the present disclosure relates to a method of delivering irradiation energy to a sample, the method including: a) providing a sample including a t-voxel including an isocenter located in the interior of the sample, and a volume having equivalent volume to the t-voxel located adjacent to a surface of the sample, where the volume having equivalent volume to the t-voxel does not include the isocenter, b) irradiating the isocenter with one or more X-ray beams from at least three angles, where the isocenter is irradiated from at least one angle that is out of plane with at least one plane formed by two other angles and where deposition of the irradiation energy from the one or more X-ray beams is greater at the t-voxel as compared to the volume having equivalent volume to the t-voxel, wherein irradiation of the isocenter occurs for a period of time sufficient for this result to occur. In some embodiments, the one or more X-ray beams rotate about the isocenter. In some embodiments, the rotation is three-dimensional. In some embodiments that may be combined with any of the preceding embodiments, irradiation energy deposition at the t-voxel is increased about 185-fold or more as compared to the volume having equivalent volume to the t-voxel. In some embodiments that may be combined with any of the preceding embodiments, the sample includes one or more nanoparticles. In some embodiments, one or more of the nanoparticles include a metal selected from silver, gold, and uranium. In some embodiments that may be combined with any of the preceding embodiments, irradiation energy deposition at the t-voxel is increased in the range of about 400-fold to about 800-fold or more as compared to the volume having equivalent volume to the t-voxel. In some embodiments that may be combined with any of the preceding embodiments, the t-voxel includes about 1.0 wt. % or fewer nanoparticles. In some embodiments that may be combined with any of the preceding embodiments, detection occurs about 5 cm or deeper within the sample. In some embodiments that may be combined with any of the preceding embodiments, the irradiation dose is in the range of about 50 keV to about 120 keV. In some embodiments that may be combined with any of the preceding embodiments, the irradiation dose is in the range of about 40 keV to about 130 keV. In some embodiments that may be combined with any of the preceding embodiments, the method further includes, after step b): c) providing the sample with nanoparticles, where the nanoparticles are configured to be associated with a target, d) irradiating the sample with one or more X-ray beams, where the one or more X-ray beams have a defined cross-section, and where nanoparticles in the sample contacted by the one or more X-ray beams reflect X-ray fluorescence, e) scanning a first i-voxel with a detector, where a path of detection is formed from the irradiated sample to the detector, where the path of detection has a defined cross-section, and where the detector is configured to detect reflected X-ray fluorescence in an i-voxel formed by the area of intersection of the defined cross-section of the one or more X-ray beams and the defined cross-section of the path of detection, f) scanning a second i-voxel adjacent to the first i-voxel with the detector, g) comparing the detection of reflected X-ray fluorescence in the first i-voxel to the detection of reflected X-ray fluorescence in the second i-voxel, and, h) determining if the sample includes the target. In some embodiments that may be combined with any of the preceding embodiments, the sample includes a living tissue. In some embodiments that may be combined with any of the preceding embodiments, the target is a tumor. In some embodiments, the tumor is about 1 mm or less in dimension. In some embodiments that may be combined with any of the preceding embodiments, the diameter of the one or more X-ray beams is less than 2 mm at the target. In some embodiments that may be combined with any of the preceding embodiments, for gold nanoparticles, the irradiation energy is in the range of about 50 keV to about 80 keV. In some embodiments that may be combined with any of the preceding embodiments, the surface of the sample is skin.

In one aspect the present disclosure relates to an X-ray fluorescence imaging system, the system including: an X-ray source configured to irradiate a sample with one or more X-ray beams, where the one or more X-rays beams have a defined cross-section; a detector configured to detect X-ray fluorescence; and an aperture configured to define a path of detection from the irradiated sample to the detector, where the path of detection has a defined cross-section and where the detector is configured to detect emitted X-ray fluorescence in an i-voxel formed by the area of intersection of the defined cross-section of the one or more X-ray beams and the defined cross-section of the path of detection. In some embodiments, the detector is configured to scan a volume in the sample. In some embodiments, the volume includes the i-voxel. In some embodiments that may be combined with any of the preceding embodiments, the system further includes a stage configured to hold a sample. In some embodiments that may be combined with any of the preceding embodiments, the one or more X-ray beams are filtered prior to contacting a sample.

In another aspect, the present disclosure relates to a method of detecting a target using X-ray fluorescence imaging, the method including: a) providing a sample including nanoparticles, where the nanoparticles are configured to be associated with a target, b) irradiating the sample with one or more X-ray beams, where the one or more X-ray beams have a defined cross-section and where nanoparticles in the sample contacted by the one or more X-ray beams emit X-ray fluorescence, c) scanning a first i-voxel with a detector, where a path of detection is formed from the irradiated sample to the detector, where the path of detection has a defined cross-section, and where the detector is configured to detect emitted X-ray fluorescence in an i-voxel formed by the area of intersection of the defined cross-section of the one or more X-ray beams and the defined cross-section of the path of detection, d) scanning a second i-voxel adjacent to the first i-voxel with the detector, e) comparing the detection of emitted X-ray fluorescence in the first i-voxel to the detection of emitted X-ray fluorescence in the second i-voxel, and, f) determining if the sample includes the target. In some embodiments, one or more of the nanoparticles include a metal selected from silver, gold, and uranium. In some embodiments that may be combined with any of the preceding embodiments, the sample includes about 10 µg or fewer nanoparticles. In some embodiments that may be combined with any of the preceding embodiments, the first or second i-voxel includes about 0.33 wt. % or fewer nanoparticles. In some embodiments that may be combined with any of the preceding embodiments, the sample is about 15 cm or more in dimension. In some embodiments that may be combined with any of the preceding embodiments, detection of emitted X-ray fluorescence occurs about 10 cm or deeper within the sample. In some embodiments that may be combined with any of the preceding embodiments, the detection time is about 10 minutes or less. In some embodiments that may be combined with any of the preceding embodiments, the detection time is about 60 minutes or less. In some embodiments that may be combined with any of the preceding embodiments, the method further includes, after step f): g) identifying a sample that includes the target, where the sample includes a t-voxel including an isocenter located in the interior of the sample, and a volume having equivalent volume to the t-voxel located adjacent to a surface of the sample, and where the volume having equivalent volume to the t-voxel does not include the isocenter, h) irradiating the isocenter with one or more X-ray beams from at least three angles, where the isocenter is irradiated from at least one angle that is out of plane with at least one plane formed by two other angles and where deposition of the irradiation energy from the one or more X-ray beams is greater at the t-voxel as compared to the volume having equivalent volume to the t-voxel, where irradiation of the isocenter occurs for a period of time sufficient for this result to occur. In some embodiments that may be combined with any of the preceding embodiments, the diameter of the one or more X-ray beams is less than 2 mm at the target.

In another aspect, the present disclosure relates to a method of delivering irradiation energy to a sample, the method including: a) providing a sample including a t-voxel including an isocenter located in the interior of the sample, and a volume having equivalent volume to the t-voxel located adjacent to a surface of the sample, where the volume having equivalent volume to the t-voxel does not include the isocenter, b) irradiating the isocenter with one or more X-ray beams from at least three angles, where the isocenter is irradiated from at least one angle that is out of plane with at least one plane formed by two other angles and where deposition of the irradiation energy from the one or more X-ray beams is greater at the t-voxel as compared to the volume having equivalent volume to the t-voxel, wherein irradiation of the isocenter occurs for a period of time sufficient for this result to occur. In some embodiments, the one or more X-ray beams rotate about the isocenter. In some embodiments, the rotation is three-dimensional. In some embodiments that may be combined with any of the preceding embodiments, irradiation energy deposition at the t-voxel is increased about 185-fold or more as compared to the volume having equivalent volume to the t-voxel. In some embodiments that may be combined with any of the preceding embodiments, the sample includes one or more nanoparticles. In some embodiments, one or more of the nanoparticles include a metal selected from silver, gold, and uranium. In some embodiments that may be combined with any of the preceding embodiments, irradiation energy deposition at the t-voxel is increased in the range of about 400-fold to about 800-fold or more as compared to the volume having equivalent volume to the t-voxel. In some embodiments that may be combined with any of the preceding embodiments, the t-voxel includes about 1.0 wt. % or fewer nanoparticles. In some embodiments that may be combined with any of the preceding embodiments, detection occurs about 5 cm or deeper within the sample. In some embodiments that may be combined with any of the preceding embodiments, the irradiation dose is in the range of about 50 keV to about 120 keV. In some embodiments that may be combined with any of the preceding embodiments, the irradiation dose is in the range of about 40 keV to about 130 keV. In some embodiments that may be combined with any of the preceding embodiments, the method further includes, after step b): c) providing the sample with nanoparticles, where the nanoparticles are configured to be associated with a target, d) irradiating the sample with one or more X-ray beams, where the one or more X-ray beams have a defined cross-section, and where nanoparticles in the sample contacted by the one or more X-ray beams emit X-ray fluorescence, e) scanning a first i-voxel with a detector, where a path of detection is formed from the irradiated sample to the detector, where the path of detection has a defined cross-section, and where the detector is configured to detect emitted X-ray fluorescence in an i-voxel formed by the area of intersection of the defined cross-section of the one or more X-ray beams and the defined cross-section of the path of detection, f) scanning a second i-voxel adjacent to the first i-voxel with the detector, g) comparing the detection of emitted X-ray fluorescence in the first i-voxel to the detection of emitted X-ray fluorescence in the second i-voxel, and, h) determining if the sample includes the target. In some embodiments that may be combined with any of the preceding embodiments, the sample includes a living tissue. In some embodiments that may be combined with any of the preceding embodiments, the target is a tumor. In some embodiments, the tumor is about 1 mm or less in dimension. In some embodiments that may be combined with any of the preceding embodiments, the diameter of the one or more X-ray beams is less than 2 mm at the target. In some embodiments that may be combined with any of the preceding embodiments, for gold nanoparticles, the irradiation energy is in the range of about 50 keV to about 80 keV. In some embodiments that may be combined with any of the preceding embodiments, the surface of the sample is skin.

DESCRIPTION OF THE FIGURES

FIGS. 1A-FIG. 1B illustrate the schematics of the working principle of a new imaging instrument. FIG. 1A illustrates how fluorescent X-rays from the imaging voxel (i-voxel) are detected by a detector equipped with an aperture, which eliminates most of the scattered X-rays from the sample irradiated with the X-ray beam. Other targets are not irradiated (points A and B) or are irradiated but not detected (point C). FIG. 1B illustrates the zoom-in in the i-voxel region. The i-voxel is formed between the X-ray beam and the detector cone. The i-voxel is larger than that of the target in this case.

FIGS. 2A-FIG. 2D illustrate four exemplary configurations of beam and detector arrangements. FIG. 2A illustrates the single beam and single ring of detectors with a single focus. FIG. 2B illustrates three beam (from the same source) and three foci from a single ring of detectors. FIG. 2C illustrates one beam and three rings of detectors, each with a single focus. FIG. 2D illustrates three beams (from the same source) and three rings of detectors, each ring with three separate foci.

FIG. 3A illustrates X-ray spectra at different stages of the simulation: i) emitted from the X-ray source (40 kVp) (SpekCalc), ii) after filters (combination of 200 µm Tin and 150 µm Cu) (Filtered), iii) simulated photons (Simulated), and iv) at the 2.5 cm deep in the 5-cm cube of water (At Object). FIG. 3B is identical to FIG. 3A, but the voltage of the source is set to 100 kVp and the Ag is replaced with Au and sample size is changed to a 10-cm cube. FIG. 3C is identical to FIG. 3A, but the source is set to 130 kVp and the target is 0.5 wt % $^{238}$U, which absorbs at 115 keV and emits Kα at 98.4 keV and has a half-life is 4 billion years, meaning it emits 1 pCi from 1 µg of $^{238}$U. The sample size is a 15-cm cube.

FIGS. 5A-FIG. 5H illustrate simulated 3D imaging of the targets in the sample. FIG. 5E illustrates the 3D view of the X-ray beam irradiating a target in the sample. FIG. 5A illustrates the 3D contour plot of the zoom-in of the imaged target. FIG. 5B (axial view) and FIG. 5F (transverse view) illustrate a 1 wt. % of Ag disc target in a 5-cm cube of water; FIG. 5C and FIG. 5G illustrate a 1 wt. % Au target in 10-cm cube; and FIG. 5D and FIG. 5H illustrate an identical target of U in 15-cm cube.

FIGS. 6A-FIG. 6B illustrate the images of two targets of Ag nanoparticles at different distances in the sample. FIG. 6A illustrates that the two targets are separated by 3 mm, which shows that they are clearly separated. FIG. 6B illustrates that the two objects separated by 2 mm at which two targets are still well separated, although the middle starts to fill up with fluorescent photons.

FIG. 7A with different detector aperture openings; FIG. 7B as a function of target diameter for a fixed X-ray beam diameter; and FIG. 7C with different total amount of Ag in the target.

FIGS. 8A-FIG. 8B illustrate the fluorescence intensity of targets of Ag, Au and U at different depths in the sample. FIG. 8A illustrates the relative signals for three cases as a function of depth. FIG. 8B illustrates the data from FIG. 8A, but the signal is normalized to the number of incoming photons.

FIG. 9A illustrates a flow chart of the simulation steps for photons through the water cube sample. FIG. 9B illustrates the fluorescence from the target of nanoparticle aqueous solution.

FIGS. 12A-FIG. 12D illustrate X-ray intensity profiles for three configurations of focusing using a beam or beams of X-rays for two different sources operated at 60 (FIG. 12A and FIG. 12B) and 110 kVp (FIG. 12C and FIG. 12D). FIG. 12A illustrates the intensity of X-rays as a function of depth of penetration for three configurations. FIG. 12B illustrates the same as in FIG. 12A, but in the transverse direction. FIG. 12C illustrates the depth intensity profiles for 110 kVp X-rays. FIG. 12D illustrates the same as in FIG. 12C, but in the transverse direction.

FIG. 13A illustrates the dose enhancement of adding gold into a treatment voxel (t-voxel). Two thicknesses are used, 2 mm and 5 mm. 404-fold enhancement is achieved using 2-mm thick gold in the t-voxel. With a 5-mm thick layer, the highest dose is 318 times that at the entrance. FIG. 13B illustrates the same dose enhancement for putting 1 wt. % U in a 5-mm thick layer centered at the isocenter. Up to 511 fold increase in dose is predicted compared with that at the entrance or surface of the sample.

FIG. 14A illustrates the shape of the enhancement region (t-voxel) without Au nanoparticles. FIG. 14B illustrates the shape of the enhancement region (t-voxel) with Au nanoparticles. In FIG. 14A, the shape without nanoparticles assumes an oblate spheroidal shape with the longer axis in the axial direction. The width of the oblate spheroid is approximately the diameter of the X-ray beam. The length of the oblate spheroid is determined by the focusing configuration. In the continuous scanning configuration, the length is 5.75 mm. With the addition of nanoparticles, the length becomes almost the same as the thickness of the nanoparticle layer, which in this case is 2 mm. FIG. 14B is normalized to the highest enhancement of 404-fold from 185-fold as shown in FIG. 14A.

FIGS. 15A-FIG. 15B illustrate a schematic of the working principle of a new imaging instrument. FIG. 15A illustrates how fluorescent X-rays from the imaging voxel (i-voxel) are detected by a detector equipped with an aperture, which eliminates most of the scattered X-rays from the sample irradiated with the X-ray needle beam. Other targets are not irradiated (points A and B), or irradiated but not detected (point C). FIG. 15B illustrates the zoom-in of the i-voxel region. The i-voxel is formed between the X-ray needle beam and the detector cone. The i-voxel is slightly larger than that of the target in this case.

FIGS. 16A-FIG. 16C illustrate three configurations of beam and detector arrangement. FIG. 16A shows the single beam and single ring of detectors with a single focus. FIG. 16B shows one beam and three foci from a three rings of detectors. FIG. 16C shows three beams (from the same source) and three rings of detectors, each with a single focus.

FIG. 17A shows the free path of 81 keV photons through a water phantom compared to NIST attenuation data. FIG. 17B is similar to FIG. 17A, but through a Au phantom.

FIG. 18A shows X-ray spectra at different stages of the simulation: i) emitted from the X-ray source (40 kVp, short dash), ii) after filters (combination of 200 μm Tin and 150 μm Cu, dot-dashed), iii) simulated photons (dashed), and iv) at the 2.5 cm deep in the 5 cm cube of water (solid). FIG. 18B is similar to FIG. 18A, but the voltage of the source is set to 100 kVp, the Ag is replaced with Au, the sample size is changed to a 10 cm cube with the flux calculated at 5 cm depth, and the filters are 1 mm Pb and Sn and 0.5 mm Lu.

FIGS. 19A-FIG. 19D illustrate the spectrum of detected photons by the X-ray detectors with apertures for 31.4 μg Ag in the middle of a 5 cm cube and 31.4 μg Au in the middle of a 10 cm cube. The energy resolution is determined by the detector, which is 150 eV. Signal counts (peaks marked with *) in the E-bins containing $K_\alpha$ and $K_\beta$ are (FIG. 19A) $K_\alpha$=12±4.1 $K_\beta$=11.4±3.3; (FIG. 19B) $K_\alpha$=10.9±2.6 $K_\beta$=8.6±2.0; (FIG. 19C) $K_\alpha$=14.6±4.5 $K_\beta$=16.0±3.2; (FIG. 19D) $K_\alpha$ 20.3±3.3 $K_\beta$=15.4±2.6. FIG. 19A and FIG. 19B are with a front aperture height of 1.75 mm. FIG. 19C and FIG. 19D are with the apertures removed.

FIG. 20A shows the 3D contour plot of the magnified image of the target. FIG. 20B (axial view) and FIG. 20E (transverse view) show a 1 wt. % of Ag disc target in a 5 cm cube of water; FIG. 20C and FIG. 20F for a 1 wt. % Au target in 10 cm cube. (The Au case is normalized against Ag). FIG. 20D shows the 3D view of the X-ray beam irradiating a target in the sample and the detector ring (not to scale).

FIGS. 21A-FIG. 21B illustrate the images of two targets containing 1 wt. % Ag at different distances in the sample. FIG. 21A shows the two targets are separated by 3 mm, which shows that they are clearly separated. FIG. 21B shows the two objects separated by 1.5 mm at which the two targets are still separated, although the middle starts to fill up with fluorescent photons.

FIGS. 22A-FIG. 22C illustrate signal to noise ratios (S/N) in three experimental situations. FIG. 22A shows the S/N with different detector aperture opening heights. FIG. 22B shows the S/N as a function of target diameter for a fixed X-ray beam diameter. FIG. 22C shows the S/N with different total amounts of Ag or Au in the target.

FIG. 26A shows the dose enhancement as a function of depth of penetration for three beam configurations. FIG. 26B shows the same in the transverse direction. FIG. 26C shows the depth dependent dose enhancement profiles for 110 kVp X-rays. FIG. 26D is similar to FIG. 26C, but shown in the transverse direction.

DETAILED DESCRIPTION

Figure 4C:
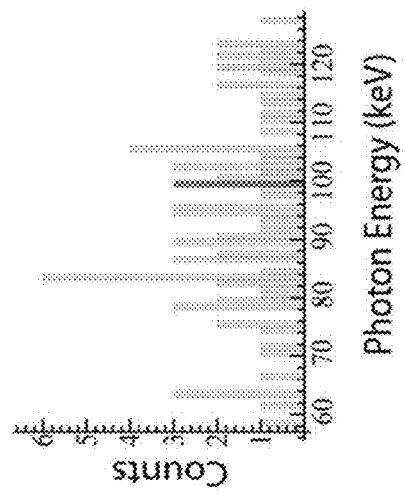
FIGS. 4A-FIG. 4C illustrate the detected fluorescent (darker gray) and scattered (lighter gray) photons by the X-ray detectors with apertures for 31.7 µg Ag in the middle of a 5-cm side cube in FIG. 4A, 31 µg Au in the middle of a 10-cm side cube in FIG. 4B, and 31 µg U in 15-cm side cube in FIG. 4C. The energy resolution simulates that of the detector, which is 150 eV.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

The present disclosure provides systems and methods for providing irradiation energy, imaging, and detecting X-ray fluorescence from a volume in a sample. The present disclosure further relates to methods of increasing the delivery of irradiation energy to a target in a sample.

Accordingly, the present disclosure is based, at least in part, on Applicant's discovery of an imaging method to sensitively detect X-ray fluorescence from nanoparticle-containing targets within large objects or samples that are irradiated by an X-ray beam or multiple X-ray beams from one or more X-ray sources. This method can detect the amount and location of small amounts of these nanoparticles in samples and involves forming an imaging voxel (i-voxel) using the overlap between the X-ray beam(s) and the solid angle(s) within which X-rays can be detected by the X-ray detectors, which may be equipped with, for example, highly collimated apertures.

Further, the present disclosure is based, at least in part, on Applicant's discovery of a treatment method to deliver concentrated doses of X-rays to a treatment voxel (t-voxel) within a sample, with or without the use of nanoparticles. For example, for X-rays in the range of 40 to 60 keV and without the use of nanoparticles, the dose within the t-voxel may be more than 150 times the highest dose elsewhere in the sample, including that of X-rays at the surface of the sample. When enhanced absorption of X-rays by nanoparticles and subsequent enhancement of energy deposition are taken into consideration, the overall enhancement may reach 405 times or higher. For example, for X-rays between 80 and 100 keV, the enhancement may be 358 and 511 times without or with uranium nanoparticles, respectively.

The imaging and treatment methods of the present disclosure may be used alone or in combination. The methods may allow for the detection of internal structures in the interior of samples and/or the triggering of changes in the sample. Such changes in the sample may include, for example, charge transfer, oxidation or reduction, polymerization, cell killing and other responses in the samples, particularly to targets inside the samples.

Imaging Systems and Methods

The present disclosure provides systems and methods for providing irradiation energy to a sample followed by imaging and detection of X-ray fluorescence from a volume in the sample. The present disclosure relates to nanoparticle assisted X-ray fluorescence imaging, or NAXFI. In some embodiments, this imaging method may be performed using components such as, for example: 1) an X-ray source, 2) filters and apertures for the X-ray sources, 3) a sample stage, 4) X-ray detector(s), and 5) apertures for the X-ray detectors. In some embodiments, X-rays emitted from the X-ray source travel through a set of filters and an aperture before they reach a sample, which may be mounted on an XYZ motion stage. One or more detectors equipped with detector apertures detect both X-ray fluorescence emitted from nanoparticles associated with a target illuminated by the X-rays, as well as detecting scattered X-rays emitted from the sample. These scattered X-rays form the background or noise, whereas the fluorescent X-rays constitute the signal. The detector aperture limits the detection to a small solid angle of X-rays emitted from the sample and the target. This solid angle detector cone intercepts with the X-ray beam cone in space to form the imaging voxel (i-voxel). When the diameters of both cones at the target are small, i-voxel can be viewed as point of interest (POI). 3D images of the target in the sample may be formed by scanning the i-voxel/POI through the sample. As a result, this method is a point scan method, as opposed to a tomographic or sectioning method. Additional embodiments and features of the imaging methods and systems of the disclosure are described herein.

X-ray beams irradiated from an X-ray source have a defined cross-section. Further, paths of detection, in which an aperture is configured to define the path of detection from an irradiated sample to a detector, also have a defined cross-section. In some embodiments, an i-voxel is formed by the area of intersection of the defined cross-section of one or more X-ray beams irradiating a sample and the defined cross-section of the path of detection. Scanning an i-voxel with a detector and processing the detection information may allow for the detection of a target in the sample.

In some embodiments, multiple i-voxels are scanned to detect reflected X-ray fluorescence in each of the scanned i-voxels. For example, a first i-voxel may be scanned to detect the reflected X-ray fluorescence from this first i-voxel, and then a second i-voxel adjacent to the first i-voxel or otherwise located elsewhere in the sample at a location different from the first i-voxel may be scanned to detect the reflected X-ray fluorescence from this second i-voxel. Comparing the detection of reflected X-ray fluorescence in each of multiple i-voxels may be performed to gain information about the location of a target in the sample. For example, when the sample is an animal patient suspected of having cancer, scanning multiple i-voxels in the patient and comparing the respective detected reflected X-ray fluorescence from the multiple scanned i-voxels may allow for the detection of a cancerous region in a specific location in the patient. Scanning a single i-voxel and detecting the reflected X-ray fluorescence may also allow for the detection of a target, such as cancer, in a sample.

Treatment Methods

The present disclosure further provides methods of delivering irradiation energy to a sample. In some embodiments, the methods involve delivering a large dose of X-rays to a treatment voxel (t-voxel) by quickly rotating the X-ray beam(s) around a target, which acts as the isocenter of the rotation. In other words, the t-voxel is a volume that contains the isocenter. The isocenter is irradiated with one or more X-ray beams from at least three angles in a manner such that the isocenter is irradiated from at least one angle that is out of plane with at least one plane formed by two other angles. The rotation may be on various trajectories including, for example, arcs or spherical caps. The rotation of X-ray beams about the isocenter may be three-dimensional. The dose enhancement of irradiation energy at the target may be several few hundred times or greater than anywhere else in the sample. In some embodiments where the sample contains nanoparticles, if the absorption of nanoparticles within the t-voxel is taken into consideration, then the type 2 physical enhancement as known in the art may reach 100,000 times or greater. Other enhancement mechanisms, such as chemical enhancement, may be activated with focused X-rays at the target and give rise to even higher enhancement factor, resulting in over 1,000,000 time dose enhancement. Additional embodiments and features of the treatment methods of the disclosure are described herein.

The treatment methods of the present disclosure allow for greater deposition of irradiation energy at a t-voxel as compared to the deposition of irradiation energy at locations in the sample other than the t-voxel. Generally, during X-ray irradiation of samples, X-ray irradiation energy becomes attenuated after first contacting a surface of the sample and as the irradiation energy travels through the interior of the sample. The treatment methods as described herein use scanning focusing of X-ray irradiation at a t-voxel in the sample to focus and thus increase X-ray irradiation energy deposition at this location to reduce the impact of attenuation. In some embodiments, a greater amount of irradiation energy is deposited at a t-voxel as compared to the deposition of irradiation energy at a volume having equivalent volume to the t-voxel and located adjacent to a surface in the sample. In other words, the t-voxel in the interior of the sample is receiving greater intensity X-ray irradiation as compared to an equivalent volume near a surface of the sample, as opposed to the t-voxel in the interior of the sample receiving the decreased intensity/attenuated X-ray irradiation energy as compared to a volume adjacent to a surface of the sample first contacted with the irradiation energy. Using the treatment methods as described herein, irradiation of the isocenter should occur for a period of time sufficient to result in the t-voxel receiving increased irradiation energy deposition as compared to the energy deposition at a volume having equivalent volume to the t-voxel located adjacent to a surface of the sample.

When comparing X-ray irradiation deposition at a location in the sample other than a t-voxel, such as a volume adjacent to a surface of the sample, to the deposition of X-ray irradiation at a t-voxel, the volume being compared to the t-voxel should have equivalent volume to the t-voxel for accurate comparison of energy deposition per equivalent unit volume. In some embodiments, the t-voxel is a volume in the sample within which the local irradiation energy dose is at least 50% of the maximum peak irradiation energy dose in the sample. In some embodiments, a t-voxel may be considered as a point or spot when it is small enough.

Combination Imaging and Treatment Methods

The present disclosure provides imaging systems and methods for providing irradiation energy to a sample followed by imaging and detection of X-ray fluorescence from a volume in the sample. Further, the present disclosure provides treatment methods of delivering irradiation energy to a sample. While the imaging methods and the treatment methods of the present disclosure may be used independently, in some embodiments, an imaging and treatment method of the present disclosure may also be used in combination.

In one embodiment of a combined method, an imaging method as described herein is performed before performing a treatment method as described herein, in which case the treatment method is performed after the imaging method. In one embodiment, an imaging method as described herein is used to identify a target in a sample followed by using a treatment method as described herein to deliver irradiation energy to the target in a sample. For example, the combination of the point scan imaging using the formation of an i-voxel followed by focused irradiation dose delivery with a spherical cap motion of the X-ray source, as well as the use of nanoparticles to enhance the absorption of X-rays in a t-voxel, may be used as a multiple faceted, complete cancer diagnosis and treatment approach.

In one embodiment of a combined method, a treatment method as described herein is performed before performing an imaging method as described herein, in which case the imaging method is performed after the treatment method. In one embodiment, a treatment method as described herein may be used to deliver irradiation energy to a target in a sample followed by using an imaging method as described herein to identify the target in the sample. Imaging the sample after treatment may be used, for example, to inform the efficacy of the treatment. For example, the combination of irradiation energy delivery treatment to a t-voxel to treat a sample, such as a cancer patient, followed by imaging of an i-voxel in the sample to identify the target may be used as a combinatorial approach to cancer treatment and subsequent monitoring of cancer progression and/or efficacy of treatment.

Tools for Imaging and/or Treatment Methods and Systems

The present disclosure provides various tools for use in the imaging and/or treatment methods and/or systems. In some embodiments, the tools may be used in the imaging methods and/or systems of the present disclosure. In some embodiments, the tools may be used in the treatment methods of the present disclosure. In some embodiments, the tools may be used in both the imaging and/or treatment methods and/or systems. One of skill in the art would readily recognize modifications as well as additional tools and/or features that may be used in the imaging and/or treatment methods and/or systems of the present disclosure.

X-Rays and Irradiation Energy Deposition

The imaging and treatment methods and/or systems of the present disclosure involve delivering X-ray irradiation to a sample. In some embodiments, X-ray focusing optics may be used to shorten the imaging time and increase the local X-ray dose in the treatment mode. In some embodiments, use of a rotating anode microfocus X-ray sources may be employed to shorten the imaging time.

Various X-ray sources and operation parameters are known in the art, are described herein, and may be used in the methods of the present disclosure. The operation voltage may be in the region of 30 to 150 keV and may further be selected based on the elemental composition of the targeting nanoparticles. Filters in front of the X-ray source(s) may be used to control the X-ray spectrum entering the sample. For example, for nanoparticles composed of Ag, 40 kVp may be used. For nanoparticles composed of Au, 100 kVp may be used.

Various X-ray detectors and apertures are known in the art, are described herein, and may be used in the methods of the present disclosure. The X-ray detectors may be an array of single element X-ray detectors such as, for example, CZT detectors from Amtek. The X-ray detectors may be equipped with highly collimated apertures. The apertures may be made of lead and shielded further by copper. The dimension of the aperture in front of the detectors may have 1.5 mm height at the end of the sample and 5 mm height at the detector end and a total length of between 3 to 30 cm.

In some embodiments, the overall irradiation dose deposited in the sample, such as water or a human sample, is less than 0.06 rem for scanning a cube of sample of 1 cm sides. It may take less than 10 rem to scan a cube of sample of 10 cm sides. The scan time may be less than 16 ms per point and 16 sec for a 1-cm side cube using one beam and one ring of detector configuration with a 50-W microfocus X-ray source.

The increase or enhancement in the deposition of irradiation energy may include an increase in the deposition of energy that is, for example, about a 2-fold increase, about a 4-fold increase, about a 6-fold increase, about an 8-fold increase, about a 10-fold increase, about a 15-fold increase, about a 20-fold increase, about a 30-fold increase, about a 40-fold increase, about a 50-fold increase, about a 60-fold increase, about a 70-fold increase, about an 80-fold increase, about a 90-fold increase, about a 100-fold increase, about a 120-fold increase, about a 150-fold, about a 200-fold increase, about a 250-fold increase, about a 300-fold increase, about a 350-fold increase, about a 400-fold increase, about a 450-fold increase, about a 500-fold increase, about a 550-fold increase, about a 600-fold increase, about a 650-fold increase, about a 700-fold increase, about a 750-fold increase, about an 800-fold increase, about a 900-fold increase, about a 1,000-fold increase, about a 1,200-fold increase, about a 1,400-fold, about a 1,600-fold increase, about an 1,800-fold increase, or about a 2,000-fold or more increase in deposition of irradiation energy.

Nanoparticles

The sample of the present disclosure may contain one or more nanoparticles. The nanoparticle may be a metal-based nanoparticle where the nanoparticle is composed, at least in part, of a metal. Various nanoparticles are known in the art and may be used in the methods described herein. For example, these nanoparticles may include silica nanoparticles, silica-coated gold nanoparticles, silica-coated silver nanoparticles, tungsten oxide nanoparticles, titanium nanoparticles, rare earth nanoparticles such as cerium oxide nanoparticles, and other biocompatible nanoparticles such as dendrimers and polymers. Further, nanoparticles may be composed of an organic material, an inorganic material, or a combination of an organic material and an inorganic material. In some embodiments where the nanoparticles are composed, at least in part, of a metal, the metal may be, for example, silver (Ag), gold (Au), and/or uranium (U).

The sizes of the nanoparticles may vary. For example, the size of the nanoparticle may range from 1 nm to 300 nm. Note that the dimensions of the nanoparticle may vary and other dimensions may be used in the nanoparticles described herein, including nanoparticles with dimensions less than 1 nm and nanoparticles with dimensions greater than 300 nm. The nanoparticles may have a dimension of about 15 nm. The nanoparticles may have a dimension of about 50 nm. The nanoparticles may have a dimension of about 100 nm.

Samples

The methods of the present disclosure involve a sample to be used in the methods described herein. Various samples for use in the methods of the present disclosure will be readily apparent to one skilled in the art and are described herein. The sample may be, for example, a subject in need of a treatment, such as a cancer patient. The sample may also be, for example, a living system such as a living tissue, organ, or organism. One of skill in the art will readily recognize additional types of samples for use in the methods of the present disclosure.

EXAMPLES

To better facilitate an understanding of the embodiments of the disclosure, the following examples are presented. The following examples are merely illustrative and are not meant to limit any embodiments of the present disclosure in any way.

Example 1

Nanoparticle Assisted Three Dimensional Point Scan X-Ray Fluorescence Imaging

This Example describes an X-ray imaging method with the assistance of X-ray fluorescent nanoparticles. X-ray fluorescence emitted from nanoparticles irradiated with a thin beam of X-rays is detected by X-ray detectors with individual small solid angle apertures. Such a combination of excitation and detection defines a small imaging voxel (i-voxel) from which X-ray fluorescence is exclusively detected at a time. The energy dispersive detectors can further select only those X-ray fluorescent photons from the nanoparticles as signal, rejecting scattered X-rays by the background material such as tissues in an i-voxel. Three-dimensional images or profiles of the nanoparticles in the sample can be formed by scanning the i-voxel through large-volume samples, such as the human body. This method is more sensitive than any existing CT methods, and bears higher spatial resolution than conventional PET, SPECT, and other imaging methods. The method may be used, for example, as an imaging tool designated to detecting small tumors and early stage cancers.

Introduction

This investigation explores methods to probe minimal amounts of nanoparticles in small targets embedded within a large body of background water, which is close to the density of human tissues. The approach described here is based on detecting X-ray fluorescence from nanoparticles excited with a small diameter beam of X-rays with X-ray detectors equipped with small solid angle apertures. The improved resolution and sensitivity derives from guided detection by the apertures in front of the X-ray detectors and the limited excitation of the samples with the thin incident X-ray beam. The use of gold, silver and 238U nanoparticles in water phantoms is explored; Au is biologically benign, Ag offers high sensitivity when studying small samples, and although 238U is radioactive, small amounts (micrograms) of 238U is hardly toxic due to the long half-life and high natural abundance. Uranium is a heavy element that can be used to make nanoparticles to facilitate the detection of nanoparticles deep in the sample.

This method of using nanoparticles to assist the imaging of small tumors in the body with X-rays is called nanoparticle assisted X-ray fluorescence imaging, or NAXFI. In the following, it is described how to detect small targets (1-2 millimeters in dimension) of small amounts of nanoparticles (10-30 µg) in large (5-15 cm) water phantoms.

Methods

The principle of the new imaging tool, as well as the instrumentation and simulation process, are described herein.

NAXFI Principle

The working principle of the instrument is shown in FIG. 1. The instrument contains 5 major components, as shown in FIG. 1A: 1) X-ray source 2) Filters and an aperture(s) for the source(s) 3) Sample stage 4) Detector(s) and 5) Aperture(s) for the detector(s). X-rays emitted from the X-ray source pass through a set of filters and an aperture before reaching the sample, which is mounted on the XYZ motion stage. One or more detectors equipped with the apertures can detect both X-ray fluorescence emitted from the nanoparticles and scattered X-rays emitted from the sample irradiated by the X-ray beam. These scattered X-rays constitute the background or noise, whereas the fluorescent X-rays are the signal. Each detector aperture limits the solid angle through which X-rays can be detected (detector cone in FIG. 1B). This solid angle intercepts with the X-ray beam (X-ray cone) in space to form an imaging voxel (i-voxel). When dimensions of an i-voxel are small, this voxel can be viewed as point of interest (POI). 3D images can be formed by scanning the i-voxel through the sample while detecting the fluorescence. As a result, this new approach is a 3D point scan, not a tomographic or sectioning imaging method. Such a detection method enables high sensitivity probe of the target in the sample, which can be much higher than CT based methods due to significant reduction of the number of scattered X-ray photons entering the detector(s).

In this method, the transverse resolution (X and Y direction perpendicular to the X-ray beam) is defined by the convolution of the dimension of the X-ray beam and the opening of the detector aperture cone in the X/Y direction. Because the diameter of the X-ray beam is generally smaller than the dimensions allowed by the acceptance solid angle of the detector aperture, the overall transverse resolution is normally determined by the X-ray beam diameter. There is negligible X-ray scattering from samples beyond that outlined by the excitation of the X-ray beam whose size is defined by the size of the aperture in front of the X-ray source. The axial resolution (Z direction) is defined only by the opening of the detector aperture (detector cone) in this direction, as shown in FIG. 1B. The dimension of the aperture in front of the detector can be made so that the detector will observe or detect an area comparable to that of the X-ray beam at the target.

A target in this Example is a 3D region loaded with X-ray fluorescent nanoparticles. In this case, the target was a 1-mm thick, 1-mm radius cylindrical disc (FIG. 1B). The nanoparticles of various concentrations are uniformly deposited in this disc, which resides in the sample.

3D imaging of the target in the sample can be obtained by scanning the i-voxel throughout the sample. Practically, i-voxel can be scanned through only parts of the sample, likely those that have nanoparticles taken up by the tumor. In a typical case, regular computed tomography (CT) scan may be used to examine the whole sample, followed by NAXFI of the suspicious regions. No reconstruction is needed for NAXFI because signals from the detectors can be directly used to form images when they are coded with coordinates of the i-voxel.

If multiple detectors are used, the apertures for these detectors can aim at the same i-voxel, which is the focus of these detectors. In addition to one X-ray beam and one focus configuration (FIG. 1B, FIG. 1F, FIG. 2A), other configurations of using multiple detection foci to simultaneously detect different spots along the path of one or more X-ray beams are possible. For instance, it is possible to use 3 beams (3B) with a set of detector apertures aiming at three foci (3F). This is the 3B/3F configuration, as shown in FIG. 2B. Only one focus is shown through. It is also possible to use 3 sets of detector apertures, each focusing at a different i-voxel, therefore creating three foci (3F) to simultaneously detect 3 i-voxels along one X-ray beam (1B), as shown in FIG. 2C (1B/3F). Another configuration is simultaneously detecting X-ray fluorescence from 9 spots excited with 3 X-ray beams (3B/9F), which is shown in FIG. 2D. A generic configuration using a matrix of the number of X-ray beams and the number of aiming of the detector apertures can be employed to predict how these arrangements can shorten the imaging time.

Simulation

This simulation uses the configuration shown in FIG. 1 and FIG. 2A (1B/1F) because the other three can be extrapolated from the results of 1B/1F after minimal adjustments. In the simulation, a beam of X-rays is sent into the sample. The X-ray photons are scattered or absorbed by the sample or the target containing nanoparticles. A chart illustrating exemplary simulation steps is provided in FIG. 9. Briefly, the simulation contains four parts, as described below. The first part tracks the X-ray photons traveling in the sample, and determines the end points which can be absorption of the photon, scattering of the photon, or exit of the photon from the sample. The second part deals with how X-rays interact with nanoparticles. In the third part, the scattered and fluorescent photons are tracked to determine if they enter the detector. Finally, targets in the sample are mapped by scanning the beam of incoming photons while detecting the X-ray fluorescence.

Figure 9B:
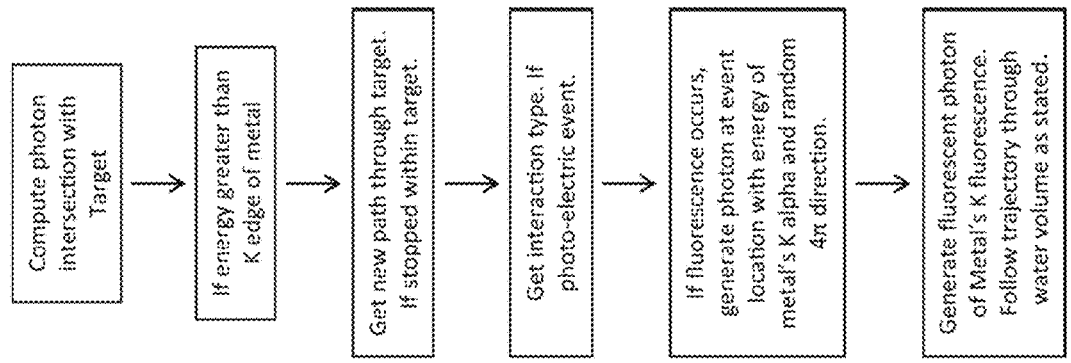
FIGS. 9A-FIG. 9B illustrate the flow chart of the simulation of interactions of X-ray photons with water in the cubic sample and a nanoparticle target in the sample. The target is a disc of 1-mm diameter and 1 mm in height, filled with aqueous solution of nanoparticles.
Figure 9A:
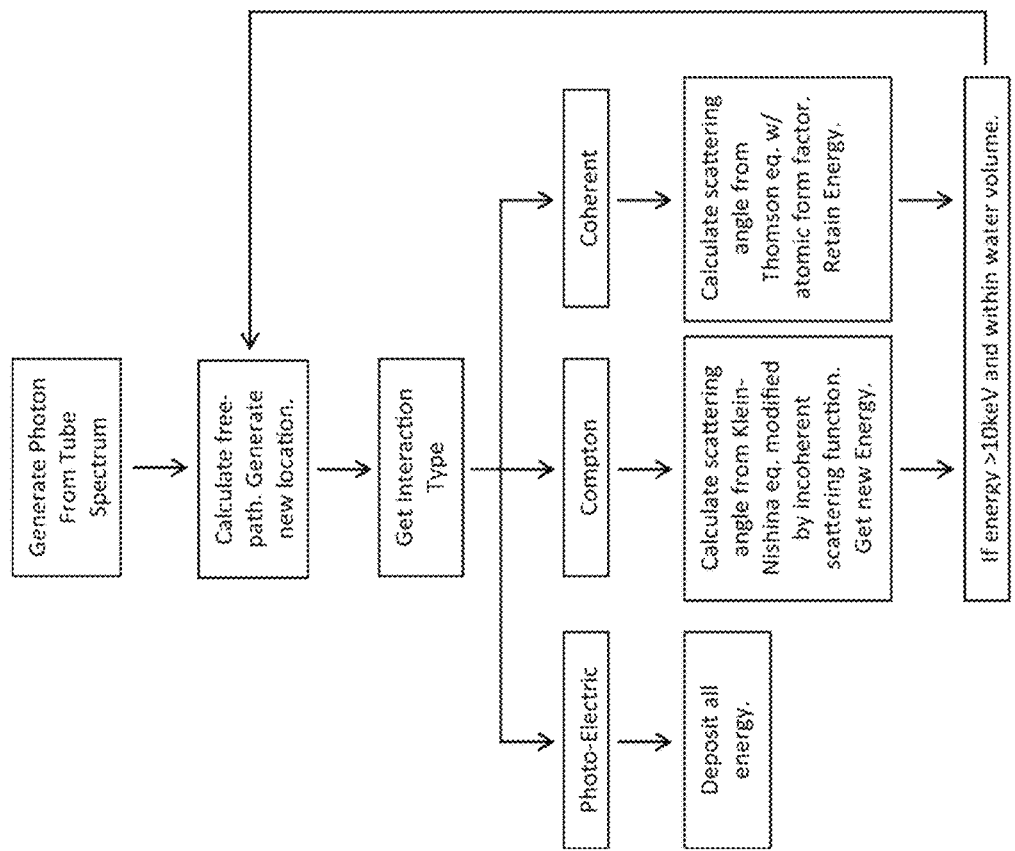

Each photon entering the sample is simulated by tracking it in the sample. FIG. 9A shows the simulation of photons interacting with water alone and FIG. 9B shows that with the nanoparticles alone. In each of the two simulations, the program tracks the X-rays photons in the sample, determining the end point, whether it is absorption of the photon, scattering of the photon, or exit of the photon from the sample. If the photons enter the target region, then the program makes similar differentiations, except that X-ray fluorescent photons from nanoparticles are obtained and their trajectories are used to calculate the detection of nanoparticles. Targets in the sample can be mapped by scanning the beam of incoming photons while detecting the X-ray fluorescence.

Interaction of X-Rays with the Sample

As shown in FIG. 1, the X-ray beam irradiates the sample with targets inside. In the simulation, each X-ray photon starts at the edge of the sample, aiming inside. The starting position of each X-ray photon is a random position within the X-ray beam traveling in the Z direction (x, y, 0, 0, 0, E). $10^6$ photons are used to represent a given spectrum and are used in all the cases. X-rays can either be absorbed or scattered by atoms in the sample or target. Once a photon starts the simulation journey, it is tracked through the whole sample (e.g., a 10×10×10 cm cube of water). To track a photon, the sample media (water) is specified and a random free path is calculated from the photon current energy (Chan, H. P. and K. Doi, Physics in Medicine and Biology, 1983, 28(2): p. 109-129). The next location is determined by the calculated free path and the new location is given (x, y, z, θ, φ, E). At this new location, the type of interaction (photoelectric, Compton, or coherent) is determined from their relative probabilities (National Institute of Standards and Technology). If interaction type is photoelectric, the energy of the photon is deposited and the photon tracking ends. If the interaction type results in Compton scattering, the scattering angle θ is calculated using the Klein-Nishina formula modified by the incoherent scattering function (Chan, H. P.

and K. Doi, Physics in Medicine and Biology, 1983, 28(2): p. 109-129; National Institute of Standards and Technology; Hubbell, J. H et al., J. Phys. Chem. Ref. Data, 1975, 4(3): p. 471-493). The scattering angle then determines the energy loss of the scattering event using Compton's formula (Compton, A. H., Physical Review, 1923, 22(5): p. 0409-0413). If the interaction event is coherent the photon retains the equivalent energy and the new scattering angle $\theta$ is predicted using the Thompson equation. In both Compton and coherent scattering events, the angle $\varphi$ is sampled randomly. Photons are tracked in this fashion until a photoelectric event occurs, or the photon's energy is less than 10 keV, or the photon exits the water cube sample. Because 10 keV X-ray photons are significantly attenuated in water, it is assumed that these photons will deposit 100% of their energy within 100 microns of water.

Interaction of X-Rays with the Target

The target is considered as a uniform mixture of the elements of interest and water. Once a photon enters the volume or space of the target, it is evaluated for causing photoelectric effect by the elements. A mean free path is determined based on the density and type of the elements in the target volume. If the free path is less than the path length of photon in the target, the interaction type is determined at that location. If the interaction type within the object is photoelectric, a fluorescent photon is created with the characteristic K line energies of the target element and tracked through the water medium until a photoelectric event (with oxygen, as stated in the previous section) occurs or the photon exits the boundaries. The fluorescence simulation compiles a list of trajectories of individual photons for all the fluorescent photons.

Photon Detection by the Detector

The photon and fluorescence lists created from the above-mentioned interactions are searched to determine if any trajectory of scattered or fluorescent photons passes through both the front and back planes of the detector aperture. The search result returns the intersection points and energies of the photons on both the front and back plane of the aperture. The detector is positioned behind the back aperture plane, so any photon going through the aperture is detected. A histogram of the photons in the energy bins of 150-eV width produces the simulated signal.

Image Formation

The sample, together with the target inside, is rastered by the XYZ motion stages while the detectors collect the X-ray photons. Each detector is equipped with a multichannel analyzer and the processed signals are sent to the computer. The energy resolution of the detector is 150 eV. The fluorescent X-ray photons at specific energy will be recognized against the background scattered X-ray photons, which have an almost flat energy spectrum at the energy of the fluorescent photons. Signal is obtained by subtracting the background.

Multiplicity of X-Ray Beams and Detectors

Although simulation of the multiple X-ray beams and detector foci and their combinations is not performed here, it is thought that similar results for those configurations as the single X-ray beam and single array of detectors would be observed although their designs are more challenging with regard to multiple foci detector rings due to the need to avoid cross detection of fluorescence from targets at different foci.

Results

As X-rays travel from the source to the sample and through it, the energy spectrum changes or as low energy X-rays get absorbed or scattered more than the higher energy or hard X-rays. To maximize the fluorescence yield, different initial X-ray spectra are created by different X-ray filters to excite different elements in the target at above their absorption K edges. FIG. 3 shows the spectral evolution of three initial X-ray spectra for investigating three target elements: Ag (K edge at 25.1 keV), Au (K edge at 81.7 keV) and U (K edge at 97 keV). FIG. 3A shows the spectra for detecting Ag in water as a function of position, from the source to the target in the middle of a 5-cm cube of water. The voltage of the X-ray tube is set to 40 kVp. FIG. 3B and FIG. 3C show those for Au and U, which are operated at 100 and 130 kVp. The X-ray filters are different in these three cases.

Figure 4B:
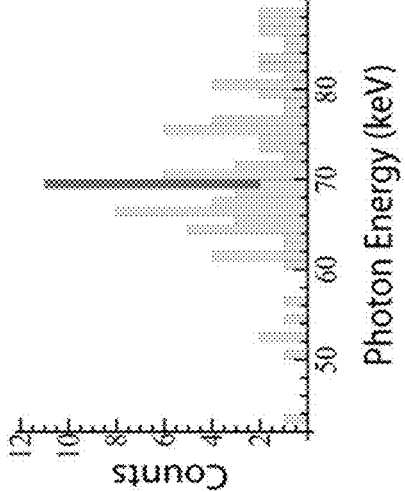
Figure 4A:
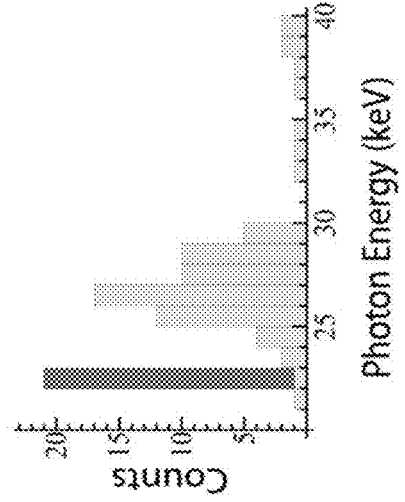

Once the X-rays are absorbed by the atoms in the target (Ag, Au, or U) or scattered by the atoms in the sample (O), they may be detected by the detector. The simplest configuration is a single X-ray beam irradiating a sample with a single target detected by an array of detectors with their apertures aiming at the target (one focus), as showing in FIG. 2A. The diameter of the X-ray beam is 2 mm. 1 wt. % of Ag in a 1-mm tall and 1-mm radius disc target is inserted in a 5 cm water cube. 163 detectors are employed for detecting Ag uniformly positioned on a 15-cm radius circle whose plane perpendicular to the X-ray beam. Each detector has an active area of 5×5 mm$^2$ and is equipped with an aperture aiming at the target. The front opening of the aperture has a 1.75 mm height and the back 5 mm. The length of the aperture is 5 cm. The dimension of the aperture controls the axial spatial resolution while the X-ray beam diameter controls the transverse resolution. FIG. 4 shows the energy spectra of the photons detected by the detectors in the three cases described in FIG. 3. The darker gray colored bars represent the fluorescent photons and light gray ones represent scattered photons that hit the detectors on the ring. The amount of nanoparticles is 31 μg in all three cases. The detected X-ray fluorescence is 24% (26 out of 208) of the total photons hitting the detector (see Table 1); the rest being scattered photons. For detecting Au fluorescence from the same dimensioned target in the middle of a 10-cm side cube with 195 detectors, the percentage of X-ray fluorescence from the target drops down to 12% of the total photons detected. It is difficult to detect U fluorescence from the target in the middle of a 15-cm cube. Even with 226 detectors, the percentage is only 4%. These numbers are listed in Table 1.

Imaging the target can be achieved by moving the sample (point by point) with respect the X-ray beam and detectors, or vice versa. FIG. 5 shows the simulated results for detecting the Ag, Au, and U targets in the cubic samples. In the lower left panel, the whole sample and X-rays are shown. White trajectories represent that of incoming/exciting X-rays and gray ones represent the scattered X-rays by water. Yellow trajectories show that of fluorescent X-rays from the nanoparticles. The upper left panel shows a contour plot of the image of the target in the sample, and only a small volume of the sample is shown. Contour profiles in 2D are shown in FIG. 5B-5D and FIG. 5F-FH. The number of photons or signals in these panels are normalized to that of FIG. 5B (axial view) or FIG. 5F (transverse view), which shows the Ag target in 5-cm cube. FIG. 5C and FIG. 5G show the images of the Au target (1 wt. % in the disc) in 10-cm side cube. The target is clearly seen, but signal-to-noise ratio (S/N) is lower. For U case in FIG. 5D and FIG. 5H, weak signals from the target are indicated. White dashed lines show the profile of the targets in the sample. From FIG. 5 it is clear that this point scan fluorescence imaging is many times more sensitive that those used in various XFCT studies when comparing the sensitivity of the total amount of nanoparticles detected.

As explained above, the transverse resolution (X and Y directions) is defined by the convolution of the X-ray beam and the opening of the aperture in the X/Y direction. The axial resolution is defined by the vertical opening of the aperture. In the simulated case using Ag nanoparticles, the axial resolution of the aperture is 1.3 mm in the vertical direction, which translates to 1.3 mm axial resolution. The radial resolution is defined by the X-ray beam, which is 2 mm diameter. FIG. 6 shows two targets separated by 3 (gap between targets) and 2 mm. It is clear that the targets separated by 2 mm are discernible.

Figure 7A:
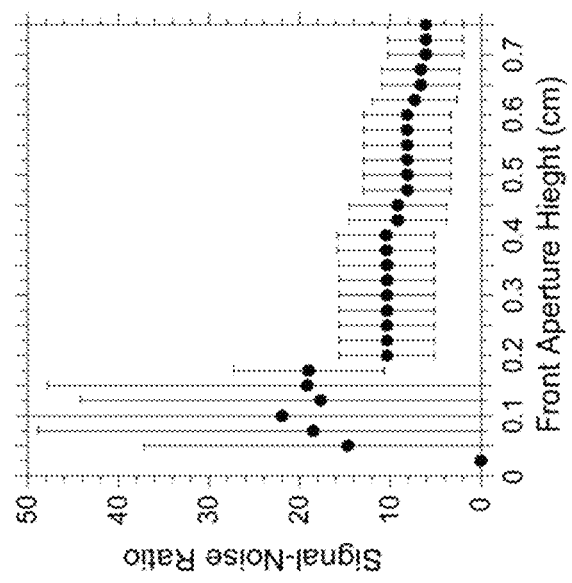
FIGS. 7A-FIG. 7C illustrate the signal to noise ratios in three experimental situations.
Figure 7B:
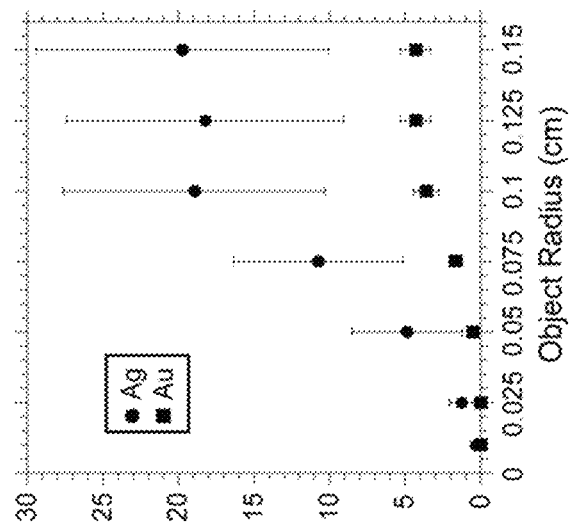
Figure 7C:
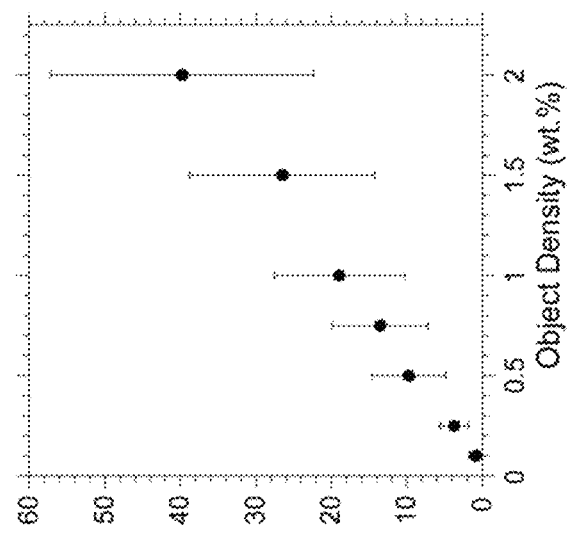

These results show that it is possible to image small amounts of nanoparticles in a single small volume in the body. The potential of the new imaging tool can be further estimated as follows. Several parameters directly influencing the noise levels are shown in FIG. 7. FIG. 7A shows the S/N for detecting 0.5 wt % Ag in 1-mm cube located in a 5-cm water cube as a function of the solid angle through which the detector can detect X-ray photons, which in this case is the height of the front opening. As shown, too small an opening limits the signal, which leads to large fluctuation in S/N. Large openings will allow more scattered photons to be detected, increasing the noise and reducing S/N as well. FIG. 7B shows the dependence of S/N ratio as a function of the target size for a fixed X-ray beam size. It shows that S/N decreases as the target size decreases due to the reduced signal while the noise is kept approximately constant. This means it is critical to keep the beam size comparable to the smallest target size so to keep the noise low and spatial resolution high. Ag in 5-cm phantom produces higher S/N than Au of the same weight percentage in a 10-cm phantom. FIG. 7C shows the dependence of S/N ratio as a function of the weight percentage of the target in a fixed volume. A linear relationship is shown.

As the diameter of the incident X-ray beam becomes larger, the time taken to scan the sample is shortened. However, the sensitivity also decreases. If the size of the target remains the same, S/R decreases as the size of X-ray beam increases. Unless there is proportionally more target material in the X-ray beam, increasing the size of the beam will always decrease the sensitivity while speeding up the scan time. This is why both thin X-ray beams and the guided detection are important to achieving simultaneous high sensitivity and resolution.

Table 1 summarizes the parameters used and results generated in the simulation. It shows the flux of X-ray beam at the entrance of the sample (fifth row). $10^6$ photons are used in each simulation and the numbers of photon at the target locations are shown. It also shows the total numbers of scattered and fluorescent X-rays as well as the detected fluorescence and scattered X-ray photons. The number of detectors and time taken to detect the nanoparticles are shown. The times are calculated based on the listed incoming X-ray flux. The reason for the longer imaging time in the Au case is due to the low flux of the incoming X-rays caused by stronger filtration. X-ray dose for each point acquisition and overall dose for the imaging are given. The dose is calculated based on the average dose (absorbed energy over the whole irradiated volume). Because the scan is done with overlapping X-ray beams, the average dose of a scan is greater than the single expose, but less than the simple summation of all the single exposures needed for the scan. A 2D sectioning scan of a whole cross section of the samples similar to CT using the same X-ray source takes approximately 5.3 sec, 600 sec, or 137 sec for Ag in 5-cm, Au in 10-cm, or U in 15-cm sample. The respective doses are 12 mGy, 25 mGy, or 55 mGy. It is possible to quickly move the X-ray beam while aiming the beam at the i-voxel so that the beam focuses at the i-voxel. This can significantly reduce the dose at the entrance, possibly by one to two orders of magnitude.

TABLE 1

Summary of Calculations

| Parameter for each Element of Metal in Nanoparticles | Ag | Au | U |
|---|---|---|---|
| Sample Size (sides of a cube (cm)) | 5 | 10 | 15 |
| Target Size (disc, thickness × diameter (mm)) | 1 × 2 | 1 × 2 | 1 × 2 |
| Target Location in Sample (X, Y, Z (cm)) | (0, 0, 2.5) | (0, 0, 5) | (0, 0, 7.5) |
| X-rays at the Entrance (photons/s$^{-1}$) | $1.54 \times 10^9$ | $5.38 \times 10^7$ | $5.31 \times 10^8$ |
| Photons Used in Simulation | $1.00 \times 10^6$ | $1.00 \times 10^6$ | $1.00 \times 10^6$ |
| Photons at Target Location | $3.45 \times 10^5$ | $4.14 \times 10^5$ | $3.02 \times 10^5$ |
| Fluorescent Photons (Total) | 9680 | 2426 | 794 |
| Detected Fluorescent Photons | 26.3 | 8.67 | 2.33 |
| Detected Background Photons | 82 | 62 | 56 |
| Background Noise Average (+/−1 bins) | 1.60 | 3.60 | 1.00 |
| Number of Detectors | 163 | 195 | 226 |
| Time to Detect at Each Spot (ms) | 0.650 | 18.6 | 1.88 |
| 9 × 9 (cross-section) Imaging Time (s) | 0.053 | 1.51 | 0.153 |
| 3D Imaging Time (s) (9 × 9 × 11 array) | 0.58 | 16.57 | 1.68 |
| Average Dose per Point (water only) (μGy) | 12.1 | 6.08 | 6.03 |
| Average 2D Imaging Dose (μGy) | 123.5 | 61.9 | 61.4 |
| Estimated 3D Imaging Dose (μGy) | 226.3 | 113.5 | 112.5 |

Discussion

A clear advantage of this method is that it may help avoid the problem of having the partial volume effect associated with CT, which misclassifies small dense objects as large and less dense objects in a large sample, which could miss the opportunity to diagnose small tumors. Because the X-ray beam in NAXFI is small, it is unlikely to misclassify these two types of objects.

In the 1B/1D configuration, most of the X-rays entering the body are not used for excitation; only about 1% of the X-rays are used to excite the target. However, due to the smallness of the target, such limited excitation is necessary to maximize sensitivity. When the 1B/nF configuration is used, several percent or more X-rays are used to excite the targets. However, once again, if there is only a small target, then only a very small portion of the X-rays are used to excite the target. This is also true in regular CT; if a small target is sought, then the majority of the X-rays are not used to detect such a small target.

There are several similar but different approaches based on X-ray beams and apertured detectors, as discussed previously. Cho et al used both a pencil X-ray beam and wide apertured detectors, although not simultaneously (Jones, B. L et al., Physics in Medicine and Biology, 2012, 57(23): p. N457-N467). They used either a pencil beam and detector without apertures in front of detectors, or a broad beam with apertures in front of detectors to shorten imaging times. As a result, the resolution and sensitivity are lower and only 2D imaging is explored. Bazalova et al. employed fluorescent X-rays from targets in regular CT configuration, although multiple thin beams similar to microbeam arrays were used. No apertures are used (Bazalova, M et al., Ieee Transactions on Medical Imaging, 2012, 31(8): p. 1620-1627). Synchrotron X-ray beams are used and large area detectors with multiple apertures are also explored previously (Meng, L et al., Proc. of SPIE, 2010, 7804: p. B1-B9). The geometry and detectors are only suitable for low energy X-rays. These methods are developed toward increasing the scan speed using regular CT principles, but are not to raise the sensitivity or spatial resolution. In contrast to all of these methods, the approach described here represents the first time when X-ray beams and narrow detector apertures are used together to achieve the highest sensitivity and spatial resolution with slightly sacrificed scanning time and overall dose. Because only a small 3D volume is probed, the scan time and overall dose (seconds and mGy) are similar to regular CT, as shown in Table 1.

Because this is essentially a point scan technique, it is possible to image the sample in various manners, whether it is a line, a slice, or 3D mapping. The data acquisition time and dose for a full slice scan are similar to that of a regular CT scan. For a typical 50-W microfocus X-ray source, the imaging time for scanning through a 1-mm thick slice of 10-cm side sample with a 1-mm resolution to find a 10 μg Au target shown in FIG. 5 is about 10 min with the one-beam and one-ring detector configuration (1B/1F). Multiple X-ray sources or beams and multiple detectors and foci can be used to proportionally shorten the acquisition time. It is also possible to use more powerful rotating anode microfocus sources such as those from Regaku Inc., which can deliver over 1 kW X-rays per source. The overall dose for such a scan will be proportionally higher.

It is clear that the choice of elements of the nanoparticles is important. A clear understanding of the capability of the method is required to fully take advantage of the method. The dimensions of the sample and depth of the target depend on the choice of the nanoparticles as well. Generally speaking heavier elements allow deeper detection of targets in larger size samples. The limit of the detection is about micrograms for these nanoparticles. This reasoning can be further illustrated in FIG. 8, which shows the signal or fluorescent X-ray photons from different elements at different depths. FIG. 8A shows the relative fluorescent signals for three metals as a function of depth. It is the easiest to detect Ag in small samples of 2-3 cm in diameter. If signal is normalized to the number of incoming photons, then U is slightly better than Au as probing deep targets, as shown in FIG. 8B. Both Au and U are good to probe 10 to 15 cm deep targets.

Simulations of multiple spots/foci and multiple beams configurations were not examined. Due to the linearity of the X-ray absorption and detection, the results from multiple beams and foci can be extrapolated linearly from the results of single beam, single focus results. The detection time should decrease inversely proportionally as a function of the multiplication of the numbers of detectors and beams. Dose, on the other hand, should increase inversely proportionally to the number of detectors but proportionally to the number of beams.

As pointed out above, this method can complement regular CT by imaging only the troubled volumes with much higher sensitivity than CT. Conventional PET imaging with radioactive elements can be much more sensitive, but spatial resolution is sacrificed. Hence, fluorescence-based X-ray imaging will be advantageous for imaging small targets in very thick samples. In these situations, the transmission mode cannot provide enough S/N without overdosing due to strong absorption of X-rays by the whole length of the sample. Instead, X-ray fluorescence only needs to travel less than half of the length of the sample to be detected, therefore providing much higher quality imaging given the same dose.

Conclusions

These experiments have demonstrated that it is still difficult to detect standalone millimeter sized 3D targets in large 3D samples even with the assistance of nanoparticles and fluorescence-based CT. Nonetheless, employing nanoparticles can potentially increase the sensitivity of tumor diagnosis so that it is possible to detect small, millimeter sized tumors in the body. Generally speaking, 1 wt. % AuNPs or AgNPs can be delivered to or taken up by the tumor, and if we expect to find 1-mm cubic sized tumors then we need to detect 10 μg of nanoparticles. This is almost an order less than the minimum amounts of what have been tested in the fluorescence X-ray CT experiments mentioned above.

Meeting the imaging and detection requirements may not only satisfy the need to detect small changes in the body, but also help track down nanoparticles entering the ecosystem. For example, it is important to know the amount of nanoparticles in the lung of mice, which is of the order of 100 μg in a 1-cm cube, and the spatial resolution should be of the order of sub-millimeters. These requirements are more stringent than what are needed for imaging nanoparticles in human as mentioned above.

Overall, this Example describes an X-ray imaging modality with the assistance of X-ray fluorescent nanoparticles. The spatial resolution can be higher than 1 mm, and the minimum amount of nanoparticles can be less than 10 μg or 0.33 wt. %. The size of the sample can be 15 cm or larger. This new method is many times more sensitive than any existing CT methods, and has much higher spatial resolution than conventional PET, SPECT and other imaging methods. It may be used as a complementary imaging tool to these other imaging methods to detect small tumors and early stage cancers.

Example 2

Nanoparticle Assisted Scanning Focusing X-Ray Therapy

This Example demonstrates that three-dimensional scanning of an X-ray beam or beams going through a fixed point or isocenter in a sample can increase the dose in the treatment voxel (t-voxel) near the isocenter over that at the surface, and the magnitude of increase depends on the beam size, scanning geometry, X-ray energy, the composition and size of the sample, and the location of t-voxel. Such scanning creates a three-dimensional focusing effect for the X-rays. In one instance, more than 185-fold dose enhancement over that at the surface is predicted within a 1-mm cubic target located 5 cm deep in water irradiated with a 1-mm diameter X-ray beam emitted from a tungsten X-ray source operated at 60 kPv. The shape of the enhanced volume (i.e. t-voxel) without the nanoparticles is an oblate spheroid, with the longer axis in the axial direction of the scanning focusing X-rays. Adding X-ray absorbing nanoparticles in the t-voxel further increases the enhancement. For example, dose enhancement with 1 wt. % gold nanoparticles in the t-voxel increases by more than 2 fold over the scanning enhancement. Overall, there is a 405-fold increase in dose in the nanoparticle-targeted t-voxel. The dose enhancements are 358 and 511 times for 110 kVp X-rays without and with the use of the uranium nanoparticles, respectively. The enhancement volume adopts the exact shape of the nanoparticles.

Introduction

The present Example explores how to improve the enhancement of the dose of X-rays delivered to a target deep in the body with respect to that at the skin using 50-120 keV X-rays. The focus is on studying the geometric configuration of the motion of the X-ray source that allows us to deliver maximum dose at the target. Furthermore, nanoparticles were added into the target volume to study how they influence dose enhancement. As mentioned above, there are several types of enhanced absorption and energy deposition reported in the literature (Lee, C et al., J. Phys. Chem. C, 2012, 116(20): p. 11292-11297; Carter, J. D et al., J. Phys. Chem. B, 2007. 111(40): p. 11622-11625). This Example focuses on the average or remote dose enhancement, which is called type 1 physical enhancement or T1PE. This will give rise to minimal enhancement by the nanoparticles over a macroscopic volume. If nanoscale or local enhancement is included, much higher enhancement may be obtained. However, this latter type of enhancement will not be discussed here.

Experimental/Simulation

Dose Enhancement Principle

Figure 10:
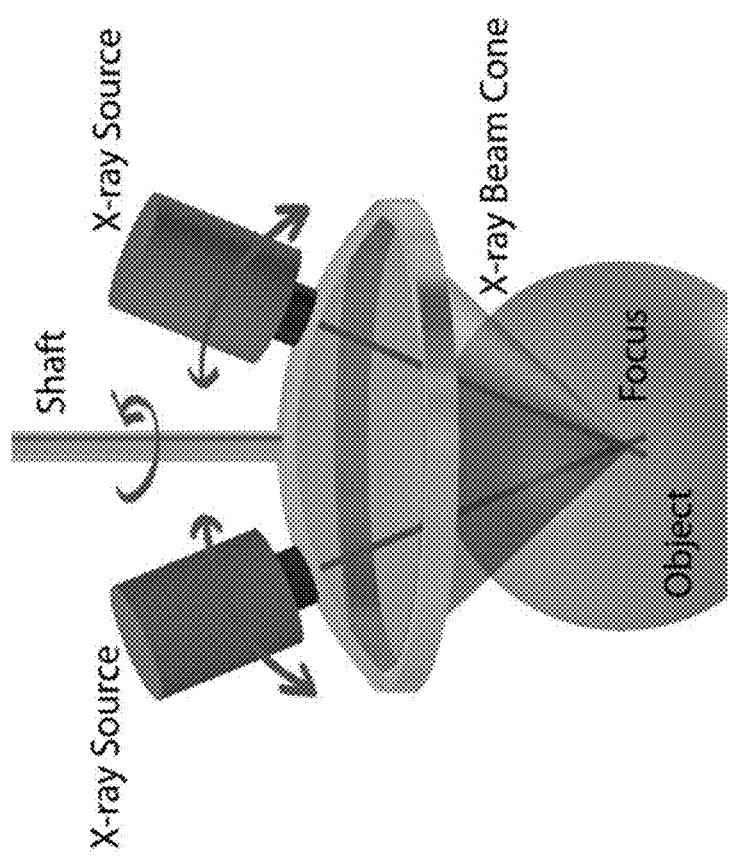
FIG. 10 illustrates an actual apparatus that can be used to create the focused X-rays inside an object or sample. The local dose at the focus can be a few hundred times greater than that at the entrance of the object.

Dose enhancement is the ratio of the local dose at a specific location to that at the skin, which should be uniform across the irradiated surface area by the scanning X-ray beam. The local dose is calculated as the ratio of the amount of energy deposited in the specified volume by the volume. The volume used here is as small as 0.5×0.5×0.5 mm$^3$. Dose enhancement can be achieved by rotating a beam of X-rays around the isocenter located in a treatment voxel (t-voxel). The rotation can happen in two- or three-dimensions (2D and 3D). As the beam of X-rays rotates around the isocenter, energy is constantly deposited in the t-voxel, whereas only a small and varying portion of the rest of the sample is irradiated. Therefore, the amount of dose in the t-voxel may significantly exceed the dose elsewhere, including that at the surface of the sample. Although a 2D rotation around the t-voxel was investigated extensively in the past, it is more advantageous to scan the X-ray beam in a 3D focusing configuration such as along the surface of a spherical cap to spread the X-rays into a much large volume to reduce the dose elsewhere. One example is shown in FIG. 10 in which two rotation motions, one around the shaft pointing at the isocenter and the other on a plane through the isocenter, are used to move two X-ray beams to form a truncated spherical cap to create a 3D focusing effect. Another way is to employ two rotary stages to control an X-ray beam to create a similar 3D focusing effect. It is also possible to accomplish this goal with multiple stationary X-ray beams aiming at the isocenter. In the simulation, both scanning and multiple beam modes are used, and the two can be readily converted into each other.

X-ray energy is selected by passing through filters to directly deposit energy in the sample or to excite nanoparticles in the sample. Here, X-ray sources with a tungsten target and various metal foil filters are used to tailor the emission spectrum into the one suitable for maximum excitation of Au or U nanoparticles in the sample.

The dose is calculated using a similar method previously described (Davidson, R. A. and T. Guo, *Nanoparticle Assisted Three Dimensional Point Scan X-ray Fluorescence Imaging*, 2013). Briefly, a group of photons emitted from an X-ray tube is simulated using the Monte Carlo method as the photons travel through water. Water is used here to represent the soft tissue; both have similar X-ray attenuation coefficients in this X-ray energy range. In water, energy deposition events are the product of either Compton scattering or photoelectric interactions; these events caused by the group of X-ray photons interacting with water within a defined volume (a bind) are used to determine the dose. Different bin dimensions are used to predict the dose profiles, either along the axial or Z axis or in the transverse directions perpendicular to Z direction.

Nanoparticle Assisted Dose Enhancement

Nanoparticles made of heavy elements can enhance X-ray absorption over water in the 50-120 keV energy region. If these nanoparticles are deposited in a t-voxel, then dose enhancement factor for the t-voxel can be greater. Normally up to 1 wt. % of Ag, Au or U in the form of nanoparticles can be loaded to a t-voxel, as higher concentrations of these nanoparticles in the t-voxel are more difficult to attain. One wt. % of Au and U nanoparticles were used to simulate the enhancement. When nanoparticles are present, the photon list is adjusted to account for photons being stopped within the target volume. X-ray spectra are filtered so that the highest X-ray energy is just under the K edge of the respective metal in the nanoparticles. It is assumed that all photons stopped within the nanoparticle-filled volume will lead to 100% local energy deposition because L shell fluorescence and any electron emission as a result of X-ray absorption will be fully attenuated within the target volume described here, which is not the case if X-ray energy is above the K edge of the metal in the target volume.

It is possible to use dosimetric reactions to probe the enhancement in a constructed phantom. Scavenging by nanoparticles must be considered and controlled to measure the true type 1 physical enhancement (T1PE) factor.

Results

Figure 11A:
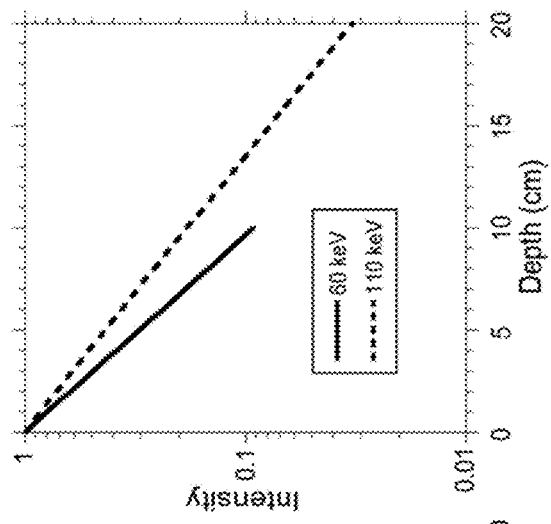
FIG. 11A illustrates spectra of X-rays from a 60 kVp X-ray source at different locations: from the source (dotted), after the filters (dotted-dashed), the actually spectrum used for the simulation (dashed) and at the target (solid) in the middle of the sample.
Figure 11B:
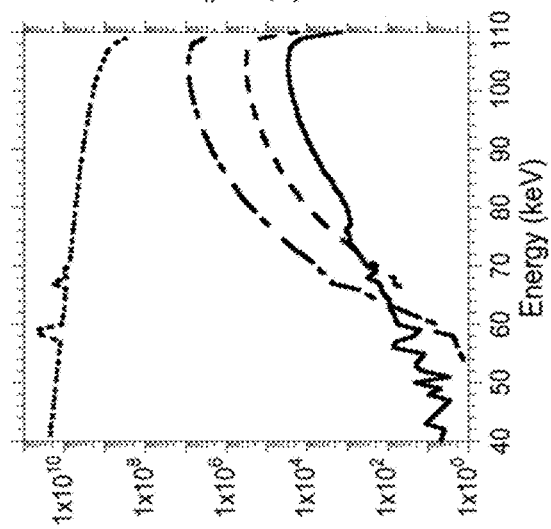
FIG. 11B illustrates similar energy spectra of the X-rays as shown in FIG. 10A from a 110 kVp tungsten X-ray source.
Figure 11C:
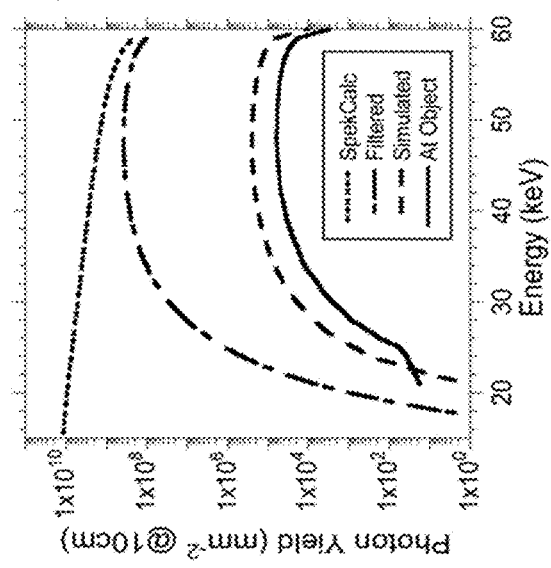
FIG. 11C illustrates X-ray intensity of a single X-ray beam as a function of penetration depth. 110 kVp X-rays penetrate 2 cm deeper than 60 kVp X-rays.

FIG. 11A shows the energy spectra (dashed line) calculated with SpekCalc from a tungsten X-ray source operated at 60 kVp (Poludniowski, G et al., Physics in Medicine and Biology, 2009, 54(19): p. N433-N438). Also shown in FIG. 11A are the filtered X-ray spectrum (dotted dashed line) and the X-ray photons that are used in the simulation (dashed line) as well as the X-ray spectrum at the target (solid line). FIG. 11B shows the four corresponding spectra for the source operated at 110 kVp. FIG. 11C shows X-ray intensity along the X-ray path as a function of distance from the surface. The decay of X-ray intensity into the sample depends on the energy of X-rays. For 60 kVp X-rays, the attenuation allows X-rays to penetrate to 4 cm of water (intensity decreased to 1/e). The depth increases to 6 cm for 110 kVp. FIG. 11C shows why these X-rays are generally not used for treatment due to the high attenuation by water, which has a similar attenuation to soft tissues for these X-rays.

The energy deposition events are binned into 0.05 cm radius×0.05 cm thick discs in the axial (Z) direction and the dose in these bins is calculated to give the axial dose profile shown in FIG. 12. For clarity purpose, the dose is normalized to that at the skin. For calculating transverse dose profiles, energy deposition events are binned to 0.05×0.05 cm squares on XZ plane sandwiched by two XZ planes 0.2 cm apart. The two planes are symmetrically positioned with respect to the isocenter. FIG. 12A shows the results of dose enhancement in the axial direction for the 60 kVp X-rays shown in FIG. 11A for three scanning focusing configurations to increase the local dose at the target located at the center of a 10-cm water cube. FIG. 12A shows the enhancement along the axial direction for 9 beams on a plane (dotted-dashed), 65 beams in a three-dimensional configuration (dashed), and continued scanning of one beam in 3D (solid). The full width at half maximum (FWHM) for continuous scanning is 5.8 mm, which is greater than that of 9-beam (2.8 mm) and 65 beam (2.8 mm) focusing configurations for a 2-mm diameter X-ray beam. This is mainly attributed to the overlap of the beams in the axial direction, especially in the continuous scanning focusing case which generates an almost flat top intensity or dose enhancement profile. FIG. 12B shows the dose enhancement in the transverse direction. It is worth noting that although the transverse enhancement is also normalized against the dose at the skin, the absolute dose is different due to the use of a slightly different bin size as mentioned above. The FWHM is about 2 mm, approximately the same as the X-ray beam diameter of 2 mm. The focusing employed here therefore creates an oblate spheroid. For the continuous scan case, the dose is actually the lowest at the skin due to the overlap of the scanning X-ray beam at different angles.

The enhancement for 9 beams on a plane (a 2D focusing) is only 2-3 fold, as shown in FIG. 12A and FIG. 12B. For 65 beams arranged in a 3D spherical cap configuration, the enhancement increases to about 25 fold. On the other hand, the enhancement for the same beam used in the continuous scanning mode is 185 fold. Such an enhancement can reduce the surface dose to below acute level of 0.1 Gy while the dose at the target exceeds 18 Gy. 0.1 Gy is below the acute dose allowed for human whereas 18 Gy is close to the dose needed to kill a solid tumor (Sachs, R. K. and D. J. Brenner, Proceedings of the National Academy of Sciences of the United States of America, 2005, 102(37): p. 13040-13045).

FIG. 12C and FIG. 12D show the corresponding enhancement profiles for the 110 kVp X-rays. The enhancement factors are higher, reaching 358 folds at the focus. Similarly, the enhanced region is an oblate spheroid, with the longer axis in the axial direction.

FIG. 13 shows the enhancement with the assistance of nanoparticles. In this case only the region near the focus is shown. When the gold (1 wt. %) is uniformly distributed in a 2-mm thick transverse layer centered at the isocenter, the enhancement is 405 folds, which is greater than that for the same weight percentage of gold distributed in a 5-mm thick layer. This is caused by the higher intensity of exciting X-rays near the focal point for the thinner Au layer, which attenuate X-rays less and allow more X-rays to reach the gold layer before X-rays reach highest intensity at the focus. The result of continuous scan for Au is shown in FIG. 13A. The enhancement is 319 folds when more gold is used in a larger volume (5 mm thick). FIG. 13B shows that for U excited with 110 kVp X-rays, which only shows that with a 5-mm layer of 1 wt. % U. The enhancement increases from 358 folds to 511 folds with the addition of U.

A clear advantage of using the nanoparticles is the well-defined enhancement region with the introduction of nanoparticles. The FWHM improves significantly, down to a fraction of mm from a few mm. The shape of the enhancement region essentially adopts that of the loaded nanoparticles.

FIG. 14 shows a 2D X-ray intensity plot on a plane parallel to the axial axis and through the focus near the treatment region. The 3D shape of the t-voxel shown here is oblate spheroidal with the longer axis along the axial direction for the scanning 2-mm diameter X-ray beam. This shape determines the resolution of the energy deposition profile, which has a higher resolution in the transverse directions than axial due to the fact that X-ray beams are dominant in the axial direction. The solid angle of X-rays hitting the t-voxel is clear visible in FIG. 14, going from −22.5° to +22.5° with respect to the axial direction on any transverse plane, corresponding to 0.48 sr. The enhancement in the t-voxel compared with that at the skin is dependent of the solid angle; the greater the solid angle, the greater the enhancement, representing a stronger focusing effect. In cancer therapy, larger solid angles may be used, which means even greater enhancement than presented here may be obtained.

After the addition of nanoparticles, which occupy a cylindrical volume, the shape of t-voxel adopts that of the nanoparticles, as shown in FIG. 14B. This higher spatial resolution of enhanced regions may facilitate precision treatment of cancer.

Discussion

The use of 50-120 keV X-ray sources allows easy movement of these sources, making it easier to create complex motions of the X-ray beam(s) and therefore 3D scanning focusing using these beams and sources.

It is important to point out that the high enhancement of over 511 times at the target over the dose at the skin only occurs for small targets deep in the sample or body. For larger targets such as those in 3D conformal cancer therapy, the X-ray beam size may need to increase, which will reduce the magnitude of enhancement. It is also possible to move the t-voxel formed by the scanning of a thin X-ray beam to cover the larger target. However, this will also reduce the enhancement because although the t-voxel moves from one to another completely different spot, the two X-ray cones occupy approximately the same space. It is still beneficial to use the scanning focusing mode so that lower dose is at the surface or entrance by spreading the dose to a much larger volume away from the t-voxel or isocenter, which is essentially what is used in 3D conformal radiation therapy. One way to maintain high enhancement in cancer therapy is to deliver dose to only one small spot at a time to kill tumor within the t-voxel. Subsequent deliveries to an adjacent spot can be made at delayed times to allow the healthy tissues in the beam path to completely recover. Large solid tumors may be killed in this way.

It is also worth pointing out that the 3D scanning focusing approach described here, if combined with other methods such as X-ray triggered release of chemotherapeutic drugs (Starkewolf, Z. B et al., Chemical Communications, 2013, 49(25): p. 2545-2547), can further reduce the dose to below acute level (0.1 Gy) in the healthy tissues while completely eradicating a tumor within the targeted volume via the activation of chemotherapeutic drugs.

It seems the enhancement due to the introduction of nanoparticles is small compared with that of scanning beam(s). Although this is true, there are several important improvements with the use of nanoparticles. For example, it is important to realize that these nanoparticles may help diagnose cancer through nanoparticle assisted imaging if these nanoparticles can target tumors (Dreaden, E. C et al., Small, 2012, 8(18): p. 2819-2822). The net benefits of being able to reveal cancer locations and creating higher local dose at these locations seem to compensate the added complexity of using nanoparticles. Further, nanoparticles can improve the spatial resolution of dose enhancement, as shown above, from a few mm to less than a mm. Additionally, it is possible to use these nanoparticles to generate other types of enhancement such as type 2 physical enhancement (T2PE), which can reach over 240 fold enhancement using specially arranged nanostructures (Lee, C et al., J. Phys. Chem. C, 2012, 116(20): p. 11292-11297).

The scattered X-rays create a weak background around the X-ray beam. This background contains a small amount of energy. This is because X-ray attenuation is largely through Compton scattering of X-rays by water molecules, and the Compton electrons deposit all their energy in the immediate space (within microns) of the scattering events. In the presence of nanoparticles made of heavy elements, the situation is slightly different. Fluorescent X-rays may have enough energy to redeposit energy in the whole sample, so this part of the secondary energy deposition reduces the enhancement by a small margin. The enhancement caused by X-ray fluorescence from the nanoparticles is hence insignificant compared with the enhanced absorption and amount of energy retained by the electrons within the t-voxel. Because of this secondary redistribution of absorbed X-ray energy, X-ray photons with energy above K edges are less useful in giving rise to enhanced energy deposition in the t-voxel.

The new method discussed here resembles the popular intensity-modulated radiation therapy (IMRT) in which linear accelerators are used to point MeV photon beams at the target from different angles to deliver more dose to the target while minimizing the dose in the surrounding healthy tissues. The scans are generally made on the same plane while the shape and the intensity of the photon beam are varied to deliver the maximum dose to the tumor target. Due to the relatively large beam size and confined scan space, the dose enhancement is limited. The new method investigated here takes advantage of the much more mobile X-ray sources to perform 3D focusing using a sharp pencil X-ray beam(s) to significantly reduce the dose elsewhere than that at target.

The scanning focusing method can also be used to excite X-ray fluorescence for imaging, which is described in a recent report (Davidson, R. A. and T. Guo, *Nanoparticle Assisted Three Dimensional Point Scan X-ray Fluorescence Imaging*. To be submitted, 2013). However, the speed of movement of the X-ray source(s) needs to be fast because only a small fraction of the total dose at the target is required for imaging. In addition, it is important to realize that even if a large volume of target needs to be imaged, it is still beneficial to employ scanning focusing imaging to lower the dose in tissues at shallow depths including surface.

Conclusions

A three-dimensional scanning of an X-ray beam(s) aimed at an isocenter can increase the dose at the center over that at the skin by many hundred fold. The magnitude of enhancement depends on the X-ray energy, the range of movement, the composition and size of the sample, and the depth of the t-voxel. A 185-fold dose increases over that the skin dose can be achieved at 5 cm deep in the water. Upon adding X-ray absorbing nanoparticles into the t-voxel, the enhancement can increase by many folds in addition to the scanning caused enhancement. For 1 wt % Au nanoparticles that do not interfere with energy release and scavenging, the enhancement is another 2-fold increase over the scanning enhancement, resulting in an overall enhancement of 404 times. Other elements and X-ray energies can be used and similarly high enhancement factors are predicted. Up to 511 fold increase is predicted with using uranium and a 110-kVp X-ray tungsten source. The shape of enhancement is oblate spheroidal for focusing without nanoparticles and adopts that of the loaded nanoparticles with 1 wt. % Au or U nanoparticles.

Example 3

Additional Information on Nanoparticle Assisted Three Dimensional Point Scan X-Ray Fluorescence Imaging This Example elaborates on the information presented in Example 1. Applicants explored an imaging method that can detect individual small tumors deep in the body; a difficult task for existing methods because regular CT generates too high a background noise to detect these tumors and conventional PET or SPECT lacks the spatial resolution to pinpoint the locations of these tumors. Applicant's method accomplishes this goal by employing one or more needle beams of X-rays and apertured detectors to minimize unwanted scattered X-rays, thereby reducing background noise.

Applicants developed a Monte-Carlo simulation method to evaluate the potential of the simultaneous use of three components: (1) a needle beam or beams of X-rays to irradiate (2) tumor-targeting X-ray fluorescent nanoparticles so that (3) X-ray detectors equipped with small solid angle apertures can detect preferentially only X-ray fluorescence emitted from these nanoparticles. Applicants found that the combination of a needle beam of X-rays and the apertured detectors enables sensitive detection of individual or isolated small tumors deep in the body. X-ray fluorescence emitted from Ag and Au nanoparticles irradiated with a needle beam of X-rays emitted from a microfocus X-ray source operated at 40 or 100 keV is detected by X-ray detectors equipped with small solid angle apertures. Such a combination of excitation and detection defines one or many small imaging voxels (i-voxel) from which X-ray fluorescence is detected. The energy dispersive detectors can further select only those X-ray fluorescent photons emitted from the nanoparticles as signal, rejecting the majority of scattered X-rays coming from background materials such as tissues within the i-voxel. Three-dimensional images or profiles of the nanoparticles in the sample can be formed by scanning the i-voxel through large-volume samples, such as the human body. As few as tens of micrograms of nanoparticles embedded in mm dimension volumes can be detected in up to 10 cm cube of water, suggesting that it is possible to detect a single millimeter-sized tumor loaded with approximately 1 wt. % of these nanoparticles buried deeply in the body. Applicant's method is more sensitive than the existing CT methods, and possesses higher spatial resolution than conventional PET and SPECT and may be used as an imaging tool for detecting small tumors and early stage cancers.

Introduction

X-ray imaging has played an important role in revealing the interiors of dense, opaque objects and anatomy. The imaging principle previously relied on different parts of the object or body having different attenuation coefficients of X-rays, also known as radiodensities. Computed tomography (CT) takes advantage of various reconstruction techniques to efficiently map out internal structures of the body or other three-dimensional (3D) objects. Similar to conventional 2D X-ray direct imaging, CT depends on attenuation of X-rays by different body parts, constructing 3D images from multiple high spatial resolution 2D projections that bear the information of the targets with detectable radiodensity differences.

The size of the tumor and its radiodensity together determine whether it is possible to detect the tumor in the body by CT. The 2D projections have to show the tumor so that the 3D images can reveal its size and location. This means that the size of tumor and its difference in radiodensity from the surrounding healthy tissues have to be great enough for the tumor to show up on the 2D projections. As a result, it is difficult for CT to detect individual small tumors due to the low contrast resulting from small changes (e.g., less than 10%) in radiodensity between tumor and normal tissues within a small volume (mm in dimension) in the whole cross-section of the body (usually >10 cm) in the X-ray path. In order to detect such small radiodensity changes with CT, impractically large doses of X-rays are needed. Hence, more sensitive (detection of small tumors less than 1 mm in size), deeper penetrating (>10 cm), higher spatial resolution (mm or less) and low dose (sub-acute or <1 rem or 10 mSv) methods of 3D imaging are needed.

Attempts to improve the sensitivity of CT have been made. One of the recent progresses made in this area is the use of nanomaterials. If there are enough nanomaterials taken up in the tumor region, then regular CT in the absorption mode may be able to detect the tumor, as demonstrated previously with gold nanoparticles ((Luo, T et al., Optics Express, 2011, 19(18): p. 17030-17039; Hainfeld et al., British Journal of Radiology, 2011. 84(1002): p. 526-533). In these cases the tumor sizes are large enough so that even regular CT could detect tumors without gold nanoparticles. For smaller tumors at early stages that take up less gold or silver nanoparticles, the detection with conventional CT has not been attempted. X-ray fluorescence CT (XFCT) has been developed recently, which is supposed to be more sensitive because of decreased background noise. There are several variations of this method reported in the literature. Meng et al. used synchrotron X-ray beams and multiple micro apertures to demonstrate a unique way of imaging small samples (Meng et al., Proc. of SPIE, 2010, 7804: p. B1-B9). However, the X-ray energies were below 10 keV, which could not be used for tumor detection in humans. Jones et al. developed a technique where a combination of a wide X-ray beam and multiple detectors with apertures was used to shorten the imaging times of detecting large targets loaded with 0.5 wt. % or more gold in small-sized phantoms (Jones et al., Physics in Medicine and Biology, 2012. 57(23): p. N457-N467). More recently, Manohar et al. demonstrated a method with which they used to probe low energy (~13 keV) X-ray fluorescence from Au embedded in centimeter-sized water phantoms (Manohar et al., Medical Physics, 2013, 40(8)). Bazalova et al. showed that it is possible to use more collimated X-ray beams and X-ray fluorescence detectors to image nanoparticle-loaded targets in small phantoms (Bazalova, M et al., Ieee Transactions on Medical Imaging, 2012. 31(8): p. 1620-1627; Bazalova, M et al., International Journal of Radiation Oncology Biology Physics, 2012, 84(3): p. S689-S689; Bazalova, M et al., Physics in Medicine and Biology, 2012, 57(22): p. 7381-7394). In all these endeavors, the phantoms were relatively small (a few centimeters in diameter) and the sizes of the targets loaded with 0.1 to 1.0 wt % gold were relatively large (millimeters in diameter).

The experiments described above have demonstrated that it is still difficult to detect standalone, millimeter-size 3D targets in large 3D samples, even with the assistance of nanomaterials and fluorescence-based CT. Nonetheless, employing nanoparticles can help increase the sensitivity of tumor diagnosis for the purpose of detecting small, millimeter sized tumors in the body. Generally speaking, 1 wt. % AuNPs or AgNPs can be delivered to or taken up by the tumor. Thus, it is expected that to find 1-mm cubic sized tumors, approximately 10 μg of nanomaterials within this volume buried in the body would need to be detected. This is almost an order of magnitude less than the minimum total amounts of what have been tested in the XFCT experiments using small phantoms mentioned above.

Meeting the above-mentioned imaging and detection requirements may not only satisfy the need to detect small changes in the body, but also help track the fate and transport of nanomaterials entering the ecosystem. Because mice or rats are often used as animal models in studying the health impact of nanomaterials, it is important to know the amount and distribution of nanomaterials in the lungs of mice or rats. This requires being able to image approximately 1 μg nanomaterials in the lung with a spatial resolution on the order of sub-millimeters (Anderson et al., in preparation). These requirements are equally stringent as those needed for imaging nanomaterials in human.

To meet the imaging needs described herein, Applicants explored methods to detect the aforementioned minimal amounts of nanomaterials in small, individual targets embedded within a large sample or body of water, which is close to the density of human tissues. Applicant's approach described herein is based on detecting X-ray fluorescence emitted from nanomaterials excited with a needle beam of X-rays with X-ray detectors equipped with small solid angle apertures. The improved resolution and sensitivity derives from the limited excitation of the samples with the incident X-ray needle beam and the guided detection by the apertures placed in front of the X-ray detectors. The use of gold and silver nanoparticles in water phantoms was also explored, as gold (Au) is biologically benign and silver (Ag) offers high sensitivity when studying small samples.

Applicant's method of using nanomaterials to assist the imaging of small tumors in the body with a X-ray needle beam is called nanoparticle assisted X-ray fluorescence imaging, or NAXFI. In the following, Applicants describe how to detect small targets (1-2 millimeters in dimension) of small amounts of nanoparticles (10-30 μg) in large (5-10 cm cubes) water phantoms.

Materials and Methods

The principle of the new imaging tool, as well as the instrumentation and simulation process, are described herein.

NAXFI Principle

The working principle of the instrument is shown in FIG. 15. The instrument contains 5 major components, as shown in FIG. 15A: 1) A X-ray source; 2) Filters and an aperture for the source(s); 3) Sample stages; 4) Detector(s); and 5) Aperture(s) for the detector(s). X-rays emitted from the X-ray source pass through a set of filters and an aperture before reaching the sample, which is mounted on the XYZ motion stage. One or more detectors equipped with the apertures detect X-ray fluorescence emitted from the nanomaterials and scattered X-rays emitted from the sample irradiated by the X-ray needle beam. The scattered X-rays constitute the background or noise whereas the fluorescent X-rays are the signal. The detector aperture limits the solid angle through which X-rays can be detected (denoted by detector cone as shown in FIG. 15B). This solid angle intercepts the X-ray needle beam in space to form an imaging voxel (i-voxel). When the dimensions of an i-voxel are small, this voxel can be viewed as the point of interest (POI). 3D images can be formed by scanning the i-voxel throughout the sample while detecting the fluorescence. As a result, this approach is a 3D point scan, not a tomographic (sectioning imaging) method. Such a detection method enables high sensitivity probing of the target in the sample, which can be much higher than CT based methods due to significant reduction of the scattered X-ray photons entering the detector(s).

In this method, the transverse resolution (X or Y direction perpendicular to the X-ray needle beam, which is along the Z axis) is defined by the convolution of the dimension of the X-ray needle beam and the detector aperture cone in the X or Y direction. Because the diameter of the X-ray needle beam is generally smaller than the dimensions allowed by the acceptance solid angle of the detector aperture, the overall transverse resolution is determined by the X-ray needle beam diameter. There is negligible X-ray scattering from samples beyond the region excited by the X-ray needle beam. The axial resolution (Z direction) is defined by the opening of the detector aperture (detector cone), as shown in FIG. 15B. The vertical (Z direction) opening of the apertures in front of the detectors is set so that the detectors achieve the highest signal to noise ratio (S/N). The apertures define the height of the i-voxel, which should be comparable to the diameter of the X-ray needle beam at the target. This configuration makes the i-voxel nearly cubic.

An exemplary target is a 3D region loaded with X-ray fluorescent nanoparticles. From FIG. 15B, the target is a 1 mm thick, 1 mm radius cylindrical disc. The nanoparticles of various concentrations are uniformly distributed in this disc, which resides in the sample as shown as points A, B, or C in FIG. 15A. Both Ag or Au atoms of a chosen percentage weight in water, as well as no actual nanoparticles, were assayed.

3D imaging of the target in the sample can be obtained by scanning the i-voxel throughout the sample. In practice, the i-voxel can be scanned through only some parts of the sample. In a typical imaging scenario, regular CT may be used to examine the entire sample, followed by NAXFI of the suspicious regions. No reconstruction is needed for NAXFI because signals from the detectors coded with coordinates of the i-voxel can be directly used to form images.

If multiple detectors are used, the apertures for these detectors can aim at the same i-voxel, which is the focus of these detectors. In addition to one X-ray needle beam and one focus configuration (1NB/1F, FIG. 16A), other configurations of multiple sets of detectors to simultaneously probe different spots or foci along the path of one or more X-ray needle beams are possible. For instance, it is possible to use 1 needle beam (1NB) with detector apertures aiming at three foci (3F). This is the 1NB/3F configuration, as shown in FIG. 16B. It is also possible to use 3 sets of detector apertures, each focusing at a different i-voxel, therefore creating 3 foci (3F) to simultaneously detect 3 i-voxels along three X-ray needle beams (3NB), as shown in FIG. 16C (3NB/3F). Other configurations of simultaneously detecting X-ray fluorescence from many spots excited with many X-ray needle beams are possible. This will be controlled by algorithms and similar to computed tomography. A generic configuration using a matrix of a number of X-ray needle beams and a number of foci of the detector apertures can be employed to significantly shorten the imaging time.

Simulation

The configuration shown in FIG. 15 and FIG. 16A (1NB/1F) were simulated and the other configurations can be extrapolated from the results of 1NB/1F. In the simulation, a needle beam of X-rays is sent into the sample. The X-ray photons are either scattered or absorbed by the sample or the nanoparticle-loaded target. A chart illustrating exemplary simulation steps is provided in FIG. 9. Briefly, the simulation contains four parts, as described below. The first part tracks the X-ray photons traveling in the sample and determines the end points, which can be the absorption of the photon, scattering of the photon, or exit of the photon from the sample. The second part deals with how X-rays interact with nanomaterials. In the third part, the scattered and fluorescent photons are tracked to determine if they enter the detector. Finally, targets in the sample are mapped to form 3D images by scanning the i-voxel around a target.

Each photon entering the sample is simulated by tracking it in the sample. FIG. 9A shows the simulation of photons interacting with water alone and FIG. 9B shows that with the nanoparticles alone. In each of the two simulations, the program tracks the X-rays photons in the sample, determining the end point, whether it is absorption of the photon, scattering of the photon, or exit of the photon from the sample. If the photons enter the target region, then the program makes similar differentiations, except that X-ray fluorescent photons from nanoparticles are obtained and their trajectories are used to calculate the detection of nanoparticles. Targets in the sample can be mapped by scanning the beam of incoming photons while detecting the X-ray fluorescence.

Interaction of X-Rays with the Sample

As shown in FIG. 16, the X-ray beam irradiates the sample with one or more targets inside. In the simulation, each X-ray photon starts at the center of bottom face of the sample cube, aiming inside. The starting position of each X-ray photon, of energy E, is a random point within the X-ray beam diameter traveling in the +Z direction (x, y, z=0, $\theta$=0, $\varphi$=0, E). The value E is sampled from an X-ray energy spectrum. $10^6$ or $2 \times 10^6$ photons are used for the cases of Ag and Au, respectively. X-rays can either be absorbed or scattered by atoms in the sample or target. Once a photon starts the simulation journey, it is tracked through the whole sample (e.g., a 10×10×10 cm cube of water). To track a photon, the sample medium (water) is specified and a random free path is calculated from the photon's current energy (Chan et al., Physics in Medicine and Biology, 1983, 28(2): p. 109-129). The next location is determined by the calculated free path and the new location (x, y, z) and direction ($\theta$ and $\varphi$) is given (x, y, z, $\theta$, $\varphi$, E') with a new energy E'. At this new location, the type of interaction (photoelectric, Compton, or coherent) is determined according to their relative probabilities (National Institute of Standards and Technology). If the interaction is photoelectric, the energy of the photon is deposited and the photon tracking is terminated. If the interaction results in Compton scattering, the scattering angle $\theta$ is calculated using the Klein-Nishina formula modified by the incoherent scattering function (Chan et al., Physics in Medicine and Biology, 1983, 28(2): p. 109-129; Hubbell et al., J. Phys. Chem. Ref. Data, 1975, 4(3): p. 471-493). The scattering angle then determines the energy loss of the scattering event using the Compton formula (Compton, Physical Review, 1923, 22(5): p. 0409-0413). If the interaction is coherent, the photon retains the energy and the new scattering angle $\theta$ is predicted using the Thompson equation. In both Compton and coherent scattering events, the angle $\varphi$ is selected randomly. Photons are tracked in this fashion until (1) a photoelectric event occurs, or (2) the photon's energy is less than 10 keV, or (3) the photon exits the water cube sample. Because 10 keV X-rays are significantly attenuated in water, it is assumed that these photons will deposit 100% of their energy within 2 mm of water. The simulation creates a list of photons and there trajectory events.

Interaction of X-Rays with the Target

Figures 17A, 17B:
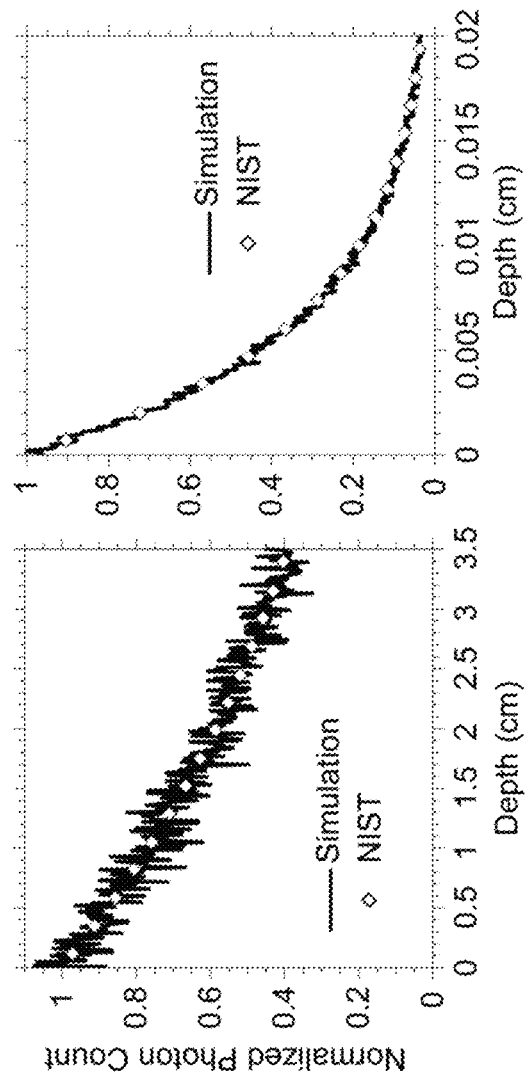
FIGS. 17A-FIG. 17B illustrate photon free-path benchmarking.

The target is considered as a uniform mixture of the elements of interest and water. Once a photon enters the volume of the target, it is evaluated for causing a photoelectric event by the elements. A mean free path is determined based on the density and type of the elements in the target volume. If the free path is less than the thickness of the target, the interaction type is determined at that interaction location. If the interaction within the object is photoelectric, the emission probability determines whether a fluorescent photon is created with the characteristic K line energies of the target element, which is then tracked through the water medium until a photoelectric occurs or the photon exits the boundaries. The fluorescence simulation compiles a list of trajectories of all the individual fluorescent photons. Benchmark results are shown in FIG. 17A-FIG. 17B, which shows a good agreement between results obtained using the free path randomization method and NIST attenuation data.

Photon Detection by the Detector

The excitation and fluorescence photon lists created from the abovementioned interactions are searched to determine if any trajectory of a scattered or fluorescent photon passes through both the front and back planes of the detector aperture. The search result returns the intersection points and energies of the photons on both the front and back plane of the aperture. The detector is positioned behind the back aperture plane, so any photon passing through the aperture is considered detected. A histogram of the photons binned to 150 eV (E-bin) produces the simulated signal.

Image Formation

The sample, together with the target inside, is rastered by the XYZ motion stages while the detectors collect the X-ray photons. Each detector is equipped with a multichannel analyzer and the processed signals are sent to a computer. The energy resolution of the detector is 150 eV. The fluorescent X-ray photons at a specific energy (characteristic K lines) are recognized against the background scattered X-ray photons. The average background signal along with its standard deviation of ±2 E-bins around the desired E-bin of the K lines are used to randomly generate the total background count. This random background is generated at each individual i-voxel and added to the fluorescence image data to account for noise. Because the background is the same each time the i-voxel is moved to a new location, only the fluorescence is simulated at each new i-voxel. The fluorescent signal from E-bins containing $K_\alpha$ and $K_\beta$ characteristic lines is summed and the detected signal has the combined S/N.

Results

As X-rays travel from the source to the sample and through it, the energy spectrum changes as low energy X-rays get absorbed or scattered more than the higher energy or hard X-rays. In order to maximize the fluorescence yield, different initial X-ray spectra are created by letting X-rays from the source go through different X-ray filters. These filtered X-ray spectra can more efficiently excite the elements in the target above their absorption K edges. FIG. 18 shows the spectral evolution of the two X-ray spectra for investigating two target elements: Ag (K edge at 25.51 keV) and Au (K edge at 80.72 keV). FIG. 18A shows the spectra for detecting Ag in water from (i) the source (short dashed) to (ii) after the filters (dot-dashed) and (iv) at the target (solid) in the middle of a 5 cm cube of water. The dashed lines (iii) represent the spectrum used in the program. The voltage of the X-ray tube is set to 40 kVp. FIG. 18B shows those for Au from a source operated at 100 kVp. The X-ray filters are different in these two cases (see caption).

The X-rays scattered by background water within an i-voxel or absorbed by the atoms in the target (Ag and Au) and reemitted as fluorescent X-rays may be detected by the detector(s). The simplest configuration is a single X-ray needle beam irradiating a sample with a single target detected by an array of detectors with their apertures aiming at the target (one focus), as shown in FIG. 16A. The diameter of the X-ray beam is 2 mm. 1 wt. % of Ag in a 1-mm tall and 1-mm radius disc target is centered in a 5 cm water cube. To detect Ag, a detection ring was employed with 163 detectors (each with a 5×5 mm² detection area) arranged at a 13 cm radius circle whose plane is perpendicular to and centered on the X-ray beam. For detecting fluorescence from 1 wt. % Au in the same dimensioned target centered in a 10 cm water cube, the detection ring is 15.5 cm and consist of 195 detectors. Each detector is equipped with an aperture aiming at the target. In both cases, the front opening of the aperture has a 1.75 mm height and the back 5 mm. The length of the aperture is 10 cm. The dimension of the aperture controls the axial (Z direction) spatial resolution while the X-ray beam diameter controls the transverse resolution (XY direction). FIG. 19 shows the energy spectra of the photons detected by the detectors using the two spectra described in FIG. 18. In FIG. 19A and FIG. 19B, fluorescent $K_\alpha$ and $K_\beta$ peak locations from Ag and Au are the sharp, intense peaks (labeled with *) and the broader, weak peaks represent scattered photons. The amount of nanoparticles is 31.4 µg (1 wt. % of the water displaced by the Au or Ag atoms in the target) in both cases. For Ag, the detected X-ray fluorescence is 21% of the total photons hitting the detector; and for Au, the percentage of X-ray fluorescence from the target drops down to 8% of the total photons detected. These numbers are listed in Table 2 (see below). FIG. 19C and FIG. 19D are without the detector apertures, showing more fluorescence and much more background, demonstrating the effect of the detector aperture.

Figures 20A, 20B, 20C, 20D, 20E, 20F:
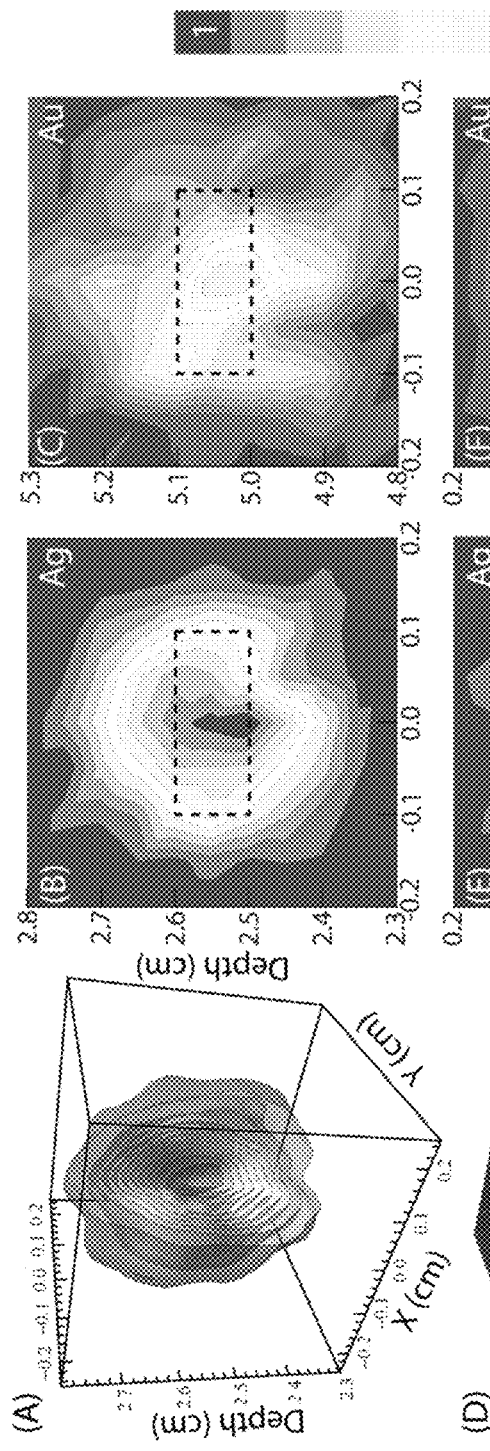
FIGS. 20A-FIG. 20F illustrate simulated 3D imaging of the targets in the sample.

Target imaging can be achieved by moving the sample in a point by point fashion with respect to the X-ray beam and detectors, or vice versa. FIG. 20 shows the simulated results for imaging the Ag and Au targets in the cubic samples. In FIG. 20D, the whole sample and X-rays are shown. Gray trajectories represent the exciting X-rays and X-rays scattered by water. Red trajectories show the fluorescent X-rays from the nanomaterials in the target. FIG. 20A shows a 3D contour plot of the image of the target in the scanned sample volume. 2D contour profiles are shown in FIG. 20B and FIG. 20C (axial cross section) and FIG. 20E and FIG. 20F (transverse cross section). The signals in these four panels show the results of imaging Ag or Au targets and are normalized to that of FIG. 20B and FIG. 20E, which show the 1 wt. % Ag disc target in a 5 cm cube. FIG. 20C and FIG. 20F show the images of the 1 wt. % Au disc target in a 10 cm cube. Black dashed lines show the profile of the targets used in the simulation.

As explained in the Methods section, the transverse resolution (X and Y directions) is determined by the X-ray beam and the axial resolution is defined by the vertical opening of the aperture. In the case using Ag nanoparticles, the axial resolution of the aperture is better than 1.5 mm in the axial or Z direction. The transverse resolution is better than 2 mm. FIG. 21A-FIG. 21B show two targets separated by 3 and 1.5 mm vertical gaps. The targets separated by 1.5 mm remain discernible. The signal outside the nanoparticle target regions is caused by the fact that the i-voxel partially overlaps with the target because the vertical (axial) resolution is 1.5 mm.

The results shown here support that it is possible to image small amounts of nanomaterials distributed in a single small volume in a large sample. The potential of Applicant's imaging tool can be further estimated as follows. Several parameters directly influencing the noise levels are shown in FIG. 22. FIG. 22A shows the signal to noise ratio (S/N) for detecting 1 wt. % Ag and Au in the target located in a 5 or 10 cm water cube as a function of the height of the front opening of the aperture, which in turns determines the solid angle through which the detector can detect X-ray photons. Smaller openings reduce the noise, but can also limit the signal if they are too small. Large openings will allow more scattered photons to be detected and hence reduce the S/N. FIG. 22B shows the dependence of the S/N as a function of the target size for a fixed X-ray beam size of 2 mm. It shows that S/N decreases as the target size decreases, due to the reduced signal while the noise is kept approximately constant. This means it is important to keep the X-ray beam size comparable to the smallest target size so to keep the noise low and spatial resolution high. FIG. 22C shows the dependence of the S/N as a function of the weight percentage of the target in a fixed volume. A linear relationship is shown. In all cases, Ag in the 5 cm phantom produces a higher S/N than Au of the same weight percentage in a 10 cm phantom.

Table 2 summarizes the parameters used and results generated in the simulation. It shows the flux of the X-ray beams at the entrance of the samples from a 1 kW tungsten microfocus X-ray source through an aperture that gives rise to a 2 mm needle X-ray beam at the target. $10^6$ or $2\times10^6$ photons are used in the cases of Ag and Au respectively and the numbers of photons at the target locations (after attenuation in the sample) are given. It also shows the total numbers of scattered and fluorescent X-rays as well as the detected fluorescence and scattered X-ray photons. The number of detectors and time taken to detect the nanoparticles in the targets are shown. The detection times are calculated based on the given incoming X-ray flux. Peak X-ray doses at the skin of the sample for each data acquisition and 2D and 3D imaging are also given. The skin dose is calculated based on the energy absorbed per mass of water in the first 1 mm of the sample. Because the scan is done with overlapping X-ray beam positions, the average dose of a scan is greater than the single exposure. A 2D sectioning scan of a whole cross section of the imaging volume using a 1 kW X-ray source takes approximately 57 milliseconds and 189.9 seconds for Ag in 5 cm and Au in 10 cm samples respectively. The respective doses are 0.32 mGy and 0.3 mGy. It is possible to quickly rotate the X-ray beam pivoted at the i-voxel as if the X-rays focus at the i-voxel. This can reduce the dose at the entrance by several times. Such focusing may be useful in using these X-rays to treat diseases in the body or causing responses in large opaque samples.

TABLE 2

Summary of the Calculations Using a 1 kW Microfocus X-ray Source

| Parameter for each Element of Metal in Nanoparticles | Ag | Au |
|---|---|---|
| Sample Size | 5 cm Cube | 10 cm Cube |
| Target Size (depth, diameter) | 1 mm, 2 mm | 1 mm, 2 mm |
| Target Location in Sample (X, Y, Z (cm)) | (0, 0, 2.5) | (0, 0, 5) |
| X-ray Source Flux (#/mm²s @ 5 cm) | $2.96 \times 10^{10}$ | $1.786 \times 10^{10}$ |
| X-ray Flux After Filters (#/mm²s @ 5 cm) | $4.56 \times 10^8$ | $2.716 \times 10^5$ |
| 2 mm Diameter Needle Beam (#/s⁻¹) | $1.43 \times 10^9$ | $8.532 \times 10^5$ |
| Photons Simulated at Entrance (#) | $1.00 \times 10^6$ | $2.00 \times 10^6$ |
| Photons at Target Depth (#) | $3.45 \times 10^5$ | $8.28 \times 10^5$ |
| Fluorescence Total from Target (#) | 9666 | 4779 |
| Detected Fluorescence (#) | 22.3 | 16.43 |
| Total Detected Background (#) | 82 | 184 |
| Background Noise Average (±2 bins) | 1.80 | 2.20 |
| Ring Detector Equivalent (#) | 163.4 | 194.8 |
| Time to Detect (s) | $6.99 \times 10^{-4}$ | 2.3 |
| 2D Image Time (s) [9 × 9 Array] | 0.057 | 189.88 |
| 3D Image Time (s) [9 × 9 × 11 Array] | 0.62 | $2.08 \times 10^3$ |
| Skin Dose (mGy) | 0.036 | 0.029 |
| 2D Image Skin Dose (mGy) | 0.370 | 0.300 |
| 3D Image Skin Dose (mGy) | 4.068 | 3.303 |

It should be noted that the long exposure times (not high dose) needed for detecting Au in samples are caused by the heavy filtering of the emitted X-rays from a normal, 1 kW microfocus X-ray source. Nearly four orders of X-rays are filtered out in this case. If multiple beams and multiple rings of detectors are employed, then the detection times will be shortened.

Discussion

An apparent advantage of this method is to be able to detect small targets loaded with nanoparticles in the body using small X-ray doses (<1 rem). If the conventional CT is used, then over 3 rem of X-ray dose is needed compared to 0.33 rem (see Table 2) needed for the current method to scan a volume of approximately 0.15 cm³. Another advantage is that it may help avoid the problem of partial volume effect associated with CT, which misclassifies small dense objects as large and less dense objects in a large sample, potentially missing the opportunity to diagnose small tumors. Because the diameter of the X-ray needle beam in NAXFI is small, it is unlikely to misclassify these two types of objects.

Figure 23:
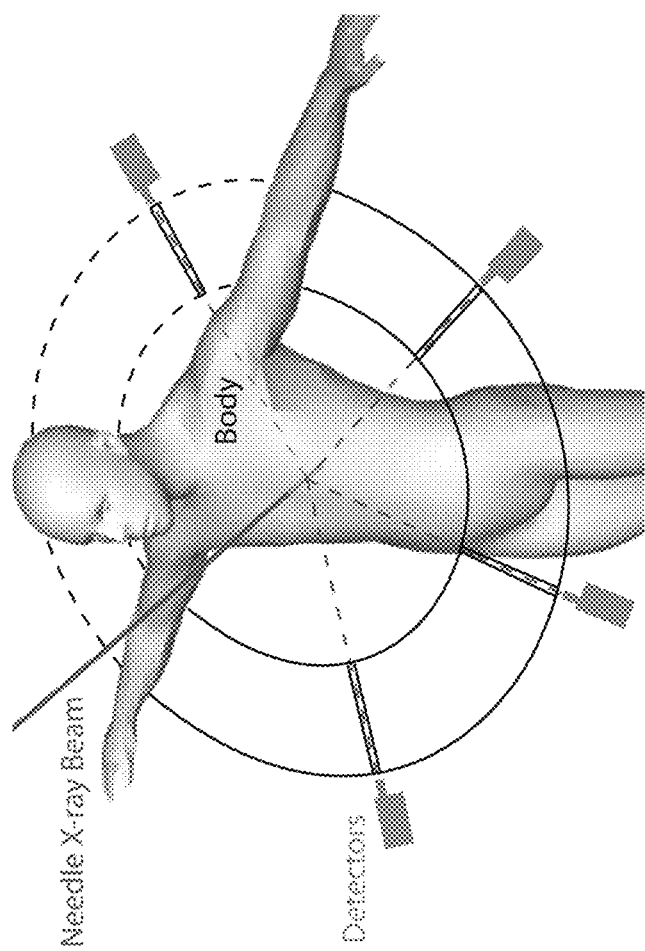
FIG. 23 illustrates an example of imaging a human body using the NAXFI method. The detectors are positioned around the body and the X-ray beam(s) is aimed the region of interest. Only four detectors are shown here.

Because this is essentially a point scan technique (although the scan can be continuous), it is possible to image the sample in any manner, whether it is a line, a slice or a 3D mapping. In practice, it is possible to scan a specific region in the body, as shown in FIG. 23. Complex scanning modes may also be possible. Multiple X-ray needle beams with optimized voltage and spectral filtering and multiple detectors and aperture foci employed in nNB/nF can proportionally shorten the acquisition time.

Figure 24:
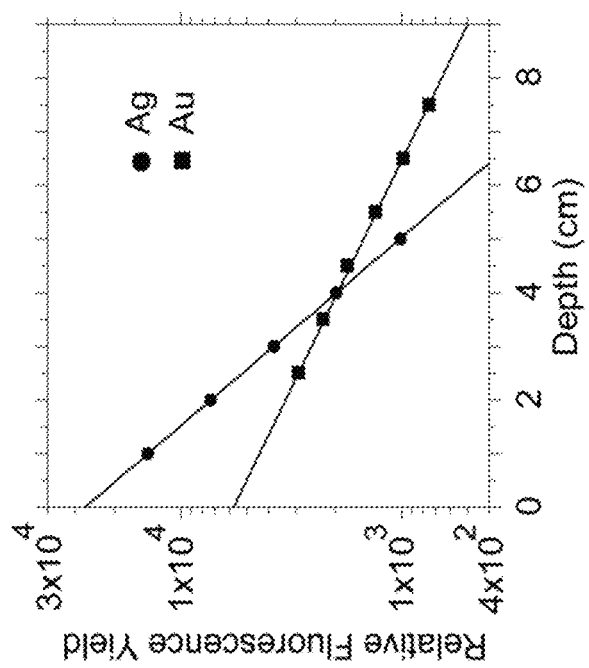
FIG. 24 illustrates escaped fluorescence yield from targets of Ag and Au at different depths in the sample. It shows that Ag is a good reporter for small samples and Au is better for large samples.

The choice of elements of the nanoparticles is important. The dimensions of the sample and depth of the target depend on the choice of the nanoparticles as well. Generally speaking, heavier elements allow deeper detection of targets in larger samples. The limit of the detection is about tens of micrograms for these nanoparticles. This reasoning can be further illustrated in FIG. 24, which shows the relative total fluorescence generated by Ag and Au as a function of depth. It is easier to detect Ag in small samples of 2-3 cm in diameter. Au is used to probe targets in larger 10 cm samples because the fluorescent photons possess more energy (69 keV) and can more efficiently escape the sample. The fluorescence yield is heavily dependent on the filtered X-ray spectra employed in the simulation since the exciting X-ray photon must be greater in energy than the K edge of the absorbing metal. In this simulation, the X-ray spectrum for Ag has a much higher number of photons absorbed above the K edge than in the gold case.

As pointed out above, this method can complement regular CT by imaging specific volumes of interest with higher sensitivity than CT. Conventional PET imaging with radioactive elements can be much more sensitive, but spatial resolution is compromised. Hence the fluorescence-based X-ray imaging method is exceptionally advantageous for imaging small targets buried deeply in large samples. In such a situation, the transmission mode cannot provide enough S/N without overdosing due to strong absorption of X-rays by the whole length of the sample. Instead, X-ray fluorescence only needs to travel less than half of the length of the sample to be detected, therefore providing higher quality images using the same or lower dose than the transmission mode of detection.

Conclusions

Overall, this Example describes an X-ray imaging modality with the assistance of X-ray fluorescent nanoparticles. The spatial resolution can be higher than 1 mm, and the minimum amount of nanoparticles can be less than 10 µg or 0.32 wt. %. An exemplary size of a relatively large sample may be 10 cm. NAXFI may be a complementary imaging tool to other existing imaging methods to detect small tumors and early stage cancers.

Example 4

Additional Information on Nanoparticle-Assisted Scanning Focusing X-Ray Therapy with Needle Beam X-Rays This Example elaborates on the information presented in Example 2. Applicants explored a therapeutic approach that is assisted by X-ray absorbing nanoparticles and enabled by one or more rotating, 40-120 kVp X-ray needle beam(s) pivoting at an isocenter, creating a small volume called the treatment voxel (t-voxel) in the body. This approach makes it possible to deliver hundreds of times more X-ray irradiance and deposited energy to the t-voxel buried centimeters deep in the body than at other adjacent locations, including the skin.

Applicants employed a Monte-Carlo simulation method to evaluate absorption of X-rays delivered by a needle beam of X-rays assisted with X-ray absorbing nanoparticles. Applicants compared this configuration with other possibilities such as thick beams, multiple needle beams, and without the use of nanoparticles. It was found that a three-dimensional scanning of a needle beam of X-rays aiming at a fixed point or isocenter in a sample can significantly increase the X-ray irradiance and dose in a treatment voxel (denoted as t-voxel) at the isocenter than any voxel in the sample including those at the surface. The magnitude of such increase depends on factors such as the beam diameter, scanning geometry, X-ray energy, the composition and size of the sample and the location of t-voxel. Such scanning creates an equivalent three-dimensional focusing effect for the X-rays. In one example, 185 fold dose enhancement within a t-voxel located 5 cm deep in water is predicted when the sample is irradiated with a 2 mm diameter (measured at the target) X-ray beam emitted from a tungsten microfocus X-ray source operated at 60 kVp. The shape of the t-voxel is an oblate spheroid, with the longer axis in the axial direction of the scanning X-rays. Adding X-ray absorbing nanoparticles in the t-voxel further increases the enhancement. For example, dose enhancement with 1 wt. % gold nanoparticles in the t-voxel increases by more than 2 fold over the scanning alone. Altogether, there is a 405 fold increase in dose in the nanoparticle-loaded t-voxel. In the presence of adequate amounts of nanoparticles, the t-voxel adopts the exact shape of the volume of the deposited nanoparticles.

This three-dimensional scanning focusing method, with the assistance of X-ray absorbing nanoparticles and needle beams of X-rays, can deliver more than 400 times more flux or energy to a treatment voxel positioned deeply in the body than at the skin. This method shows that low energy X-rays (40-120 keV) can be used to effectively treat small tumors buried deeply in the body.

Introduction 3D conformal radiation therapy and recent developed intensity-modulated radiation therapy (IMRT) use scans on a plane in a circular fashion with varying sizes and cross-sections of a high energy (MeV) X-ray or electron beam from linear accelerators to deliver more dose to a target. Most techniques employ thick beams whose diameter is greater than 4-5 mm. These large beams are necessary to treat large size tumors, but the magnitude of enhancement derived from rotating such beams is only a few times that of a fixed beam. Compared with these more energetic photons or particles such as MeV X-rays, gamma rays, or electrons, 40-120 keV X-rays are easier to use and can deliver a needle beam to the target that can potentially increase the dose enhancement at the target. However, these X-ray sources are not commonly used in therapy because of strong absorption of these X-rays by tissues, making it difficult to deliver an adequate dose to a target located deeply in the body without damaging healthy tissues in the X-ray beam path, especially those near the skin.

There are several ways to overcome this problem and increase the local dose at a target deep in the body. First, it is possible to quickly rotate one or several X-ray needle beams so that an increased dose can be delivered to a region buried in the body. However, it is difficult for bulkier machines like accelerators to produce needle beams and move in complex 3D geometries. X-ray sources, such as microfocus X-ray tubes, can easily produce needle beams and are inexpensive, more compact, and much more mobile to use than linear accelerators that produce protons, gamma rays, electrons and neutrons. It is hence easier to use these sources to achieve a tight focusing effect, which can create very high enhancement factors as shown below. Rotating X-ray beams have been developed in the past. For instance, Norman et al. in 1991 described a concept of using a rotating beam of X-rays on a plane aiming at an isocenter to enhance the dose at a target in the head (Norman et al., United States Patent, 1991). Up to 10 fold enhancement was measured. Uesaka et al. employed a similar idea, except that they aimed multiple beams on a plane at the target and observed enhancement for high energy X-rays (Uesaka et al., PAC 2007, Albuquerque, N. Mex.: IEEE). Gokeri et al. simulated dose enhancement in the head using arrays of microbeams of X-rays and gold contrast agents (Gokeri et al., Physics in Medicine and Biology, 2010, 55(24): p. 7469-7487). Rahman et al. also employed microbeams from a synchrotron source and gold nanoparticles to study dose enhancement effects in cells (Rahman et al., Cells, 2011, 1: p. 4-13). However, to date, scanning beams on a spherical plane has not yet made 40-120 keV X-rays suitable for cancer treatment.

Another way to increase local dose is to insert X-ray absorbing materials into the target. It is especially advantageous to use X-ray sources operated at 40-120 keV because these nanoparticles can intensely absorb X-rays in the 40-120 keV energy range than water. For example, gold nanoparticles increase the absorption of 40 keV X-rays by 1,000 fold than the same volume of water or by 50 fold for the same weight. This is not the case for gamma rays or MeV electrons, which absorb only 5% more than the same weight of water. The enhanced absorption gives rise to enhanced energy deposition, commonly known as type 1 physical enhancement (T1PE), i.e., averaged over a macroscopic volume, which can reach approximately one fold enhancement for 1 wt. % gold nanoparticles for 40 keV X-rays. Other enhancement types such as local or type 2 physical enhancement (T2PE) may be greater, reaching a few hundred fold within a nanoscopic volume when innovative nanomaterials and mechanisms are employed (Lee et al., J. Phys. Chem. C, 2012, 116(20): p. 11292-11297).

An addition advantage of using low energy, compact X-ray sources is to use them to perform imaging because 40-120 keV X-rays are normally used for X-ray imaging. Therefore, it is possible to achieve diagnosis and treatment with the same X-ray source, which further reduces the cost and complexity of cancer therapy and management. In practice, nanoparticles can be used to increase the absorption of X-rays. If nanoparticles can target tumors, then X-rays can be used to image the tumors and confirm whether nanomaterials have concentrated in the tumors before treatment. Applicants are exploring an imaging method using 40-120 keV X-rays to locate tumors with the assistance of silver and gold nanoparticles in the body (See Examples 1 and 3).

Applicants sought how to improve the enhancement of the dose of X-rays delivered to a target deep in the body with respect to elsewhere in the body including the skin using 40-120 keV X-rays. Applicants studied the geometric configuration of the motion of the X-ray beam to deliver maximum dose enhancement at the target. In addition, nanomaterials were added into the target volume to study how they influence dose enhancement. As mentioned above, there are several types of enhanced absorption and energy deposition reported in the literature (Lee et al., J. Phys. Chem. C, 2012, 116(20): p. 11292-11297; Carter et al., J. Phys. Chem. B, 2007, 111(40): p. 11622-11625). Applicants focus on the absorption enhancement, which is close to energy deposition enhancement when the X-ray energy is just below the K absorption edge.

Experimental/Simulation

Dose Enhancement Principle

Dose enhancement is the ratio of the local dose at a specific location to the maximum dose elsewhere in the body, which usually happens at the skin, and should be relatively uniform across the irradiated surface area by the scanning X-ray needle beam, as shown in the results obtained from this study. The local dose is calculated as the energy deposited per unit volume. The minimum volume used here is $0.5 \times 0.5 \times 0.5$ mm$^3$.

Dose enhancement can be achieved by rotating a needle beam of X-rays pivoted at the isocenter located in a treatment voxel (t-voxel), as shown in FIG. 10. The rotation can happen in two- or three-dimensions (2D and 3D). As the needle beam rotates through the isocenter, energy is constantly deposited in the t-voxel, whereas only a small and varying portion of the rest of the sample is irradiated. Therefore, the amount of dose in the t-voxel may significantly exceed the dose elsewhere if the beam does not overlap itself elsewhere. Although a 2D rotation around the t-voxel was investigated extensively in the past, it is more advantageous to scan the X-ray beam in a 3D focusing configuration along the surface of a spherical cap in order to spread the X-rays into the largest volume to reduce the dose elsewhere. The enhancement effect is particularly prominent for needle X-ray beams. One example is shown in FIG. 10 in which two rotation motions, one around the shaft pointing at the isocenter and the other on a plane through the isocenter, are used to move two X-ray needle beams to form a truncated spherical cap to create an equivalent 3D focusing effect. Another way is to employ two rotary stages to control one X-ray beam to create a similar 3D focusing effect. It is also possible to accomplish this goal with multiple stationary X-ray beams aiming at the isocenter, however to a lesser effect than scanning. In the simulation, both scanning and multiple beam configurations were compared.

X-ray energy is selected by passing X-rays through filters to directly deposit energy in the sample or to excite nanoparticles in the sample. X-ray sources with a tungsten target are used, as well as various metal foil filters to tailor the emission spectrum into the suitable one for maximum excitation of Au nanoparticles in the sample.

The modeling is done using a method developed by Applicants. Briefly, a group of photons emitted from an X-ray tube is simulated using the Monte Carlo method and the photons are tracked as they travel through a water phantom to create a list of photons. Water is used here to represent the soft tissue; the two have similar X-ray attenuation coefficients in this X-ray energy range. In water, energy deposition events are the product of either Compton scattering or photoelectric interactions: these events caused by the X-ray photons interacting with water within a defined volume (called the volume bin or V-bin) are used to determine the dose. Different V-bin dimensions are used to calculate the dose profiles along the axial (Z axis) or in the transverse directions perpendicular to Z direction.

Nanoparticle Assisted Dose Enhancement

Adding nanoparticles made of heavy elements in water can enhance X-ray absorption in the 40-120 keV energy range. If these nanoparticles are only deposited in a t-voxel through targeting, then dose enhancement factor for the t-voxel can be greater. Normally up to 1 wt. % of Ag or Au in the form of nanoparticles can be loaded to a t-voxel, as higher concentrations of these nanoparticles in the t-voxel are more difficult to attain. 1 wt. % of Au nanoparticles are used in the simulation described herein. When nanoparticles are present, the photon list is adjusted to account for photons being stopped within the target volume. X-ray spectra are filtered so that the highest X-ray energy is just under the K edge of the respective metal in the nanoparticles to maximize the local energy deposition. It is assumed that all photons stopped within the nanoparticle-filled volume will lead to 100% local energy deposition because L shell X-ray fluorescence and any electron emission as a result of X-ray absorption will be completely attenuated within the t-voxel described here, which is not the case if X-ray energy is above the K edge of the metal in the target volume. This is the main reason why this X-ray energy spectrum corresponding to photons below the K edge is used.

Results

Figures 25A, 25B, 25C:
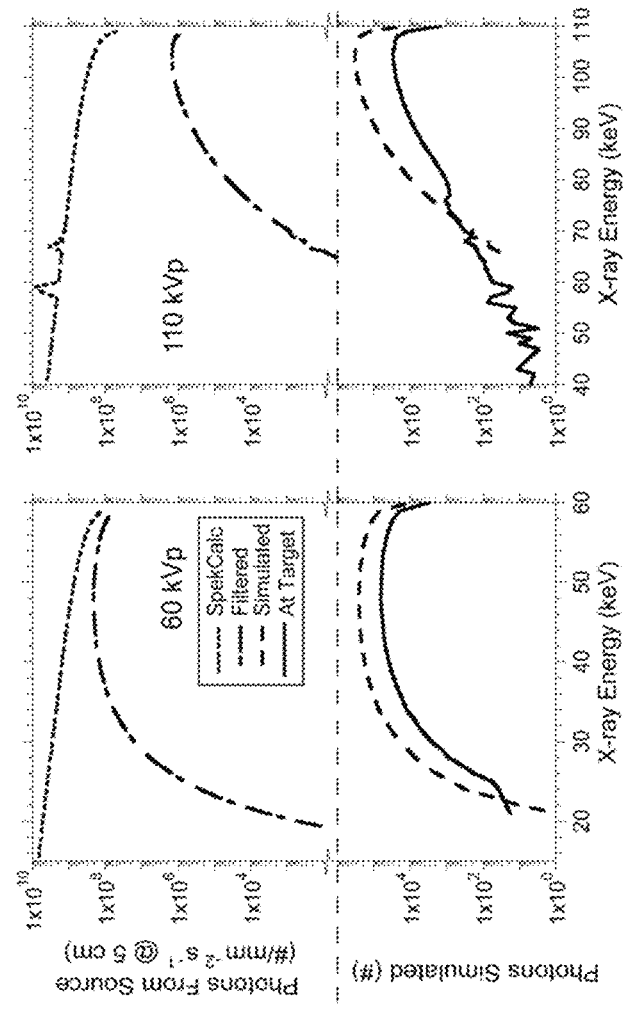
FIG. 25A illustrates the spectra of X-rays from a 60 kVp X-ray source at different locations: from the source (dotted), after 1-mm Al and 0.5-mm Cu foil filters (dotted-dashed), the actually spectrum used for the simulation (dashed) and at the target (solid) in the middle of the sample.
FIG. 25B shows similar energy spectra of the X-rays from a 110-kVp tungsten X-ray source. Filters in this case are 2.5-mm Sn and 1-mm Gd foils.
FIG. 25C shows X-ray intensity of a single X-ray beam as a function of penetration depth. 110 kVp X-rays penetrate 40% deeper than 60 kVp X-rays.

FIG. 25A shows the energy spectra calculated with SpekCalc (dashed line) from a tungsten X-ray source operated at 60 kVp (Poludniowski, G et al., Physics in Medicine and Biology, 2009, 54(19): p. N433-N438). Also shown in FIG. 25A are the filtered X-ray spectrum (dotted-dashed line) and the X-ray photons that are used in the simulation (dashed line) as well as the X-ray spectrum at the target (solid line). FIG. 25B shows the four corresponding spectra for the source operated at 110 kVp. FIG. 25C shows X-ray intensity along the X-ray path as a function of distance from the surface. The decay of X-ray intensity into the sample depends on the energy of X-rays. For 60 kVp X-rays, the attenuation allows X-rays to penetrate 4 cm of water (intensity decreased to 1/e). The depth increases to 6 cm for 110 kVp. FIG. 25C shows why these X-rays are generally not used for treatment due to the high attenuation. For the filtered 60 kVp X-ray spectrum, 30% of X-rays are attenuated at 5 cm.

The energy deposition events are binned into 0.1 cm radius×0.05 cm thick discs in the axial (Z) direction and the dose in these V-bins is calculated to give the axial dose profile shown in FIG. 26. For clarity purpose, the dose is normalized to that at the skin. For calculating transverse dose profiles, energy deposition events are binned to 0.05× 0.05 cm squares sandwiched by two XZ planes 0.2 cm apart (−0.1 to 0.1 cm in the Y direction if the origin is set to the center of the cubic sample) and symmetrically positioned with respect to the isocenter. FIG. 26A shows the results of dose enhancement in the axial direction for the 60 kVp X-rays shown in FIG. 25A for three focusing configurations to increase the local dose at the target located at the center of a 10-cm water cube. It shows the enhancement along the axial direction for 9 needle beams on the same plane (dotted-dashed), 65 needle beams in a three-dimensional configuration (dashed), and continued scanning of one needle beam in 3D (solid). The full width at half maximum (FWHM) of the focus in the axial direction for continuous scanning is 5.8 mm, which is greater than that of 9-beam (2.8 mm) and 65-beam (2.8 mm) focusing configurations for a 2 mm diameter X-ray needle beam. This is mainly attributed to the overlap of the beams in the axial direction, especially in the continuous scanning focusing case which generates an almost flat top dose enhancement profile. As shown in FIG. 26A, more dose is actually deposited in the body and the minimum is at the skin. Only the continuous scan achieves this effect due to the optimal overlap of the scanning X-ray needle beam at the different angles. This makes 40-120 keV X-rays more similar to MeV X-rays or gamma rays.

Figure 26B:
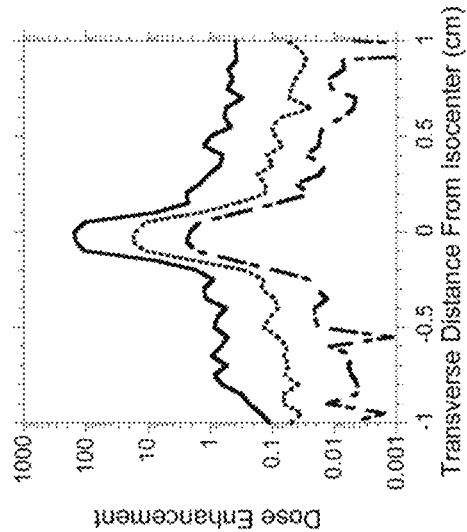
FIGS. 26A-FIG. 26D illustrate X-ray dose enhancement profiles for three configurations of focusing using a beam or beams of X-rays for two different sources operated at 60 (FIG. 26A and FIG. 26B) and 110 kVp (FIG. 26C and FIG. 26D).

FIG. 26B shows the dose enhancement in the transverse direction. It is worth noting that although the transverse enhancement is also normalized against the dose at the skin, the absolute dose differs slightly due to the different binning style mentioned above. The FWHM of the dose enhancement profiles are about 2 mm, approximately the same as the X-ray beam diameter of 2 mm. The focusing employed here therefore creates an oblate spheroid.

Figure 26D:
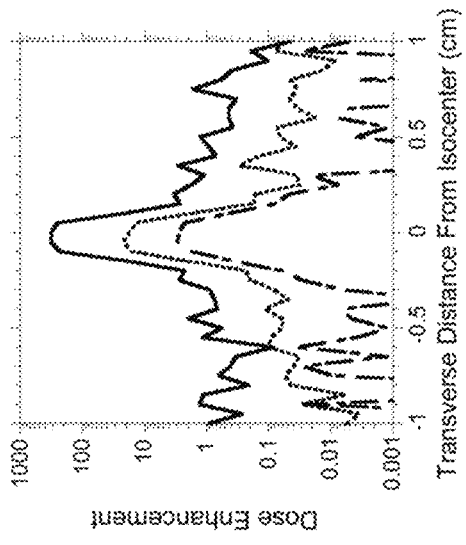
Figure 26A:
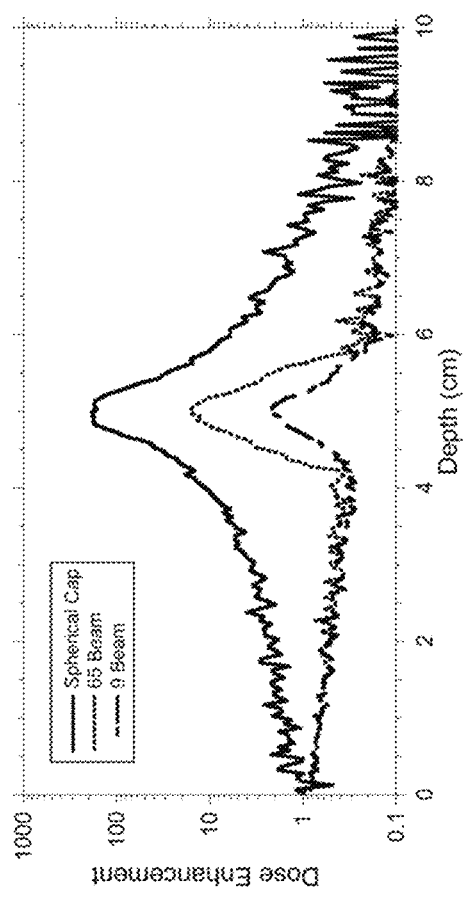

The enhancement for 9 beams on a plane (a 2D focusing) is only 2.2 fold, as shown in FIG. 26A and FIG. 26B. For 65 beams arranged in a 3D spherical cap configuration, the enhancement increases to about 16 fold. On the other hand, the enhancement of the continuous scanning mode is 185 fold for a single needle beam of the same dimension as those used in 9 and 65 beam configurations. Such an enhancement can reduce the surface dose to below 0.1 Gy while the dose at the target exceeds 18 Gy. 0.1 Gy (10 rem) is below the acute dose allowed for human whereas 18 Gy is close to the dose needed to kill a solid tumor (Sachs, R. K. and D. J. Brenner, Proceedings of the National Academy of Sciences of the United States of America, 2005, 102(37): p. 13040-13045). This shows that a continuous scan can overcome the attenuation of a single X-ray beam going into the sample as shown in FIG. 25C, which is 60% at the 5 cm depth. The 9-beam configuration does not compensate such a steep attenuation and the 65-beam configuration delivers a dose at the target this is only 4 times the dose at the skin.

Figure 26C:
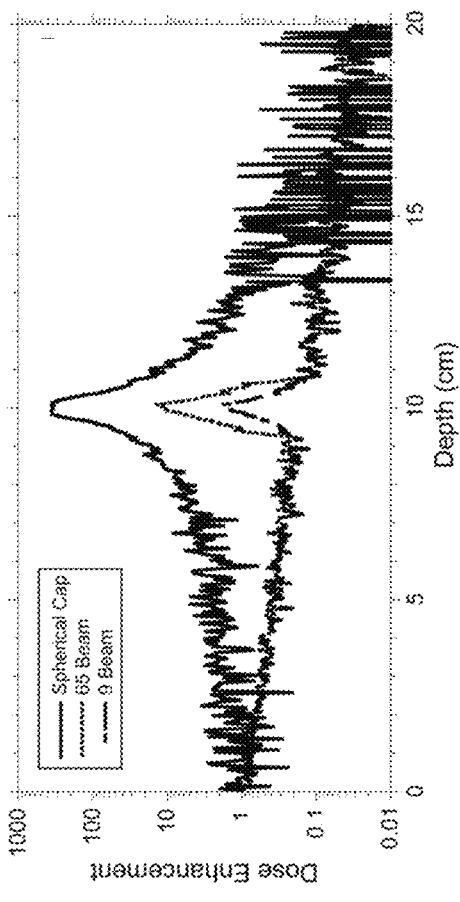

FIG. 26C and FIG. 26D also show the corresponding enhancement profiles for the 110 kVp X-ray spectrum depicted in FIG. 25B. The enhancement factors are higher, reaching 358 fold at the focus. Similarly, the enhanced region is an oblate spheroid, with the longer axis in the axial direction.

FIG. 13A shows the enhancement with the assistance of nanoparticles. In this case, only the region near the focus is shown. When the gold (1 wt. %) is uniformly distributed in a 2 mm thick transverse layer centered at the isocenter, the enhancement is 404-405 fold, which is greater than that for the same weight percentage of gold distributed in a 5 mm thick layer. This reduction for the thicker target is caused by attenuation of X-rays near the focal point in the thicker Au layer. The result of continuous scan for Au is shown in FIG. 13A. The enhancement is 318-319 fold when an equal wt. % of Au is used in a larger volume (5 mm thick).

A clear advantage of using the nanoparticles is the well-defined enhancement region with the introduction of nanomaterials. The FWHM improves from a less well-defined t-voxel in the axial direction to almost the exact shape of the volume containing Au. The shape of the enhancement region essentially adopts that of the loaded nanoparticles.

FIG. 14 shows a 2D X-ray dose enhancement plot on a plane parallel to the axial Z-axis and through the focus near the t-voxel. The 3D shape of the t-voxel shown here is oblate spheroidal with the longer axis along the axial direction for the scanning 2-mm diameter X-ray beam. This shape determines the resolution of the energy deposition profile, which has a higher resolution in the transverse directions than axial due to the fact that the rotating X-ray needle beam deposit more energy in front of and behind the t-voxel. The solid angle of X-rays hitting the t-voxel is clearly visible in FIG. 14 going from polar angle of −22.5° to +22.5° or 0.48 sr with respect to the axial direction on any transverse plane. The enhancement in the t-voxel relative to the skin is dependent of the solid angle; the greater the solid angle, the greater the enhancement and a stronger focusing effect. In cancer therapy, larger solid angles may be used, which means even greater enhancement than those presented here may be obtained.

After the addition of nanoparticles, which occupy a cylindrical volume, the shape of t-voxel defined by the shape of energy deposition profile adopts that of the nanoparticles, as shown in FIG. 14B. This higher spatial resolution of enhanced regions after addition of nanoparticles may facilitate precision treatment of cancer.

Discussion

Applicants method described herein using X-rays can deposit significant energy in the body. The main reason for using MeV sources derives from the large penetration depth of these energetic particles so that more energy can be deposited deep in the body rather than the skin. The use of 40-120 keV X-ray sources in the scanning focusing configuration discussed herein can overcome the shallow penetration problem associated with these sources so that these compact sources can be used in cancer treatment.

The advantage of using a scanning needle beam of X-rays over other configurations, such as multiple stationary beams or a thick beam, lies in the fact that only the thin scanning beam configuration allows the beam to cover as large a solid angle as possible at the entrance of the skin while minimizing the time of the scanning beam irradiating any specific area of the skin. Because a stationary single beam of X-rays in the range of 40-120 keV will always deliver more dose at the skin along a specific X-ray path, the only way to deliver more dose deep in the body is to rotate a needle beam so that any area of the skin is only exposed to X-rays for a very shorter time while the t-voxel is constantly being irradiated. The thinner the needle beam, the higher the enhancement.

Figure 27:
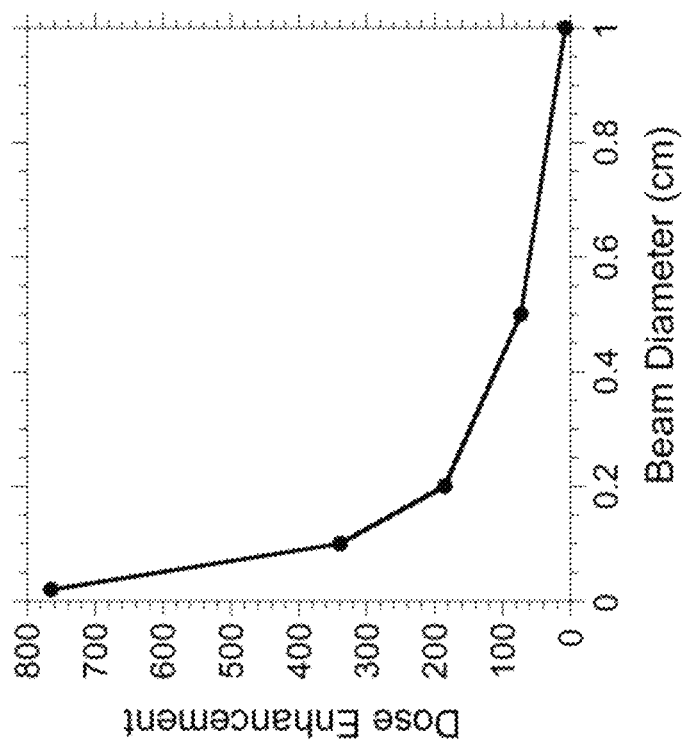
FIG. 27 illustrates the maximum dose at the focus as a function of the beam diameter at the t-voxel. The increase of dose enhancement goes from 8 fold to 766 fold as the beam size decreases from 1 cm to 0.05 cm. A 1 mm diameter X-ray beam is used throughout the experiments presented in Example 4.

It is important to point out the enhancement of 405 times (the dose deposited at the target over the dose at the skin) occurs for small targets deep in the sample or body. For larger targets such as those in 3D conformal cancer therapy, the X-ray beam size may need to increase, which will reduce the magnitude of enhancement. FIG. 27 shows the relationship between the magnitude of the enhancement and the diameter of the X-ray beam. It shows that the enhancement (relative dose in the t-voxel) increases significantly as the beam size drops below 2 mm. The choice of the diameter should be considered in conjunction with the treatment time: too large a diameter the beam will not create adequate enhancement, yet too small a diameter and the beam delivers much less X-rays per unit time into the t-voxel, even though the enhancement is much greater.

It is also possible to move the t-voxel formed by the scanning of a needle X-ray beam to cover the larger target. However, this will also reduce the enhancement because although the t-voxel moves from one spot to another completely different spot, the two X-ray cones responsible for the two t-voxels occupy approximately the same space, effectively reducing the enhancement by half. One way to maintain high enhancement in practical cancer therapy is to deliver dose to only one small spot at a time to kill tumor tissue at the t-voxel. Subsequent deliveries to an adjacent spot can be made at a delayed time to allow the healthy tissues in the beam path to completely recover. Large solid tumors may be killed in this way.

It is also worth pointing out that the 3D scanning focusing approach described herein can be combined with other methods such as X-ray triggered release of chemotherapeutic drugs to further reduce the dose to below the acute level (0.1 Gy) in the healthy tissues and completely eradicate a tumor within the targeted volume via the activation of chemotherapeutic drugs (Starkewolf et al., Chemical Communications, 2013, 49(25): p. 2545-2547).

It seems the enhancement due to the introduction of nanomaterials is small compared with that of scanning beam(s). Although this is true, there are three important improvements with the use of nanomaterials. First, it is important to realize that these nanomaterials may help diagnose cancer through nanomaterials-assisted imaging if these nanomaterials can target tumors (Dreaden, E. C et al., Small, 2012, 8(18): p. 2819-2822). The net benefits of being able to reveal cancer locations and creating higher local dose at these locations compensate the added complexity of using nanomaterials. Secondly, nanomaterials can improve the spatial resolution of dose enhancement, as shown above, from a few mm to less than one mm. Third, it is possible to use these nanomaterials to generate other types of enhancement such as type 2 physical enhancement (T2PE), which can reach more than 200 fold enhancement using specially arranged nanostructures (Lee, C et al., J. Phys. Chem. C, 2012, 116(20): p. 11292-11297).

The scattered X-rays create a weak background around the X-ray beam. This background contains a small amount of energy. This is because X-ray attenuation is largely through Compton scattering of X-rays by water molecules, and the Compton electrons deposit all their energy in the immediate space (within microns) of the scattering events. In the presence of nanoparticles made of heavy elements, the situation is slightly different. If X-ray energy above the K absorption edge is used, fluorescent X-rays may have enough energy to redeposit energy in the whole sample, so this part of the secondary energy deposition reduces the enhancement by a small margin. The enhancement caused by X-ray fluorescence from the nanoparticles is hence insignificant compared with the enhanced absorption and amount of energy retained by the electrons within the t-voxel. Because of this secondary redistribution of absorbed X-ray energy, X-ray photons with energy above K edges are less useful in giving rise to enhanced energy deposition in the target t-voxel.

A noticeable feature of 3D scanning focusing using needle beams is that more dose is delivered in body along the beam path, with the maximum at the focus. Although this is ideal for treatment, it does suggest that the true enhancement should be calculated using the maximum dose outside the focus, which actually decreases monotonically from the focus to the skin. This makes it difficult to define the enhancement factor, so instead the dose at the skin is used in this work to define the enhancement. In practice, the dose around the focus should be considered and managed to avoid damage to healthy tissues or organs.

Applicant's method described herein shares some features with intensity-modulated radiation therapy (IMRT), i.e. RapidArc, in which linear accelerators are used to point MeV photon beams at the target from different angles to deliver more dose to the target while minimizing the dose in the surrounding healthy tissues. The scans are generally made on the same plane while the shape and the intensity of the photon beam are varied to deliver the maximum dose to the tumor target. Due to the relative large beam size and confined scan space, the dose enhancement is limited. In contrast, Applicants method investigated herein takes advantage of the much more mobile X-ray sources to perform 3D focusing using a needle X-ray beam(s) to significantly reduce the dose elsewhere than that at target. Other techniques, such as GammaKnife, may also benefit from the approach developed here: instead of using multiple radioactive sources, it is possible to use only one to create a scanning needle beam for effective high dose delivery at the isocenter.

The scanning focusing method can also be used to excite X-ray fluorescence for imaging, which was described recently (Davidson et al., to be submitted). However, the speed of movement of the X-ray source(s) needs to be fast because only a small fraction of the total dose at the target is required for imaging. If a large volume of target needs to be imaged, it is still beneficial to employ scanning focusing imaging to lower the dose in tissues at shallow depths including surface.

CONCLUSIONS

A three-dimensional continuous scanning of an X-ray needle beam(s) aimed at an isocenter can increase the dose at the center over that at the skin by many hundred times. The magnitude of enhancement depends on the X-ray beam diameter, energy, range of movement, composition and size of the sample, and the depth of the t-voxel. A 185 fold dose increase over that the skin dose can be achieved at 5 cm deep in the water. Upon adding X-ray absorbing nanoparticles into the t-voxel, the enhancement can increase by many folds in addition to the scanning caused enhancement. For 1 wt. % Au nanoparticles that do not interfere with energy release and scavenging, the enhancement is another 2 fold increase over the scanning enhancement, resulting in an overall enhancement of 405 fold. Other elements and X-ray energies can be used and similarly high enhancement factors are predicted. The shape of enhancement is oblate spheroidal for focusing without nanoparticles, and adopts that of loaded nanoparticles with 1 wt. % Au nanoparticles.

REFERENCES

Luo, T., P. Huang, G. Gao, G. X. Shen, S. Fu, D. X. Cui, C. Q. Zhou, and Q. S. Ren, Mesoporous silica-coated gold nanorods with embedded indocyanine green for dual mode X-ray CT and NIR fluorescence imaging. Optics Express, 2011. 19(18): p. 17030-17039.

Meng, L., G. Fu, N. Li, M. Newville, P. Eng and P. La Riviere, X-ray fluorescence tomography using imaging detectors. Proc. of SPIE, 2010. 7804: p. B1-B9.

Jones, B. L., N. Manohar, F. Reynoso, A. Karellas, and S. H. Cho, Experimental demonstration of benchtop x-ray fluorescence computed tomography (XFCT) of gold nanoparticle-loaded objects using lead- and tin-filtered polychromatic cone-beams. Physics in Medicine and Biology, 2012. 57(23): p. N457-N467.

Bazalova, M., Y. Kuang, G. Pratx, and L. Xing, Investigation of X-ray Fluorescence Computed Tomography (XFCT) and K-Edge Imaging. Ieee Transactions on Medical Imaging, 2012. 31(8): p. 1620-1627.

Bazalova, M., G. Pratx, Y. Kuang, and L. Xing, X-ray Imaging Beyond Transmission CT: Detecting Low Concentrations of Gold Nanoparticles. International Journal of Radiation Oncology Biology Physics, 2012. 84(3): p. S689-S689.

Bazalova, M., M. D. Weil, B. Wilfley, and E. E. Graves, Monte Carlo model of the scanning beam digital x-ray (SBDX) source. Physics in Medicine and Biology, 2012. 57(22): p. 7381-7394.

Chan, H. P. and K. Doi, The Validity of Monte-Carlo Simulation in Studies of Scattered Radiation in Diagnostic-Radiology. Physics in Medicine and Biology, 1983. 28(2): p. 109-129.

National Institute of Standards and Technology. Available from: http://www.nist.gov/srd/nist64.htm.

Hubbell, J. H., W. J. Veigele, E. A. Briggs, R. T. Brown, D. T. Cromer, and R. J. Howerton, Atomic form factors, incoherent scattering functions, and photon scattering cross-sections. J. Phys. Chem. Ref. Data, 1975. 4(3): p. 471-493.

Compton, A. H., The spectrum of scattered x-rays. Physical Review, 1923. 22(5): p. 0409-0413.

Davidson, R. A. and T. Guo, Nanoparticle Assisted Three Dimensional Point Scan X-ray Fluorescence Imaging. To be submitted, 2013.

Lee, C., N. N. Cheng, R. A. Davidson, and T. Guo, Geometry Enhancement of Nanoscale Energy Deposition by X-rays. J. Phys. Chem. C, 2012. 116(20): p. 11292-11297.

Norman, A. and K. S. Iwamoto, Therapy X-ray Scanner, in United States Patent 1991, The Regents of the University of California: USA.

Uesaka, M., K. Mizumo, A. Sakumi, J. Meiling, N. Yusa, N. Nishiyama, and K. Nakagawa. Pinpoint KEV/MEV X-ray Sources for X-ray Drug Delivery System. in PAC. 2007. Albuquerque, N. Mex.: IEEE.

Carter, J. D., N. N. Cheng, Y. Q. Qu, G. D. Suarez, and T. Guo, Nanoscale energy deposition by x-ray absorbing nanostructures. J. Phys. Chem. B, 2007. 111(40): p. 11622-11625.

Poludniowski, G., G. Landry, F. DeBlois, P. M. Evans, and F. Verhaegen, SpekCalc: a program to calculate photon spectra from tungsten anode x-ray tubes. Physics in Medicine and Biology, 2009. 54(19): p. N433-N438.

Sachs, R. K. and D. J. Brenner, Solid tumor risks after high doses of ionizing radiation. Proceedings of the National Academy of Sciences of the United States of America, 2005. 102(37): p. 13040-13045.

Starkewolf, Z. B., L. Miyachi, J. Wong, and T. Guo, X-ray triggered release of doxorubicin from nanoparticle drug carriers for cancer therapy. Chemical Communications, 2013. 49(25): p. 2545-2547.

Dreaden, E. C., S. C. Mwakwari, L. A. Austin, M. J. Kieffer, A. K. Oyelere, and M. A. El-Sayed, Small Molecule-Gold Nanorod Conjugates Selectively Target and Induce Macrophage Cytotoxicity towards Breast Cancer Cells. Small, 2012. 8(18): p. 2819-2822.

Hainfeld, J. F., M. J. O'Connor, F. A. Dilmanian, D. N. Slatkin, D. J. Adams, and H. M. Smilowitz, Micro-CT enables microlocalisation and quantification of Her2-targeted gold nanoparticles within tumour regions. British Journal of Radiology, 2011. 84(1002): p. 526-533.

Manohar, N., F. J. Reynoso, and S. H. Cho, Experimental demonstration of direct L-shell x-ray fluorescence imaging of gold nanoparticles using a benchtop x-ray source. Medical Physics, 2013. 40(8).

Anderson, D. S., E. S. Patchin, R. G. Silva, D. L. Uyeminami, A. Sharmah, T. Guo, J. M. Brown, J. Shannanhan, T. Gordon, L. C. Chen, K. E. Pinkerton, and L. S. Van Winkle, Influence of particle size on persistence and clearance of Aerosolized Silver Nanoparticles in the Rat Lung. To be submitted, 2014.

Gokeri, G., C. Kocar, and M. Tombakoglu, Monte Carlo simulation of microbeam radiation therapy with an interlaced irradiation geometry and an Au contrast agent in a realistic head phantom. Physics in Medicine and Biology, 2010. 55(24): p. 7469-7487.

Rahman, W. N., R. Davidson, N. Yagi, V. Bansal, M. Geso, and I. Darby, Influence of Gold Nanoparticles on Radiation Dose Enhancement and Cellular Migration in Microbeam-Irradiated Cells, 2011. 1: p. 4-13.

What is claimed is:

1. A method of detecting a target using X-ray fluorescence imaging, the method comprising:
   a) providing a sample comprising nanoparticles, wherein the nanoparticles are configured to be associated with a target;
   b) irradiating the sample with one or more X-ray beams during a continuous scanning operation,
      wherein the one or more X-ray beams have a defined cross-section, and
      wherein nanoparticles in the sample contacted by the one or more X-ray beams reflect X-ray fluorescence;
   c) scanning a first i-voxel with a detector,
      wherein a path of detection is formed from the irradiated sample to the detector,
      wherein the path of detection has a defined cross-section, and
      wherein the detector is configured to detect reflected X-ray fluorescence in an i-voxel formed by the area of intersection of the defined cross-section of the one or more X-ray beams and the defined cross-section of the path of detection;
   d) scanning a second i-voxel adjacent to the first i-voxel with the detector;
   e) comparing the detection of reflected X-ray fluorescence in the first i-voxel to the detection of reflected X-ray fluorescence in the second i-voxel;
   f) determining if the sample comprises the target;
   g) identifying the target within the sample,
      wherein the sample comprises a t-voxel comprising an isocenter located in the interior of the sample, and a volume having equivalent volume to the t-voxel located adjacent to a surface of the sample,
      wherein the volume having equivalent volume to the t-voxel does not include the isocenter; and
   h) irradiating the isocenter with one or more X-ray beams from at least three angles,
      wherein the isocenter is irradiated from at least one angle that is out of plane with at least one plane formed by two other angles,
      wherein deposition of the irradiation energy from the one or more X-ray beams is greater at the t-voxel as compared to the volume having equivalent volume to the t-voxel, and wherein irradiation of the isocenter occurs for a period of time sufficient for the deposition to occur.

2. The method of claim 1, wherein one or more of the nanoparticles comprise a metal selected from the group consisting of silver and gold.

3. The method of claim 1, wherein the sample comprises about 10 µg or less nanoparticles.

4. The method of claim 1, wherein the first or second i-voxel comprises about 0.33 wt. % or fewer nanoparticles.

5. The method of claim 1, wherein the sample is about 15 cm or more in dimension.

6. The method of claim 1, wherein detection of reflected X-ray fluorescence occurs about 10 cm or deeper within the sample.

7. The method of claim 1, wherein detection time is about 60 minutes or less.

8. The method of claim 1, wherein the target is a tumor.

9. The method of claim 8, wherein the tumor is about 1 mm or less in dimension.

10. A method of delivering irradiation energy to a sample, the method comprising:
   a) providing a sample comprising a t-voxel comprising an isocenter located in the interior of the sample, and a volume having equivalent volume to the t-voxel located adjacent to a surface of the sample,
      wherein the volume having equivalent volume to the t-voxel does not include the isocenter;
   b) irradiating the isocenter with one or more X-ray beams from at least three angles, wherein each of the one or more X-ray beams is characterized by a diameter at the sample of less than or about 2 mm, wherein the one or more X-ray beams rotate about the isocenter,
      wherein the isocenter is irradiated from at least one angle that is out of plane with at least one plane formed by two other angles,
      wherein deposition of the irradiation energy from the one or more X-ray beams is greater at the t-voxel as compared to the volume having equivalent volume to the t-voxel, wherein irradiation of the isocenter occurs for a period of time sufficient for the deposition to occur;
   c) providing the sample with nanoparticles, wherein the nanoparticles are configured to be associated with a target;
   d) irradiating the sample with one or more X-ray beams, wherein the one or more X-ray beams have a defined cross-section, and
      wherein nanoparticles in the sample contacted by the one or more X-ray beams reflect X-ray fluorescence;
   e) scanning a first i-voxel with a detector,
      wherein a path of detection is formed from the irradiated sample to the detector,
      wherein the path of detection has a defined cross-section, and
      wherein the detector is configured to detect reflected X-ray fluorescence in an i-voxel formed by the area of intersection of the defined cross-section of the one or more X-ray beams and the defined cross-section of the path of detection;
   f) scanning a second i-voxel adjacent to the first i-voxel with the detector;
   g) comparing the detection of reflected X-ray fluorescence in the first i-voxel to the detection of reflected X-ray fluorescence in the second i-voxel, and
   h) determining if the sample comprises the target.

11. The method of claim 10, wherein the rotation is three-dimensional.

12. The method of claim 10, wherein irradiation energy deposition at the t-voxel is increased about 185-fold or more as compared to the volume having equivalent volume to the t-voxel.

13. The method of claim 12, wherein irradiation energy deposition at the t-voxel is increased in the range of about 400-fold to about 800-fold or more as compared to the volume having equivalent volume to the t-voxel.

14. The method of claim 10, wherein the sample comprises one or more nanoparticles.

15. The method of claim 14, wherein one or more of the nanoparticles comprise a metal selected from the group consisting of silver and gold.

16. The method of claim 15, wherein for gold nanoparticles, the irradiation energy is in the range of about 50 keV to about 80 keV.

17. The method of claim 10, wherein the t-voxel comprises about 1.0 wt. % or fewer nanoparticles.

18. The method of claim 10, wherein the detection occurs about 5 cm or deeper within the sample.

19. The method of claim 10, wherein the irradiation energy is in the range of about 40 keV to about 130 keV.

20. The method of claim 10, where the diameter of the one or more X-ray beams is less than 2 mm at the target.

21. The method of claim 10, wherein the surface of the sample is skin.

* * * * *